United States Patent
Suzuki et al.

(10) Patent No.: US 11,121,326 B2
(45) Date of Patent: Sep. 14, 2021

(54) ORGANIC COMPOUND, LIGHT-EMITTING ELEMENT, LIGHT-EMITTING DEVICE, ELECTRONIC DEVICE AND LIGHTING DEVICE

(71) Applicant: Semiconductor Energy Laboratory Co., Ltd., Kanagawa-ken (JP)

(72) Inventors: Hiroki Suzuki, Kanagawa (JP); Tomoya Yamaguchi, Kanagawa (JP); Hideko Yoshizumi, Kanagawa (JP); Satoshi Seo, Kanagawa (JP); Tatsuyoshi Takahashi, Kanagawa (JP); Hiromitsu Kido, Kanagawa (JP); Satomi Watabe, Kanagawa (JP)

(73) Assignee: Semiconductor Energy Laboratory Co., Ltd.

( * ) Notice: Subject to any disclaimer, the term of this patent is extended or adjusted under 35 U.S.C. 154(b) by 0 days.

(21) Appl. No.: 16/940,724

(22) Filed: Jul. 28, 2020

(65) Prior Publication Data
US 2020/0358003 A1 Nov. 12, 2020

Related U.S. Application Data

(63) Continuation of application No. 15/674,943, filed on Aug. 11, 2017, now Pat. No. 10,734,589.

(30) Foreign Application Priority Data

Aug. 17, 2016 (JP) .................................. 2016-159794
May 23, 2017 (JP) .................................. 2017-102066

(51) Int. Cl.
*H01L 51/00* (2006.01)
*C07D 491/048* (2006.01)
(Continued)

(52) U.S. Cl.
CPC ...... *H01L 51/0071* (2013.01); *C07D 491/048* (2013.01); *H01L 51/0074* (2013.01);
(Continued)

(58) Field of Classification Search
None
See application file for complete search history.

(56) References Cited

U.S. PATENT DOCUMENTS 7,175,922 B2 2/2007 Jarikov et al.
7,183,010 B2 2/2007 Jarikov
(Continued)

FOREIGN PATENT DOCUMENTS

CN 104011058 A 8/2014
CN 104136430 A 11/2014
(Continued)

OTHER PUBLICATIONS

Zametetal. (J. Chem. Soc. Perk. T. 1: Org. Bio-org. Chem. 1974, 14, p. 1687).*
(Continued)

*Primary Examiner* — Jay Yang
(74) *Attorney, Agent, or Firm* — Husch Blackwell LLP

(57) ABSTRACT

A novel organic compound is provided. That is, a novel organic compound that is effective in improving the element characteristics and reliability is provided. The organic com-
(Continued)

pound has a benzofuroquinoxaline skeleton or a benzothienoquinoxaline skeleton. The organic compound is represented by General Formula (G1).

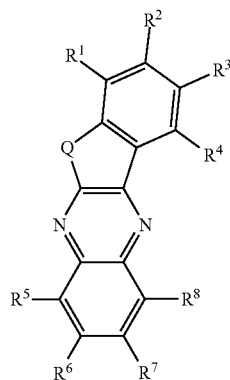

(G1)

In the formula, Q represents O or S, and each of R1 to R8 independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. At least one of R1 to R8 includes a substituted or unsubstituted condensed aromatic or heteroaromatic ring having 3 to 24 carbon atoms.

14 Claims, 38 Drawing Sheets

(51) Int. Cl.
*H05B 33/20* (2006.01)
*H01L 51/50* (2006.01)
*C09K 11/06* (2006.01)

(52) U.S. Cl.
CPC .............. *H05B 33/20* (2013.01); *C09K 11/06* (2013.01); *C09K 2211/1007* (2013.01); *C09K 2211/1044* (2013.01); *C09K 2211/185* (2013.01); *H01L 51/0085* (2013.01); *H01L 51/5012* (2013.01); *H01L 51/5016* (2013.01); *H01L 51/5072* (2013.01); *H01L 2251/308* (2013.01)

(56) References Cited

U.S. PATENT DOCUMENTS

| | | | |
|---|---|---|---|
| 7,332,857 B2 | 2/2008 | Seo et al. |
| 7,597,967 B2 | 10/2009 | Kondakova et al. |
| 7,906,226 B2 | 3/2011 | Matsuura et al. |
| 7,993,760 B2 | 8/2011 | Komori et al. |
| 8,034,465 B2 | 10/2011 | Liao et al. |
| 8,105,701 B2 | 1/2012 | Matsuura et al. |
| 8,274,214 B2 | 9/2012 | Ikeda et al. |
| 8,470,455 B2 | 6/2013 | Matsuura et al. |
| 8,853,680 B2 | 10/2014 | Yamazaki et al. |
| 8,963,127 B2 | 2/2015 | Pieh et al. |
| 8,981,355 B2 | 3/2015 | Seo |
| 8,993,129 B2 | 3/2015 | Endo et al. |
| 8,994,263 B2 | 3/2015 | Shitagaki et al. |
| 9,054,317 B2 | 6/2015 | Monkman et al. |
| 9,159,942 B2 | 10/2015 | Seo et al. |
| 9,175,213 B2 | 11/2015 | Seo et al. |
| 9,356,250 B2 | 5/2016 | Ohsawa et al. |
| 9,604,928 B2 | 3/2017 | Shitagaki et al. |
| 2003/0175553 A1 | 9/2003 | Thompson et al. |
| 2005/0048310 A1 | 3/2005 | Cocchi et al. |
| 2005/0221116 A1 | 10/2005 | Cocchi et al. |
| 2006/0134464 A1 | 6/2006 | Nariyuki |
| 2006/0210828 A1 | 9/2006 | Nakayama et al. |
| 2007/0090756 A1 | 4/2007 | Okada et al. |
| 2012/0217487 A1 | 8/2012 | Yamazaki et al. |
| 2013/0165653 A1 | 6/2013 | Inoue et al. |
| 2014/0110686 A1 | 4/2014 | Fujita et al. |
| 2014/0117331 A1 | 5/2014 | Kim et al. |
| 2014/0291645 A1 | 10/2014 | Inoue et al. |
| 2015/0041784 A1 | 2/2015 | Shizu et al. |
| 2015/0069352 A1 | 3/2015 | Kim et al. |
| 2016/0141515 A1 | 5/2016 | Hayama et al. |
| 2016/0163997 A1 | 6/2016 | Noh et al. |
| 2017/0186971 A1 | 6/2017 | Kanamoto et al. |

FOREIGN PATENT DOCUMENTS

| | | |
|---|---|---|
| CN | 105283977 A | 1/2016 |
| CN | 105670606 A | 6/2016 |
| DE | 112012005364 | 10/2014 |
| EP | 1202608 A | 5/2002 |
| EP | 2808323 A | 12/2014 |
| EP | 3010055 A | 4/2016 |
| EP | 3029125 A | 6/2016 |
| GB | 963036 * | 8/1964 |
| JP | 2004-241374 A | 8/2004 |
| JP | 2008-288344 A | 11/2008 |
| JP | 2010-182699 A | 8/2010 |
| JP | 2013-147496 A | 8/2013 |
| JP | 2013-256490 A | 12/2013 |
| JP | 2014-080402 A | 5/2014 |
| JP | 2014-209611 A | 11/2014 |
| JP | 2015-227328 A | 12/2015 |
| JP | 2016-108338 A | 6/2016 |
| JP | 2016-135775 A | 7/2016 |
| JP | 2014/199637 | 2/2017 |
| KR | 2014-0107310 A | 9/2014 |
| KR | 2015-0009512 A | 1/2015 |
| KR | 2015-0027443 A | 3/2015 |
| KR | 2015-0132993 A | 11/2015 |
| KR | 2016-0018458 A | 2/2016 |
| KR | 2016-0068641 A | 6/2016 |
| TW | 201333019 | 8/2013 |
| TW | 201350558 | 12/2013 |
| WO | WO-2013/094620 | 6/2013 |
| WO | WO-2013/172255 | 11/2013 |
| WO | WO-2014/199637 | 12/2014 |
| WO | WO 2015/167223 A1 | 11/2015 |
| WO | WO-2016/034708 A1 * | 3/2016 |

OTHER PUBLICATIONS

Camaggi, C. et al., "Radical Annulations with Nitriles: Novel Cascade Reactions of Cyano-Substituted Alkyl and Sulfanyl Radicals with Isonitriles," Tetrahedron, May 21, 1998, vol. 54, No. 21, pp. 5587-5598.

Yersin, H. et al., *Highly Efficient OLEDs with Phosphorescent Materials*, 2008, pp. 1-97,283-309, Wiley-VCH Verlag GmbH & Co.

Tokito,S. et al., "Improvement in Performance by Doping," Organic EL Display, Aug. 20, 2004, pp. 67-99, Ohmsha.

Jeon, W. et al., "Ideal Host and Guest System in Phosphorescent OLEDs," Organic Electronics, 2009, vol. 10, pp. 240-246, Elsevier.

Su, S. et al., "RGB Phosphorescent Organic Light-Emitting Diodes by Using Host Materials with Heterocyclic Cores:Effect of Nitrogen Atom Orientations," Chemistry of Materials, 2011, vol. 23, No. 2, pp. 274-284.

Rausch, A.F. et al., "Matrix Effects on the Triplet State of the OLED Emitter Ir(4,6-dFppy)2(pic)(FIrpic): Investigations by High-Resolution Optical Spectroscopy," Inorganic Chemistry, 2009, vol. 48, No. 5, pp. 1928-1937.

(56) References Cited

OTHER PUBLICATIONS

Gong, X. et al., "Phosphorescence from Iridium Complexes Doped into Polymer Blends," Journal of Applied Physics, Feb. 1, 2004, vol. 95, No. 3, pp. 948-953.

Zhao, Q. et al., "Synthesis and Photophysical, Electrochemical, and Electrophosphorescent Properties of a Series of Iridium(III) Complexes Based on Quinoline Derivatives and Different β-Diketonate Ligands," Organometallics, Jun. 14, 2006, vol. 25, No. 15, pp. 3631-3638.

Hino, Y. et al., "Red Phosphorescent Organic Light-Emitting Diodes Using Mixture System of Small-Molecule and Polymer Host," Japanese Journal of Applied Physics, Apr. 21, 2005, vol. 44, No. 4B, pp. 2790-2794.

Tsuboyama, A. et al., "Homoleptic Cyclometalated Iridium Complexes with Highly Efficient Red Phosphorescence and Application to Organic Light-Emitting Diode," Journal of the American Chemical Society, 2003, vol. 125, No. 42, pp. 12971-12979.

Kondakova, M.et al., "High-Efficiency, Low-Voltage Phosphorescent Organic Light-Emitting Diode Devices with Mixed Host," Journal of Applied Physics, Nov. 4, 2008, vol. 104, pp. 094501-1-094501-17.

Chen, F-C. et al., "Triplet Exciton Confinement in Phosphorescent Polymer Light-Emitting Diodes," Applied Physics Letters, Feb. 17, 2003, vol. 82, No. 7, pp. 1006-1008.

Lee, J. et al., "Stabilizing the Efficiency of Phosphorescent Organic Light-Emitting Diodes," SPIE Newsroom, Apr. 21, 2008, pp. 1-3.

Tokito, S. et al., "Confinement of Triplet Energy on Phosphorescent Molecules for Highly-Efficient Organic Blue-Light-Emitting Devices," Applied Physics Letters, Jul. 21, 2003, vol. 83, No. 3, pp. 569-571.

Endo, A. et al., "Efficient Up-Conversion of Triplet Excitons Into a Singlet State and Its Application for Organic Light Emitting Diodes," Applied Physics Letters, Feb. 24, 2011, vol. 98, No. 8, pp. 083302-1-083302-3.

Itano, K. et al., "Exciplex Formation at the Organic Solid-State Interface: Yellow Emission in Organic Light-Emitting Diodes Using Green-Fluorescent tris(8-quinolinolato)aluminum and Hole-Transporting Molecular Materials with Low Ionization Potentials," Applied Physics Letters, Feb. 9, 1998, vol. 72, No. 6, pp. 636-638.

Park, Y. et al., "Efficient Triplet Harvesting by Fluorescent Molecules Through Exciplexes for High Efficiency Organic Light-Emitting Diodes," Applied Physics Letters, Apr. 18, 2013, vol. 102, No. 15, pp. 153306-1-153306-5.

International Search Report (Application No. PCT/IB2017/054744) dated Oct. 10, 2017.

Written Opinion (Application No. PCT/IB2017/054744) dated Oct. 10, 2017.

Tamura, S., "Molecular Design," Oyobuturi, Dec. 10, 2000, vol. 69, No. 12, pp. 1456-1461, JSAP (The Japan Society of Applied Physics).

Gong, S. et al., "Tuning the Photophysical Properties and Energy Levels by Linking Spacer and Topology between the Benzimidazole and Carbazole Units: Bipolar Host for Highly Efficient Phosphorescent OLEDs," The Journal of Physical Chemistry C, Mar. 1, 2010, vol. 114, No. 11, pp. 5193-5198, American Chemical Socitey.

Buchtik, R. et al., "Polycyclic Heterocycles with Acidic N-H group VII1 Synthesis of Some Polynuclear Heterocyclic Compounds Derived from 5-phenyl-6-azauracil," ARKIVOC, Apr. 14, 2006, vol. 2006, No. 5, pp. 78-85.

\* cited by examiner

ORGANIC COMPOUND, LIGHT-EMITTING ELEMENT, LIGHT-EMITTING DEVICE, ELECTRONIC DEVICE AND LIGHTING DEVICE

This application is a continuation of copending U.S. application Ser. No. 15/674,943, filed on Aug. 11, 2017 which is incorporated herein by reference.

TECHNICAL FIELD

One embodiment of the present invention relates to a light-emitting element, a light-emitting device, an electronic device, and a lighting device. Note that one embodiment of the present invention is not limited thereto. That is, one embodiment of the present invention relates to an object, a method, a manufacturing method, or a driving method. One embodiment of the present invention relates to a process, a machine, manufacture, or a composition of matter. As specific examples, a semiconductor device, a display device, a liquid crystal display device, and the like can be given.

BACKGROUND ART

A light-emitting element including an EL layer between a pair of electrodes (also referred to as an organic EL element) has characteristics such as thinness, light weight, high-speed response to input signals, and low power consumption; thus, a display including such a light-emitting element has attracted attention as a next-generation flat panel display.

In a light-emitting element, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state (S*) or a triplet excited state (T*). Light emission from a singlet excited state is referred to as fluorescence, and light emission from a triplet excited state is referred to as phosphorescence. The statistical generation ratio of S* to T* in the light-emitting element is considered to be 1:3. Since the spectrum of light emitted from a light-emitting substance depends on the light-emitting substance, the use of different types of organic compounds as light-emitting substances makes it possible to obtain light-emitting elements which exhibit various colors.

In order to improve element characteristics of such a light-emitting element, improvement of an element structure, development of a material, and the like have been actively carried out (see Patent Document 1, for example).

REFERENCE

Patent Document

[Patent Document 1] Japanese Published Patent Application No. 2010-182699

DISCLOSURE OF INVENTION

In development of light-emitting elements, organic compounds used in the light-emitting element are very important for improving the characteristics and reliability. Thus, an object of one embodiment of the present invention is to provide a novel organic compound. That is, a novel organic compound that is effective in improving the element characteristics and reliability is provided. Another object of one embodiment of the present invention is to provide a novel organic compound that can be used in a light-emitting element. Another object of one embodiment of the present invention is to provide a novel organic compound that can be used in an EL layer of a light-emitting element. Another object is to provide a highly efficient, highly reliable, and novel light-emitting element using a novel organic compound of one embodiment of the present invention. Another object is to provide a novel light-emitting device, a novel electronic device, or a novel lighting device. Note that the description of these objects does not preclude the existence of other objects. In one embodiment of the present invention, there is no need to achieve all the objects. Other objects will be apparent from and can be derived from the description of the specification, the drawings, the claims, and the like.

One embodiment of the present invention is an organic compound represented by General Formula (G1).

[Chemical formula 1]

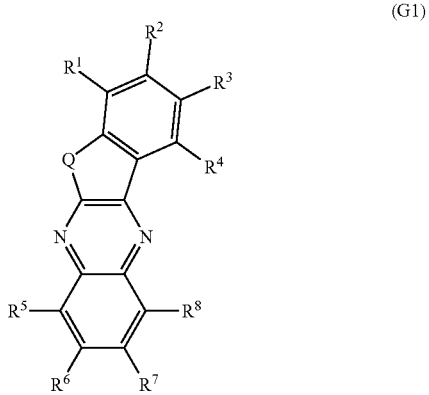

In General Formula (G1), Q represents O or S, and each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. At least one of $R^1$ to $R^8$ includes a substituted or unsubstituted condensed aromatic or heteroaromatic ring having 3 to 24 carbon atoms.

Another embodiment of the present invention is an organic compound represented by General Formula (G1).

[Chemical Formula 2]

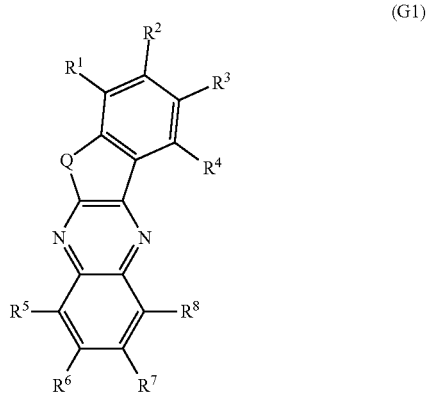

In General Formula (G1), Q represents O or S, and each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. At least one of $R^1$ to $R^4$ and at least one of $R^5$ to $R^8$ each include a substituted or unsubstituted condensed aromatic or heteroaromatic ring having 3 to 24 carbon atoms.

In each of the above structures, the condensed aromatic ring or the condensed heteroaromatic ring can be any of a naphthalene ring, a fluorene ring, a phenanthrene ring, a triphenylene ring, a dibenzothiophene ring, a dibenzofuran ring, and a carbazole ring.

Another embodiment of the present invention is an organic compound represented by General Formula (G1).

[Chemical Formula 3]

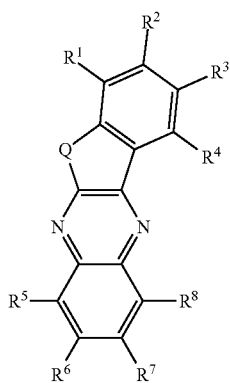

(G1)

In General Formula (G1), Q represents O or S, and each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. At least one of $R^1$ to $R^8$ includes A represented by any of General Formulae (A-1) to (A-4), via a substituted or unsubstituted arylene group having 6 to 24 carbon atoms or a substituted or unsubstituted heteroarylene group having 3 to 24 carbon atoms.

[Chemical Formulae 4]

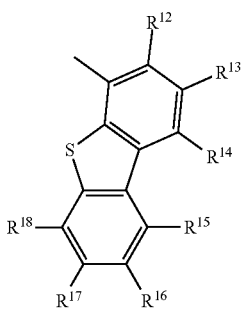

(A-1)

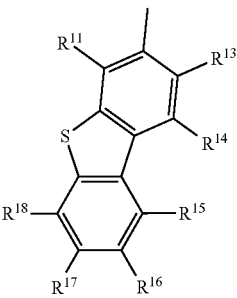

(A-2)

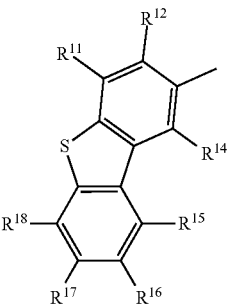

(A-3)

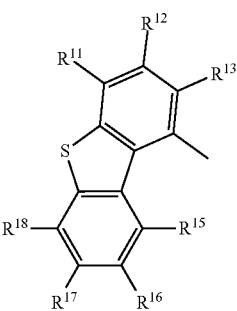

(A-4)

In General Formulae (A-1) to (A-4), each of $R^{11}$ to $R^{18}$ independently represents any of hydrogen, an alkyl group having 1 to 6 carbon atoms, and a substituted or unsubstituted phenyl group.

Another embodiment of the present invention is an organic compound represented by General Formula (G1).

[Chemical Formula 5]

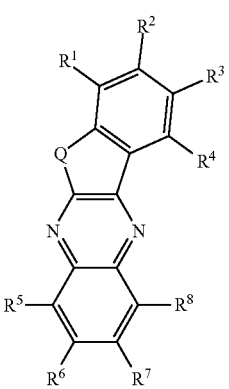

(G1)

In General Formula (G1), Q represents O or S, and each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. At least one of $R^1$ to $R^4$ and at least one of $R^5$ to $R^8$ each include A represented by any of General Formulae (A-1) to (A-4), via a substituted or unsubstituted arylene group having 6 to 24 carbon atoms or a substituted or unsubstituted heteroarylene group having 3 to 24 carbon atoms.

One embodiment of the present invention also includes a structure in which A is directly bonded to at least one of $R^1$ to $R^8$ or each of at least one of $R^1$ to $R^4$ and at least one of $R^5$ to $R^8$ in any of the above structures.

In any of the above structures, A included in General Formula (G1) also includes a structure represented by any of General Formulae (A-5) to (A-13).

[Chemical Formulae 6]

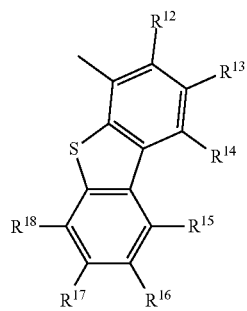

(A-1)

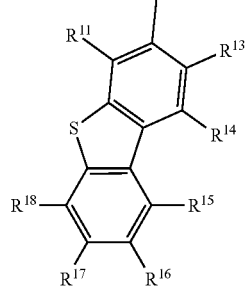

(A-2)

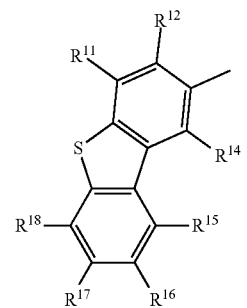

(A-3)

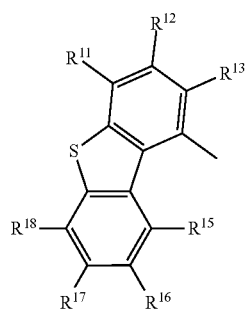

(A-4)

In General Formulae (A-1) to (A-4), each of $R^{11}$ to $R^{18}$ independently represents any of hydrogen, an alkyl group having 1 to 6 carbon atoms, and a substituted or unsubstituted phenyl group.

[Chemical Formulae 7]

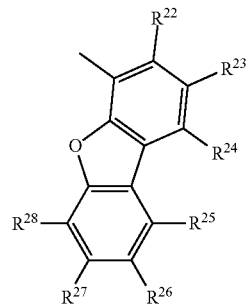

(A-5)

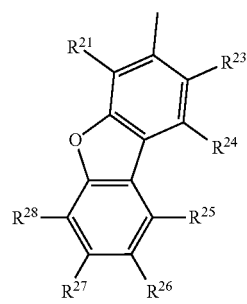

(A-6)

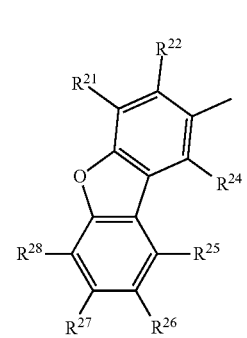

(A-7)

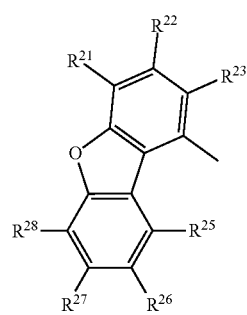

(A-8)

-continued

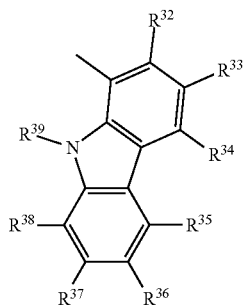
(A-9)

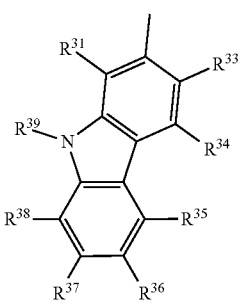
(A-10)

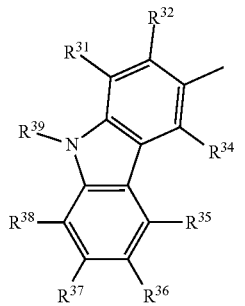
(A-11)

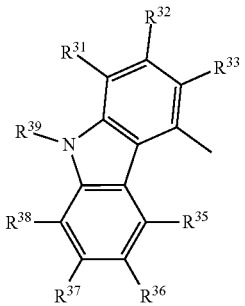
(A-12)

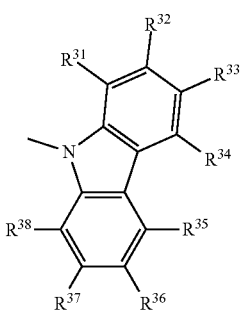
(A-13)

In General Formulae (A-5) to (A-13), each of $R^{21}$ to $R^{28}$ and $R^{31}$ to $R^{39}$ independently represents any of hydrogen, an alkyl group having 1 to 6 carbon atoms, and a substituted or unsubstituted phenyl group.

Another embodiment of the present invention is an organic compound represented by Structural Formula (100), Structural Formula (200), or Structural Formula (262).

[Chemical Formulae 8]

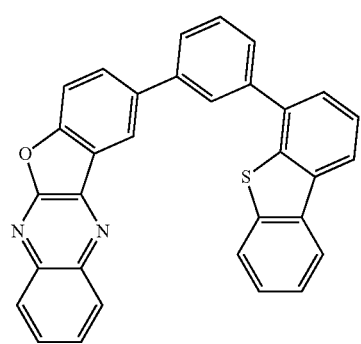
(100)

-continued

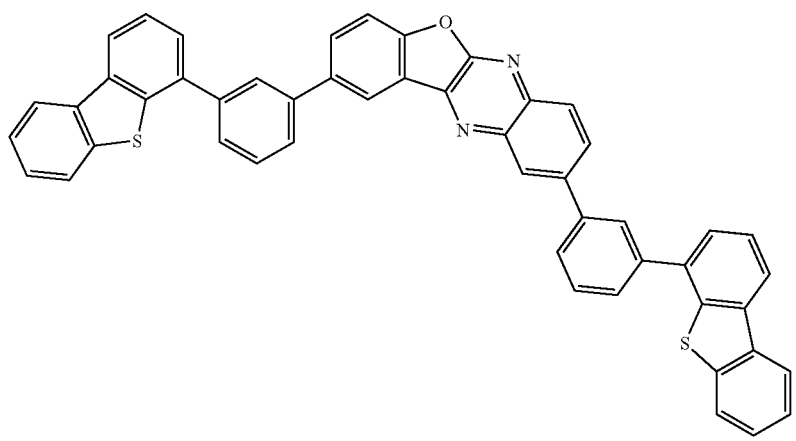
(200)

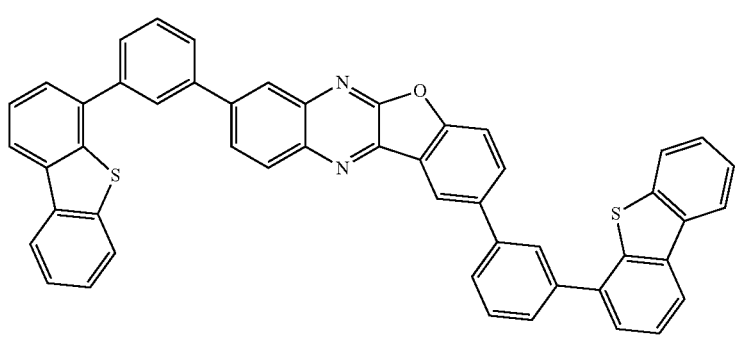
(262)

Another embodiment of the present invention is a light-emitting element containing an organic compound having a benzofuroquinoxaline skeleton or a benzothienoquinoxaline skeleton. One embodiment of the present invention also includes a light-emitting element containing the above organic compound and a substance that converts triplet excitation energy into light emission, such as a phosphorescence material including an organometallic complex or a TADF material.

Another embodiment of the present invention is a light-emitting element containing the organic compound of one embodiment of the present invention. Note that one embodiment of the present invention also includes a light-emitting element in which an EL layer provided between a pair of electrodes or a light-emitting layer included in the EL layer contains the organic compound of one embodiment of the present invention. In addition to the above light-emitting elements, a light-emitting device including a transistor, a substrate, or the like is also included in the scope of the invention. Furthermore, in addition to the light-emitting device, an electronic device and a lighting device that include a microphone, a camera, an operation button, an external connection portion, a housing, a cover, a support, a speaker, or the like are also included in the scope of the invention.

The organic compound of one embodiment of the present invention can be used as a light-emitting substance. Alternatively, the organic compound of one embodiment of the present invention can be used in combination with a light-emitting substance that emits phosphorescence (phosphorescent compound) for a light-emitting layer of a light-emitting element. That is, light emission from a triplet excited state can be obtained from the light-emitting layer; thus, the efficiency of the light-emitting element can be improved, which is very effective. Accordingly, one embodiment of the present invention also includes a light-emitting element in which the organic compound of one embodiment of the present invention and a phosphorescent compound are used in combination in a light-emitting layer. A structure in which the light-emitting layer further contains a third substance may also be employed.

One embodiment of the present invention includes, in its category, a light-emitting device including a light-emitting element, and a lighting device including the light-emitting element. Accordingly, a light-emitting device in this specification means an image display device or a light source (including a lighting device). Furthermore, a light-emitting device includes the following modules in its category: a module in which a connector such as a flexible printed circuit (FPC) or a tape carrier package (TCP) is attached to a light-emitting device; a module having a TCP whose end is provided with a printed wiring board; and a module in which an integrated circuit (IC) is directly mounted on a light-emitting element by a chip on glass (COG) method.

According to one embodiment of the present invention, a novel organic compound can be provided. In other words, a novel organic compound that is effective in improving the element characteristics and reliability can be provided. According to one embodiment of the present invention, a novel organic compound that can be used in a light-emitting element can be provided. According to one embodiment of the present invention, a novel organic compound that can be used in an EL layer of a light-emitting element can be provided. According to one embodiment of the present invention, a highly efficient, highly reliable, and novel light-emitting element using a novel organic compound of one embodiment of the present invention can be provided. In addition, a novel light-emitting device, a novel electronic device, or a novel lighting device can be provided. Note that the description of these effects does not preclude the existence of other effects. One embodiment of the present invention does not necessarily have all the effects listed above. Other effects will be apparent from and can be derived from the description of the specification, the drawings, the claims, and the like.

BRIEF DESCRIPTION OF DRAWINGS

FIGS. 14A, 14B1, and 14B2 are block diagrams of display devices.

BEST MODE FOR CARRYING OUT THE INVENTION

Figure 1A:
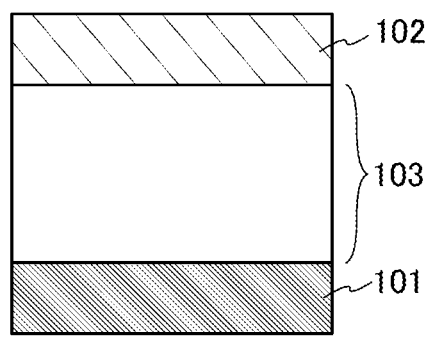
FIGS. 1A to 1D each illustrate a structure of a light-emitting element.

Embodiments of the present invention will be described in detail below with reference to the drawings. However, the present invention is not limited to the following description, and the mode and details can be variously changed unless departing from the scope and spirit of the present invention. Thus, the present invention should not be construed as being limited to the description in the following embodiments.

Note that the position, the size, the range, or the like of each component illustrated in the drawings and the like are not accurately represented in some cases for easy understanding. Therefore, the disclosed invention is not necessarily limited to the position, size, range, or the like as disclosed in the drawings and the like.

In the description of structures of the present invention in this specification and the like with reference to the drawings, the same components in different drawings are denoted by the same reference numeral.

Embodiment 1

In this embodiment, an organic compound of one embodiment of the present invention will be described.

The organic compound of one embodiment of the present invention has a structure represented by General Formula (G1) having a benzofuroquinoxaline skeleton or a benzothienoquinoxaline skeleton.

[Chemical Formula 9]

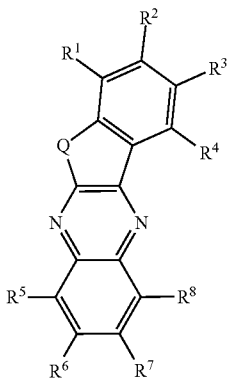
(G1)

In General Formula (G1), Q represents O or S, and each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. At least one of $R^1$ to $R^8$ includes a substituted or unsubstituted condensed aromatic or heteroaromatic ring having 3 to 24 carbon atoms.

Alternatively, in General Formula (G1), Q represents O or S, and each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. At least one of $R^1$ to $R^4$ and at least one of $R^5$ to $R^8$ each include a substituted or unsubstituted condensed aromatic or heteroaromatic ring having 3 to 24 carbon atoms.

Further alternatively, in General Formula (G1), Q represents O or S, and each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. At least one of $R^1$ to $R^8$ includes A represented by any of General Formulae (A-1) to (A-4), via a substituted or unsubstituted arylene group having 6 to 24 carbon atoms or a substituted or unsubstituted heteroarylene group having 3 to 24 carbon atoms.

[Chemical Formulae 10]

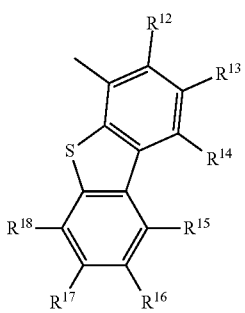
(A-1)

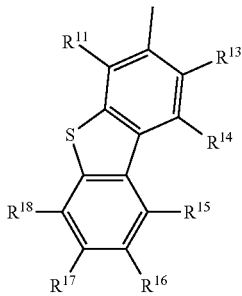
(A-2)

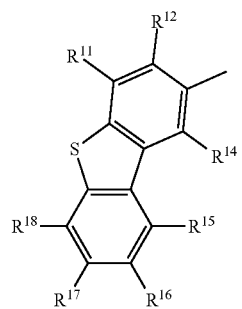
(A-3)

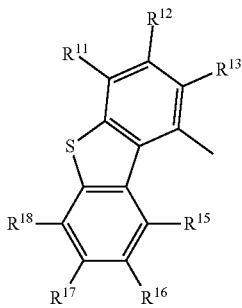
(A-4)

In General Formulae (A-1) to (A-4), each of $R^{11}$ to $R^{18}$ independently represents any of hydrogen, an alkyl group having 1 to 6 carbon atoms, and a substituted or unsubstituted phenyl group.

Further alternatively, in General Formula (G1), Q represents O or S, and each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. At least one of $R^1$ to $R^4$ and at least one of $R^5$ to $R^8$ each include A represented by any of General Formulae (A-1) to (A-4), via a substituted or unsubstituted arylene group having 6 to 24 carbon atoms or a substituted or unsubstituted heteroarylene group having 3 to 24 carbon atoms.

[Chemical Formulae 11]

(A-1)
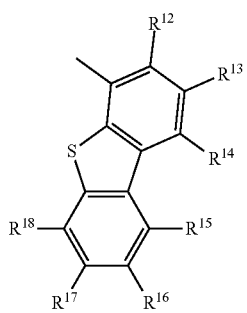

(A-2)
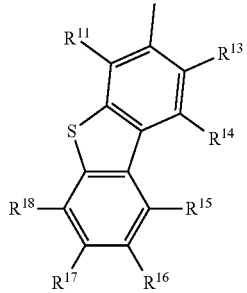

(A-3)
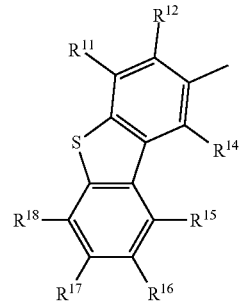

(A-4)
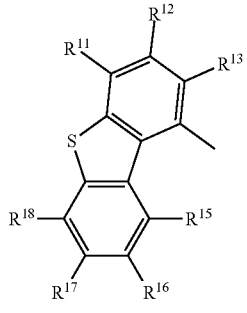

In General Formulae (A-1) to (A-4), each of $R^{11}$ to $R^{18}$ independently represents any of hydrogen, an alkyl group having 1 to 6 carbon atoms, and a substituted or unsubstituted phenyl group.

In each of the structures represented by General Formula (G1), A may be directly bonded to at least one of $R^1$ to $R^8$ or each of at least one of $R^1$ to $R^4$ and at least one of $R^5$ to $R^8$.

In each of the above structures, A included in General Formula (G1) also includes a structure represented by any of General Formulae (A-5) to (A-13).

[Chemical Formulae 12]

(A-5)
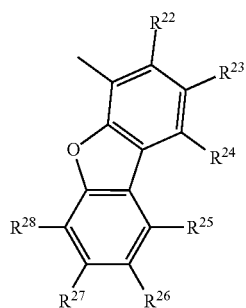

(A-6)
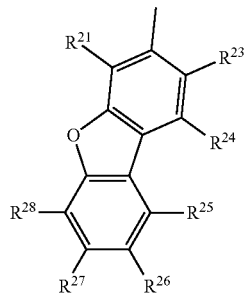

(A-7)
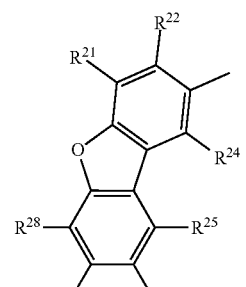

(A-8)
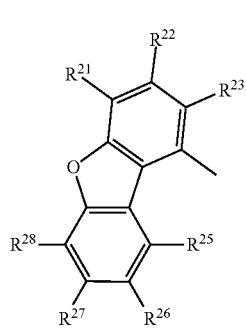

(A-9)
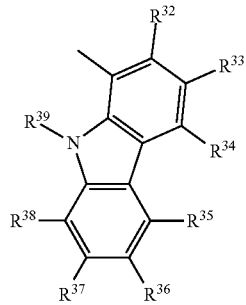

-continued (A-10)

(A-11)

(A-12)

(A-13)

In General Formulae (A-5) to (A-13), each of R to $R^{28}$ and $R^{31}$ to $R^{39}$ independently represents any of hydrogen, an alkyl group having 1 to 6 carbon atoms, and a substituted or unsubstituted phenyl group.

Note that substitution in each of the above structures is preferably substitution of a substituent such as an alkyl group having 1 to 6 carbon atoms, e.g., a methyl group, an ethyl group, an n-propyl group, an isopropyl group, a sec-butyl group, a tert-butyl group, an n-pentyl group, or an n-hexyl group, or substitution of a substituent such as an aryl group having 6 to 12 carbon atoms, e.g., a phenyl group, an o-tolyl group, an m-tolyl group, a p-tolyl group, a 1-naphthyl group, a 2-naphthyl group, a 2-biphenyl group, a 3-biphenyl group, or a 4-biphenyl group. These substituents may be bonded to each other to form a ring. For example, in the case where the arylene group is a 2,7-fluorenylene group having two phenyl groups as substituents at the 9-position, the phenyl groups may be bonded to each other to form a spiro-9,9'-bifluorene-2,7-diyl group.

Specific examples of the alkyl group having 1 to 6 carbon atoms, which is represented by any of $R^1$ to $R^8$ in General Formula (G1), include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

Specific examples of the substituted or unsubstituted aryl group having 6 to 12 carbon atoms, which is represented by any of $R^1$ to $R^8$ in General Formula (G1), include a substituted or unsubstituted phenyl group, a substituted or unsubstituted biphenyl group, a substituted or unsubstituted naphthyl group, and a substituted or unsubstituted indenyl group. Note that substitution in the above is preferably substitution of a substituent such as an alkyl group having 1 to 6 carbon atoms, e.g., a methyl group, an ethyl group, an n-propyl group, an isopropyl group, a sec-butyl group, a tert-butyl group, an n-pentyl group, or an n-hexyl group, or substitution of a substituent such as an aryl group having 6 to 12 carbon atoms, e.g., a phenyl group, an o-tolyl group, an m-tolyl group, a p-tolyl group, a 1-naphthyl group, a 2-naphthyl group, a 2-biphenyl group, a 3-biphenyl group, or a 4-biphenyl group. These substituents may be bonded to each other to form a ring. For example, in the case where the aryl group is a 2-fluorenyl group having two phenyl groups as substituents at the 9-position, the phenyl groups may be bonded to each other to form a spiro-9,9'-bifluoren-2-yl group. More specifically, a phenyl group, a tolyl group, a xylyl group, a biphenyl group, an indenyl group, a naphthyl group, a fluorenyl group, and the like can be given.

Specific examples of the substituted or unsubstituted heteroaryl group having 3 to 12 carbon atoms, which is represented by any of $R^1$ to $R^8$ in General Formula (G1), include a benzothienyl group, a benzofuranyl group, an indolyl group, a dibenzothienyl group, a dibenzofuranyl group, and a carbazolyl group.

Specific examples of the substituted or unsubstituted condensed aromatic or heteroaromatic ring having 3 to 24 carbon atoms, which is represented by any of $R^1$ to $R^8$ in General Formula (G1), include a naphthalene ring, a benzothiophene ring, a benzofuran ring, an indole ring, a fluorene ring, a phenanthrene ring, a triphenylene ring, a dibenzothiophene ring, a benzonaphthothiophene ring, a dibenzofuran ring, a benzonaphthofuran ring, a carbazole ring, and a benzocarbazole ring.

Specific structural formulae of the organic compounds of embodiments of the present invention are shown below. Note that the present invention is not limited thereto.

[Chemical Formulae 13]
(100)
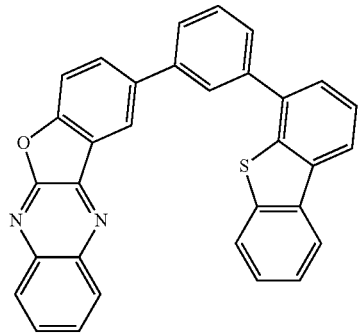
(101)
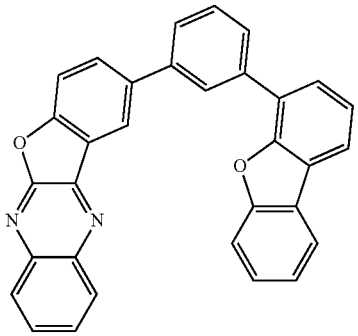
(102)
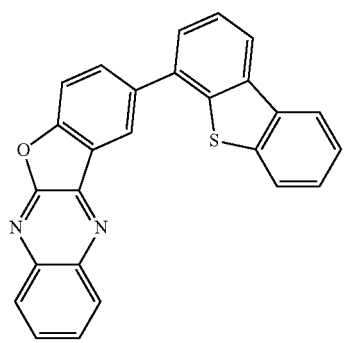
(103)
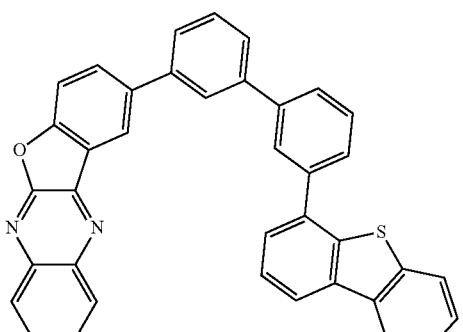
(104)
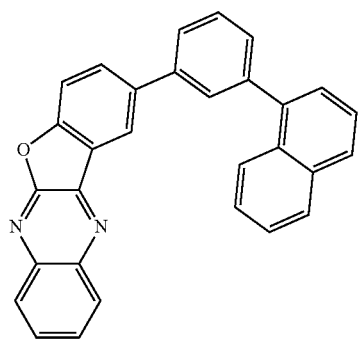
(105)
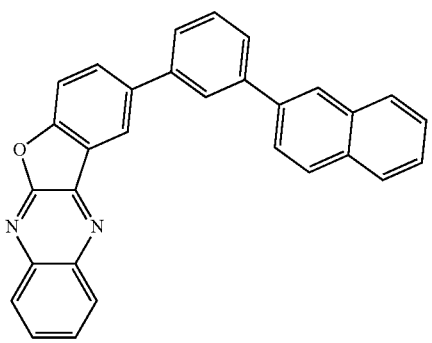
(106)
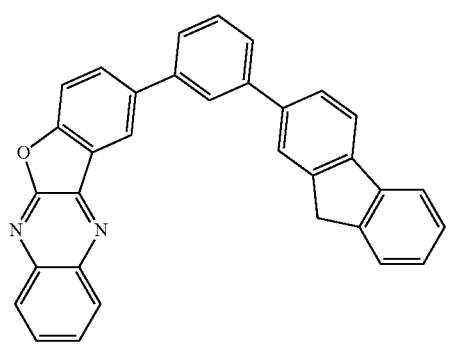
(107)
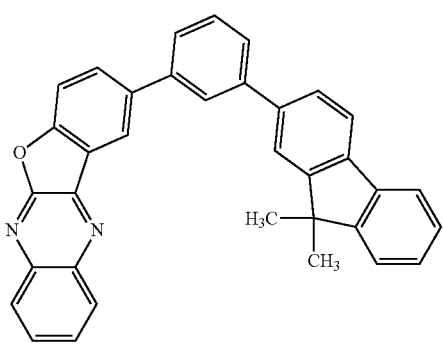

-continued
(108)
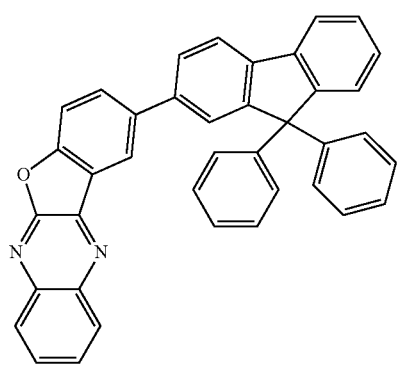
(109)
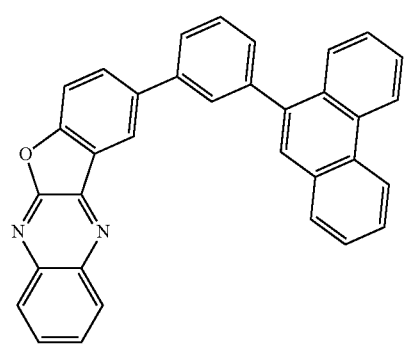
(110)
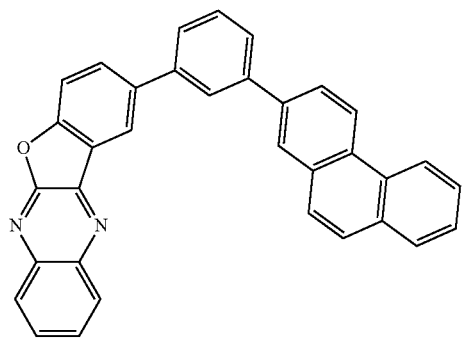
(111)
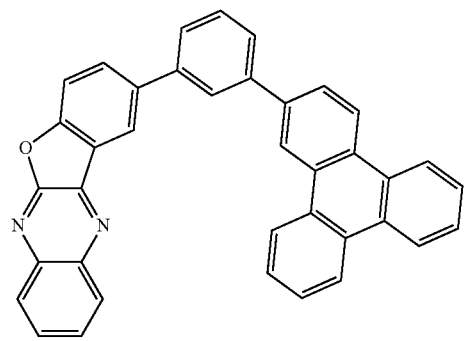
(112)
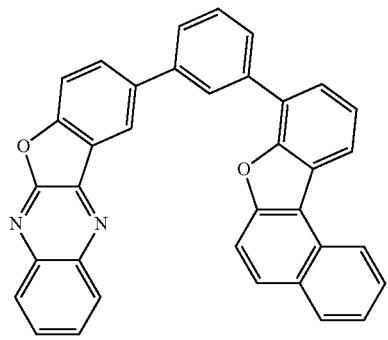
(113)
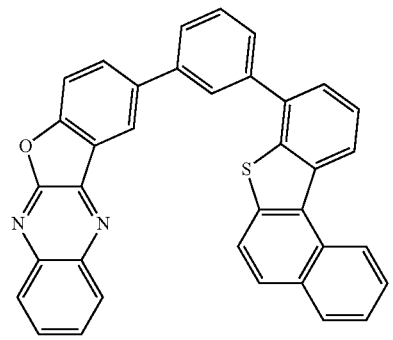
(114)
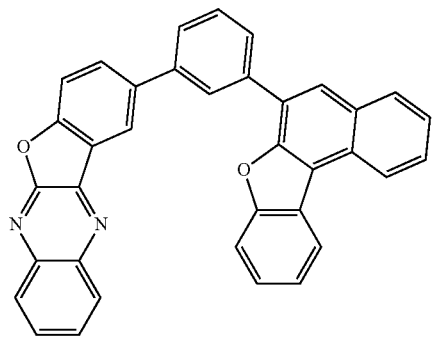

[Chemical Formulae 14]
(115)
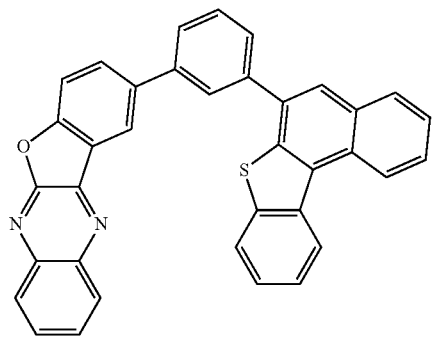
(116)
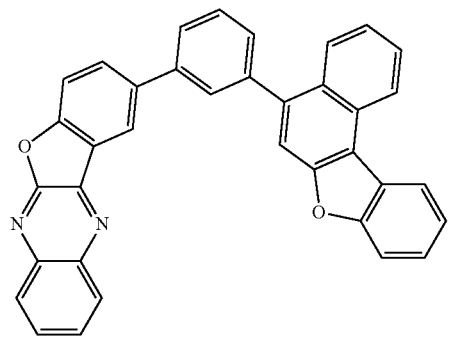
(117)
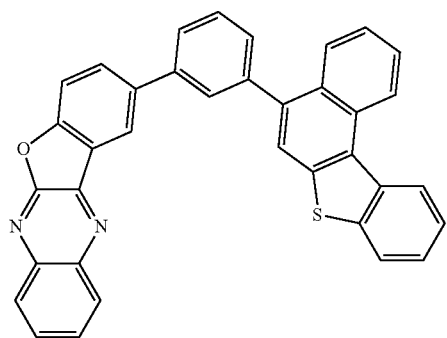
(118)
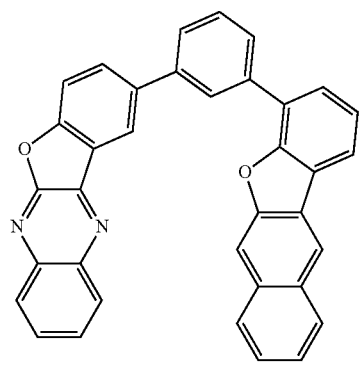
(119)
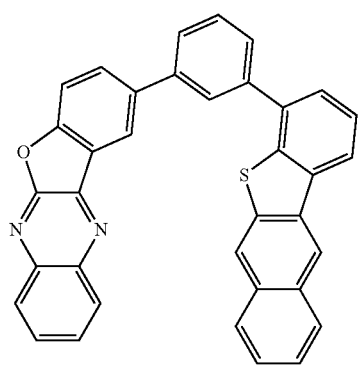
(120)
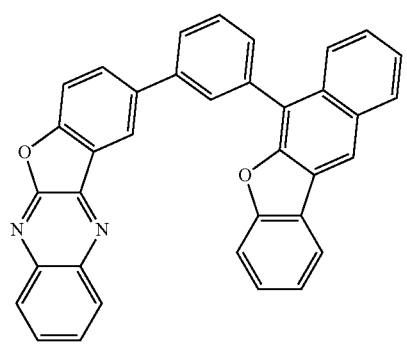
(121)
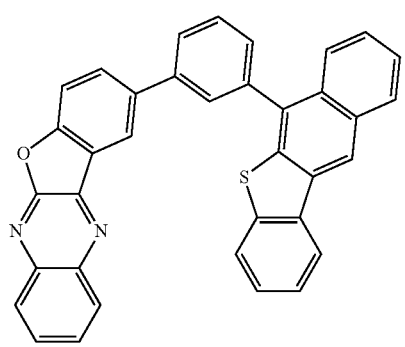
(122)
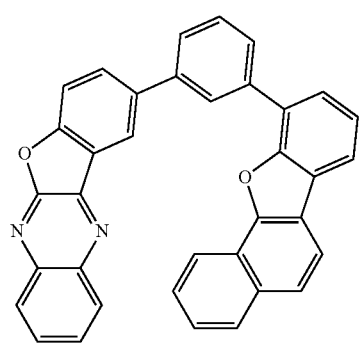

-continued
(123)
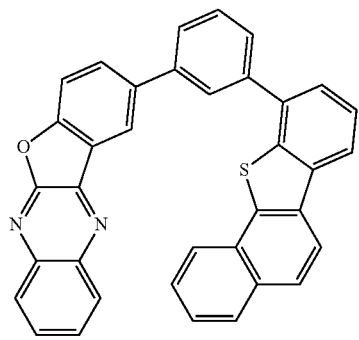
(124)
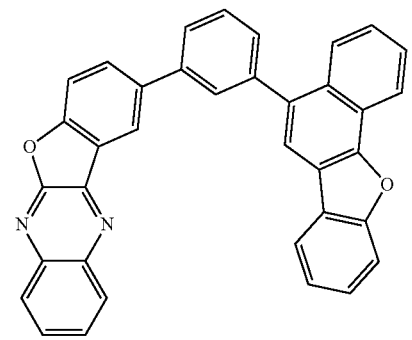
(125)
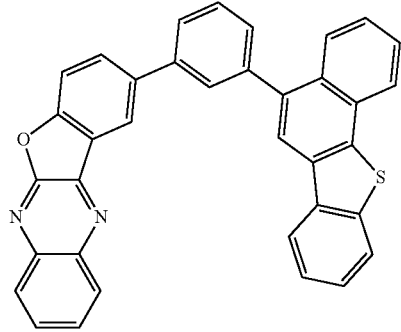
(126)
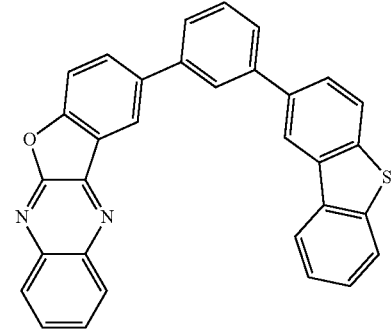
(127)
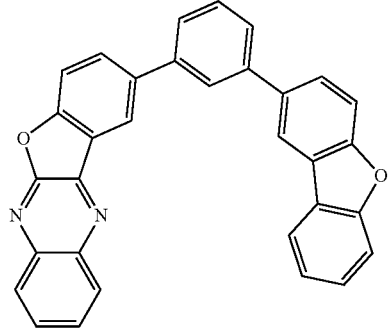
(128)
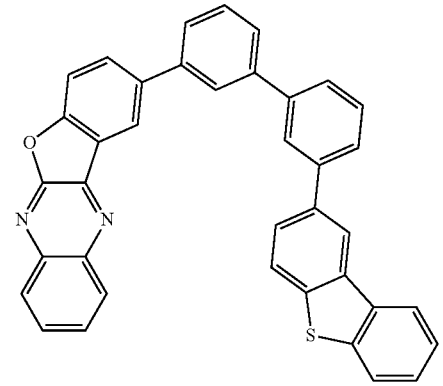
(129)
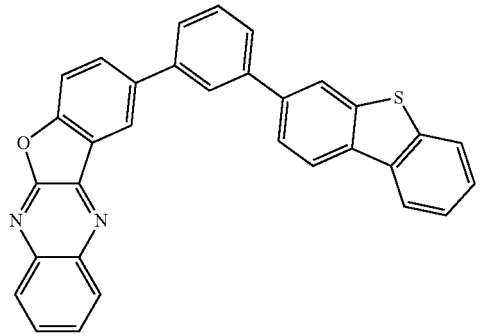

[Chemical Formulae 15]
(130)
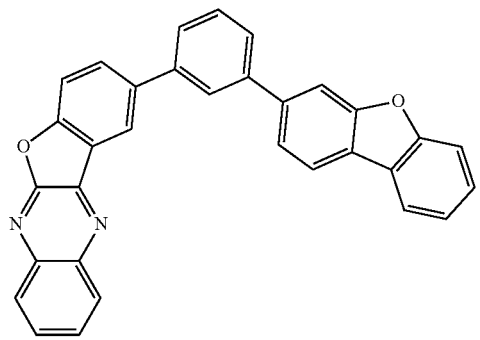
(131)
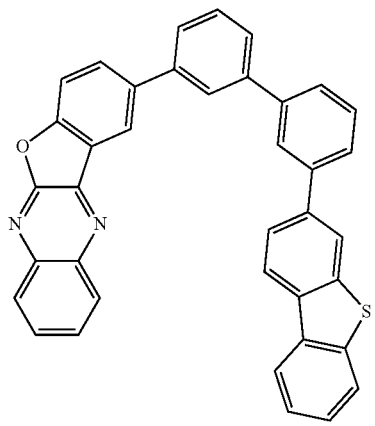
(132)
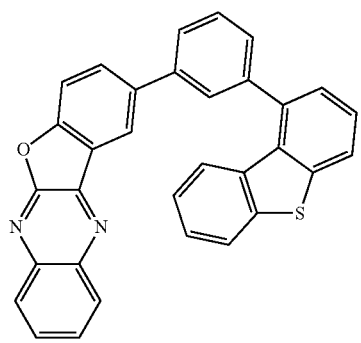
(133)
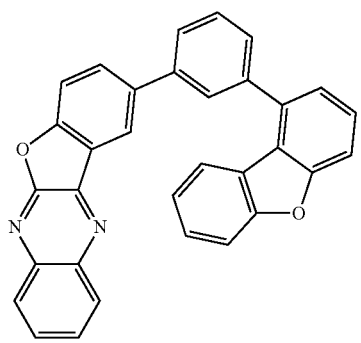
(134)
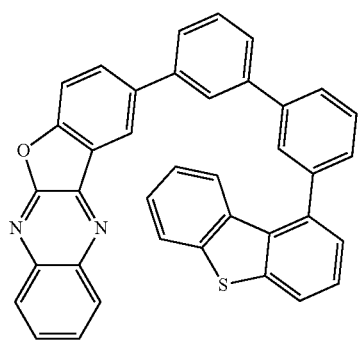
(135)
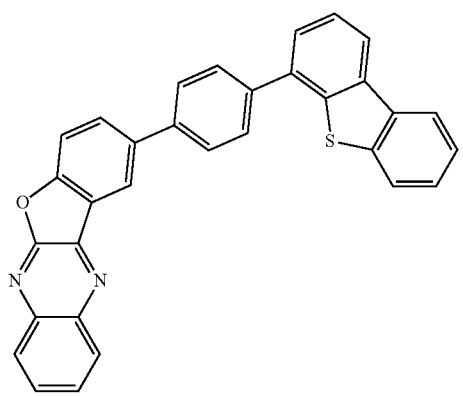
(136)
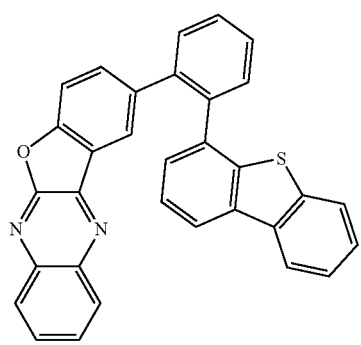
(137)
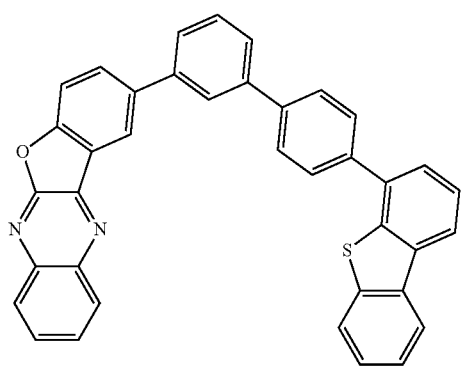

-continued
(138)
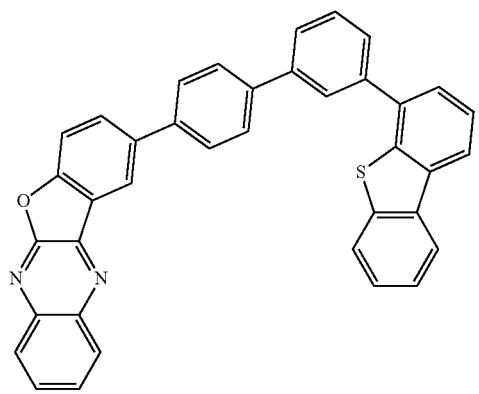
(139)
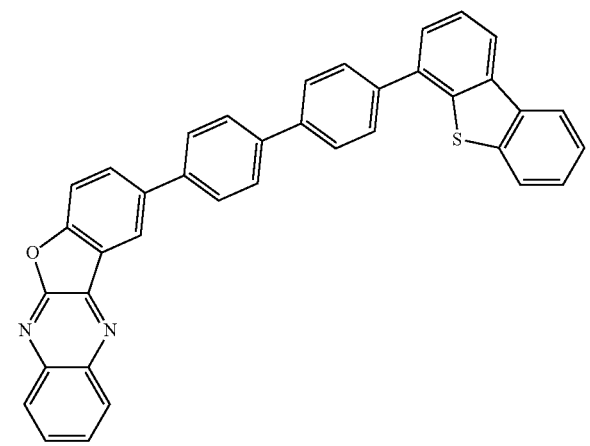
(140)
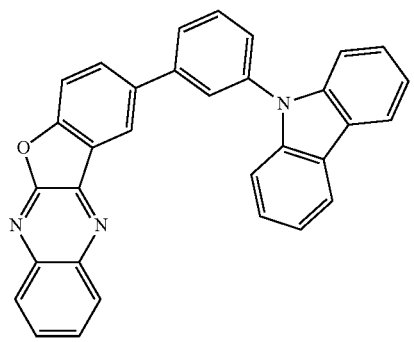
(141)
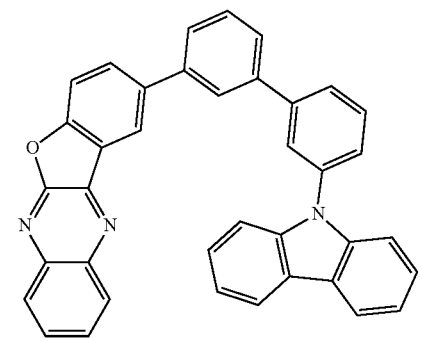
(142)
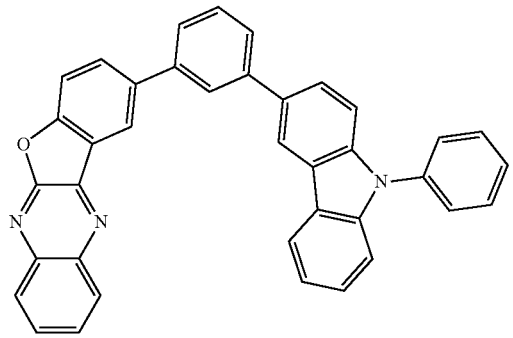
(143)
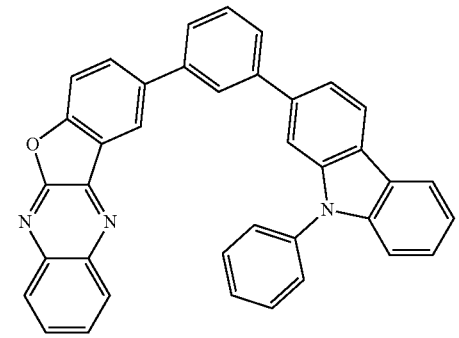
(144)
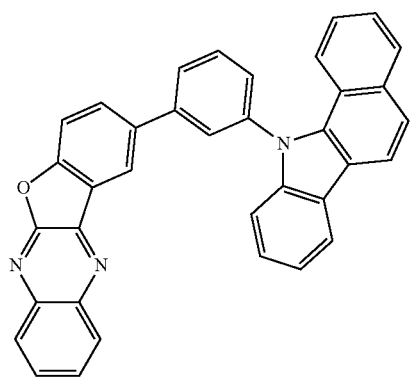

[Chemical Formulae 16]
(145)
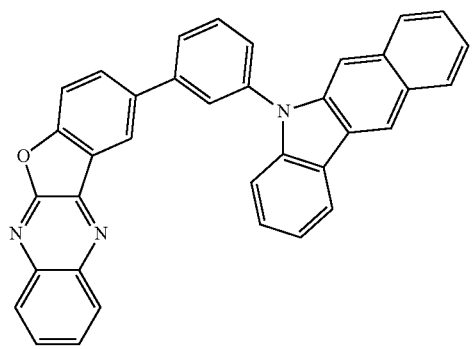
(146)
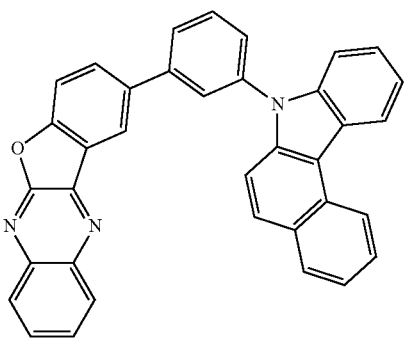
(147)
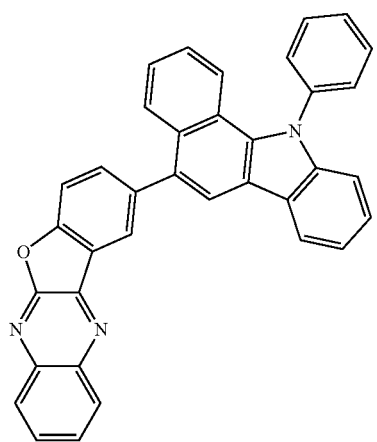
(148)
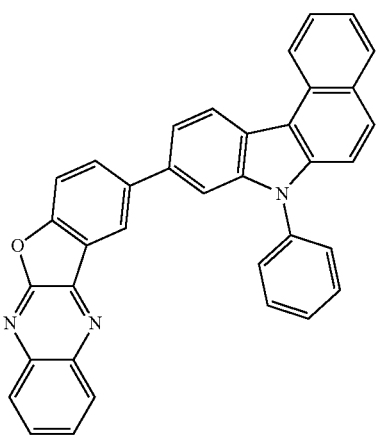
(149)
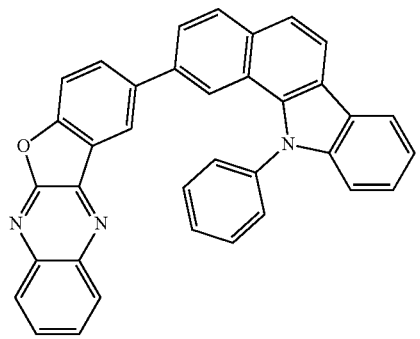
(150)
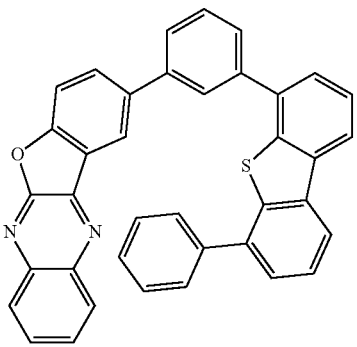
(151)
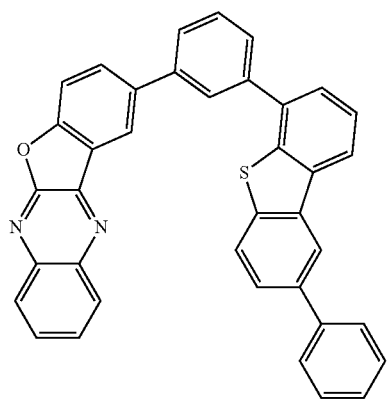
(152)
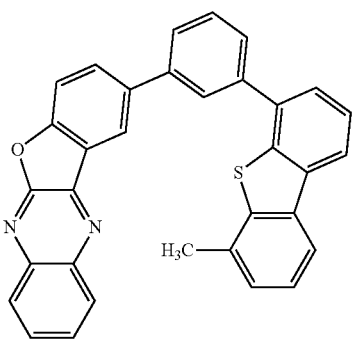

-continued
(153)
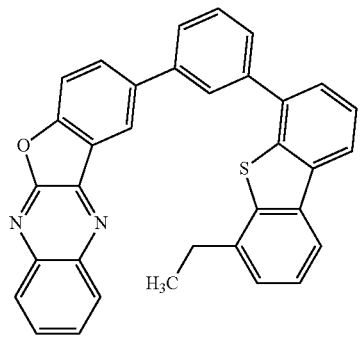
(154)
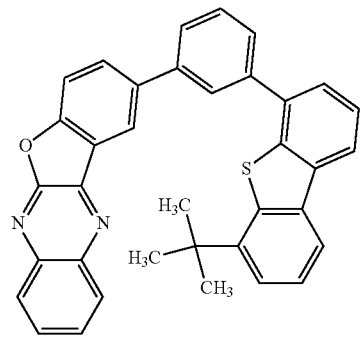
(155)
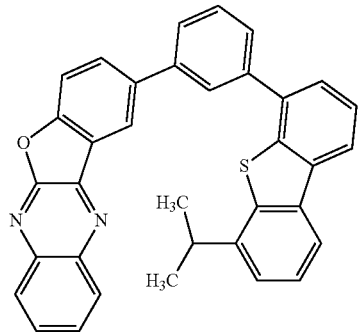
(156)
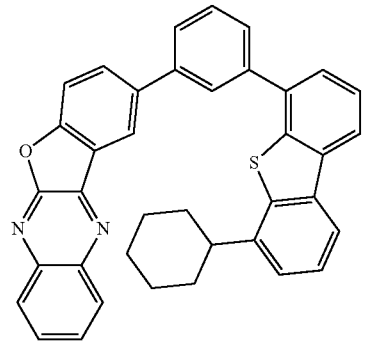
(157)
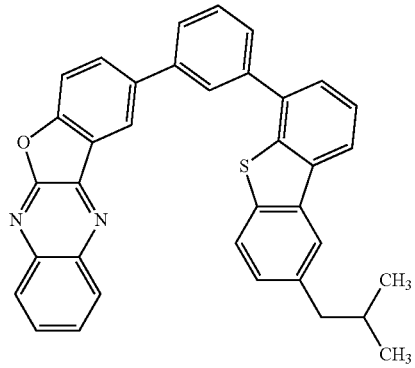
(158)
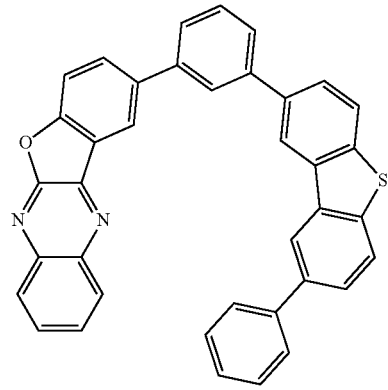
(159)
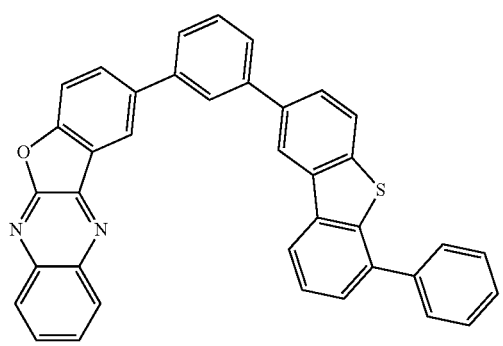

[Chemical Formulae 17]
(160)
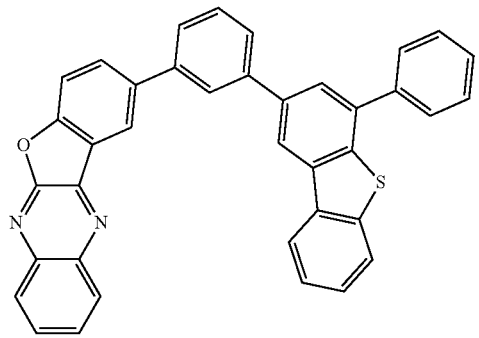
(161)
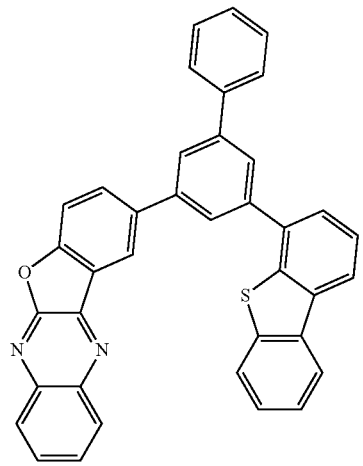
(162)
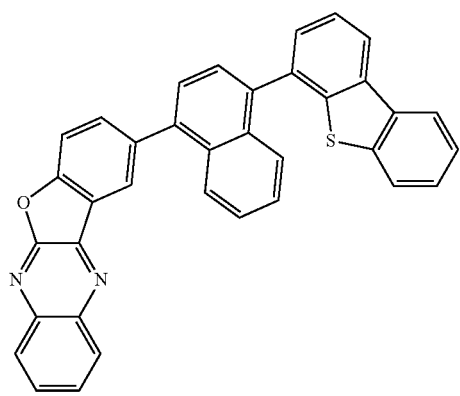
(163)
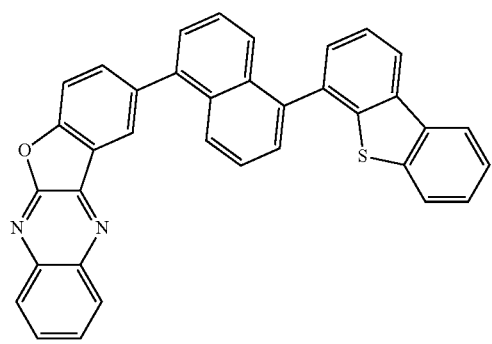
(164)
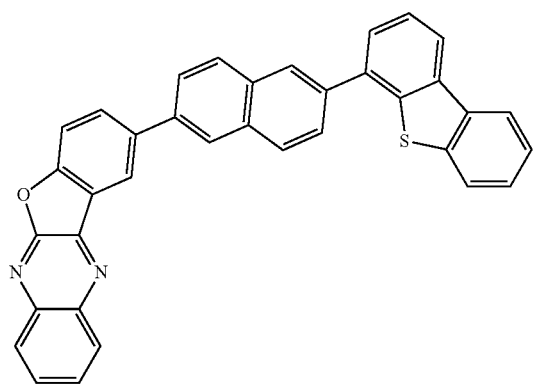
(165)
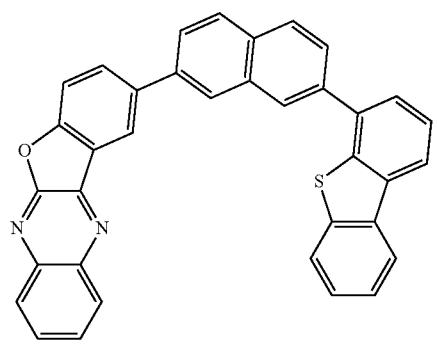

-continued
(166)
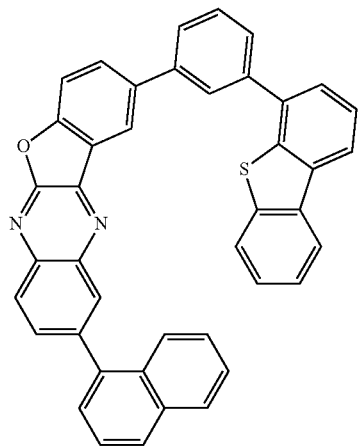
(167)
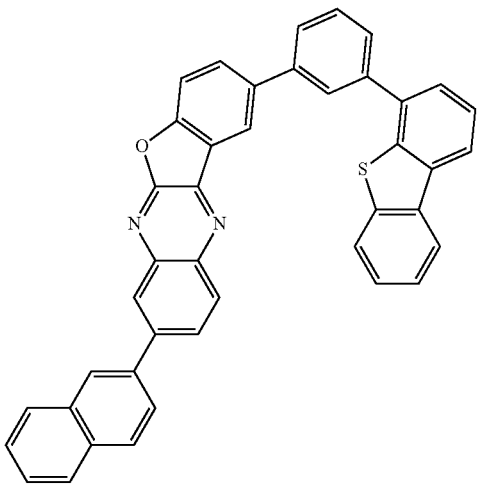
(168)
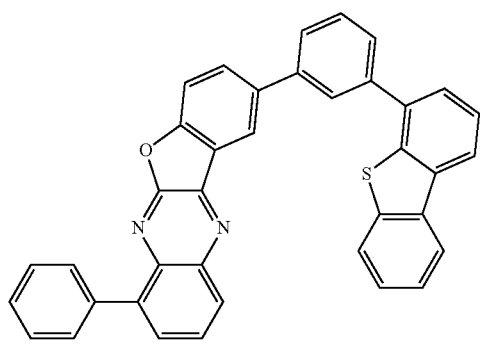
(169)
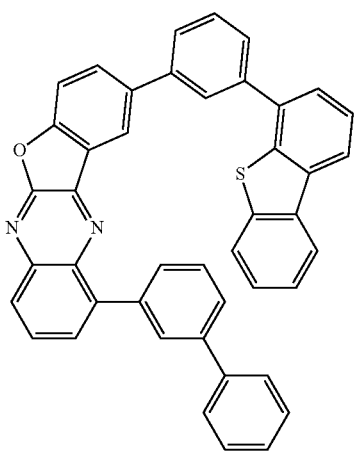
(170)
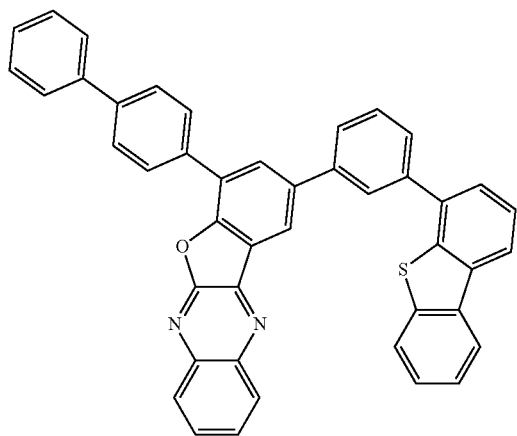
(171)
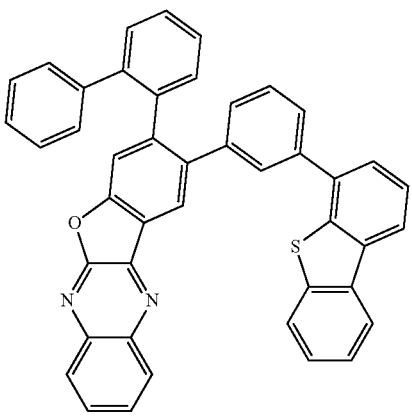

(172)
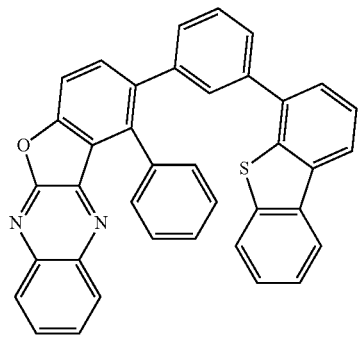
(173)
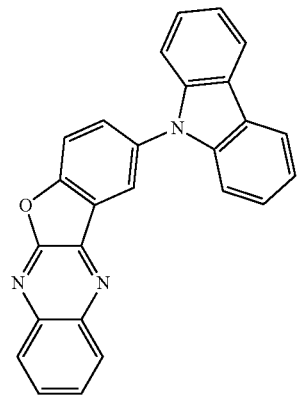
(174)
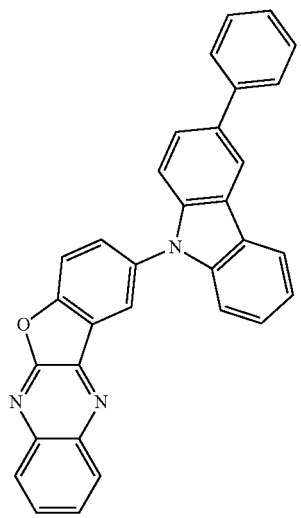
[Chemical Formulae 18]
(175)
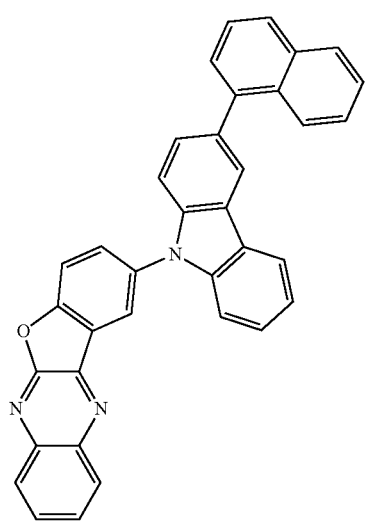
(176)
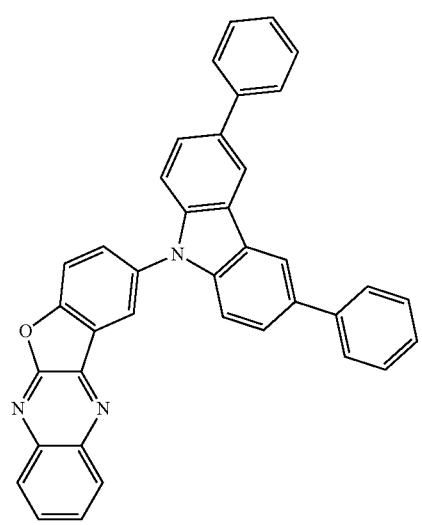

-continued
(177)
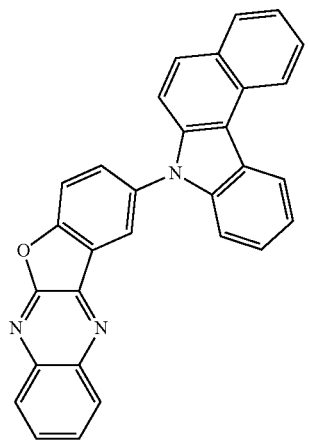
(178)
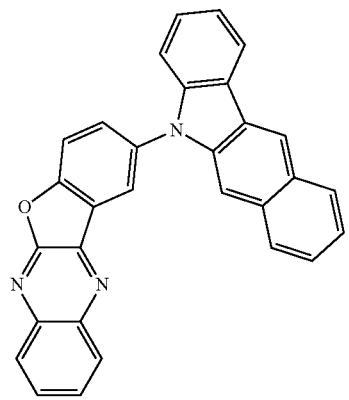
(179)
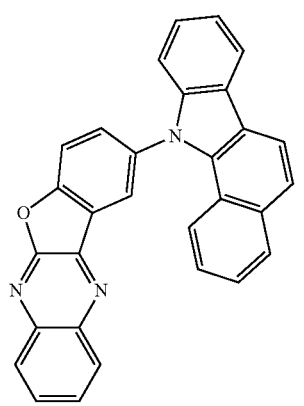
(180)
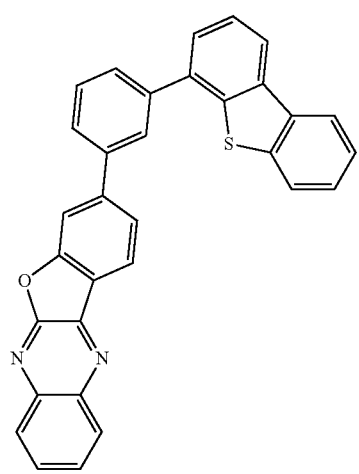
(181)
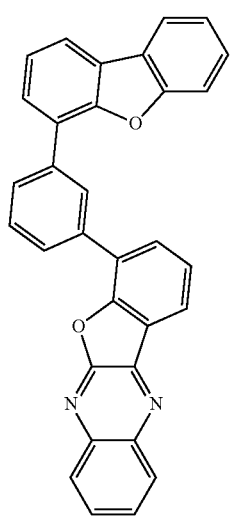
(182)
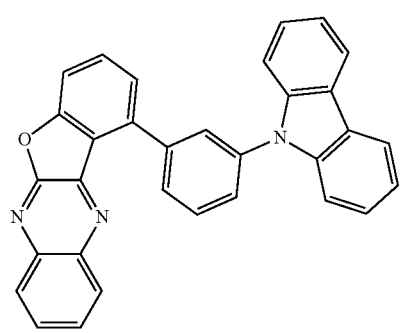

(183)
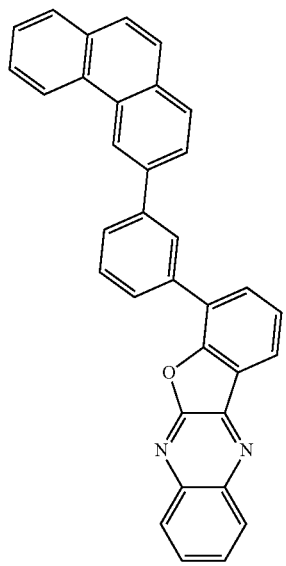
(184)
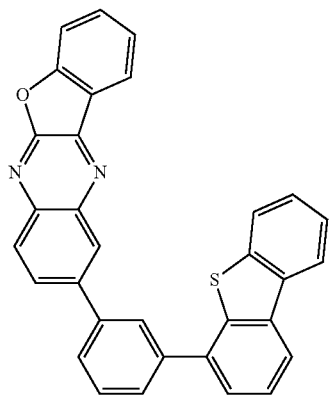
(185)
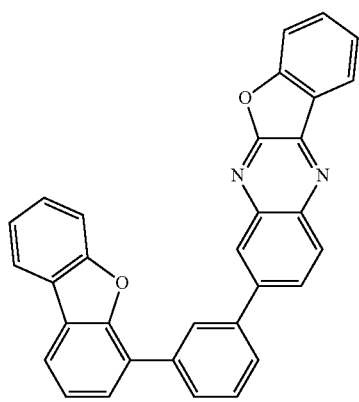
(186)
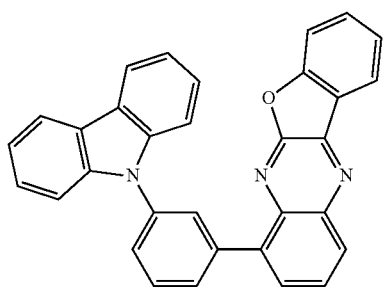
[Chemical Formulae 19]
(187)
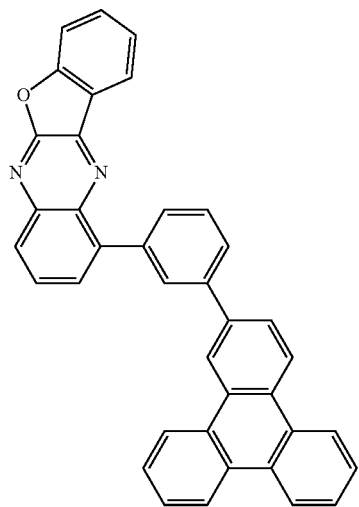
(188)
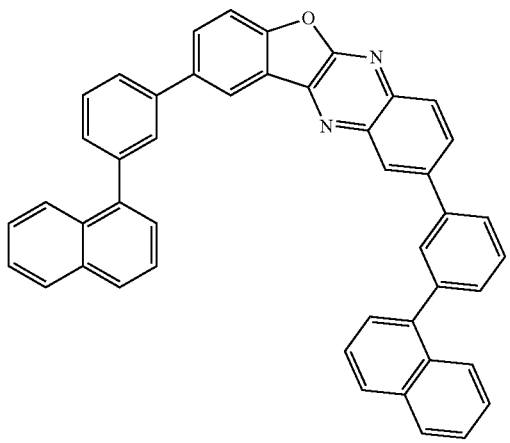

-continued
(189)
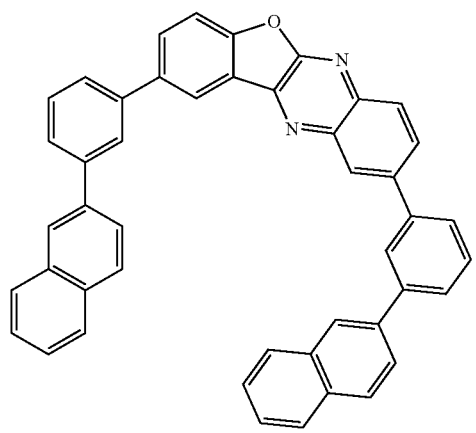
(190)
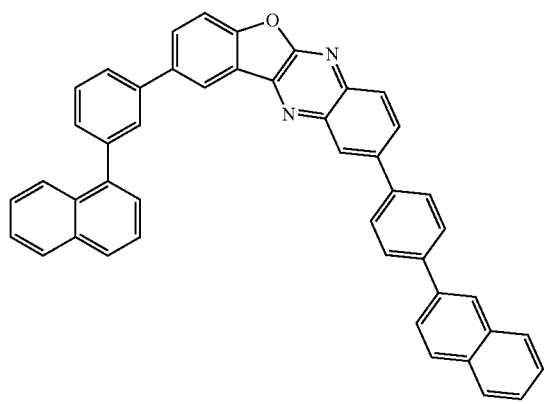
(191)
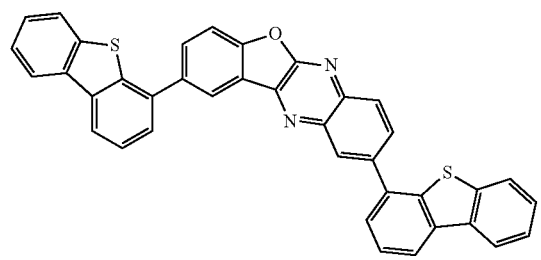
(192)
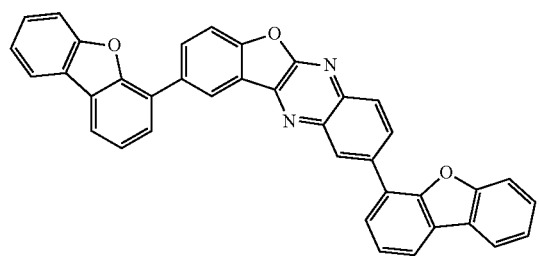
(193)
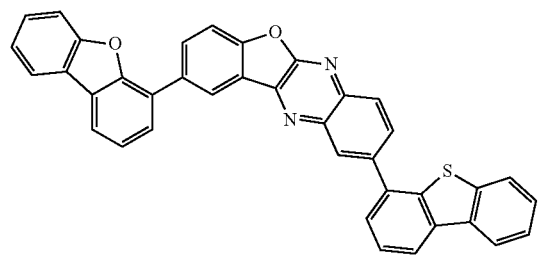
(194)
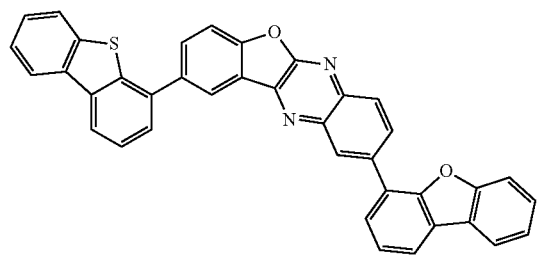
(195)
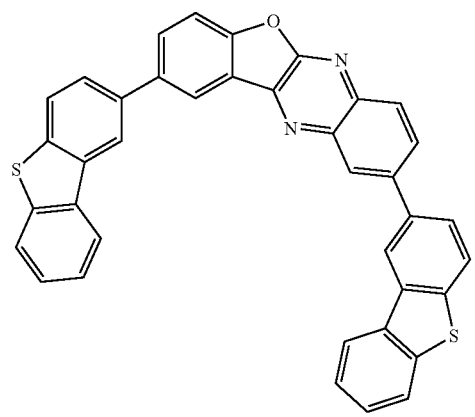
(196)
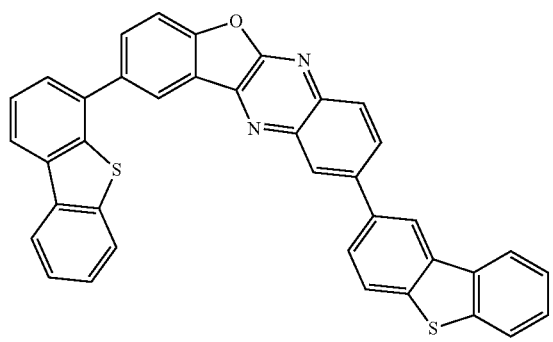

-continued
(197)
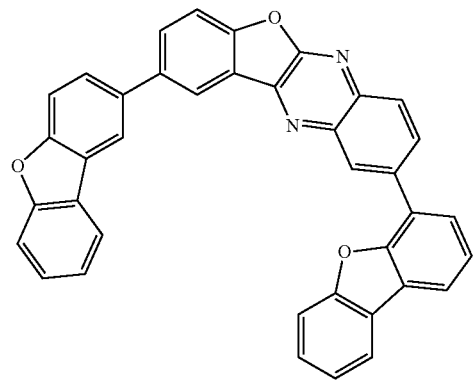
(198)
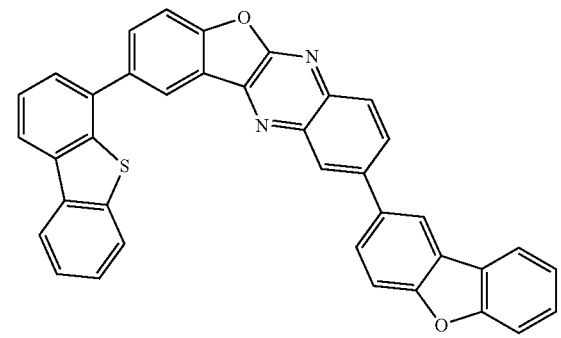
(199)
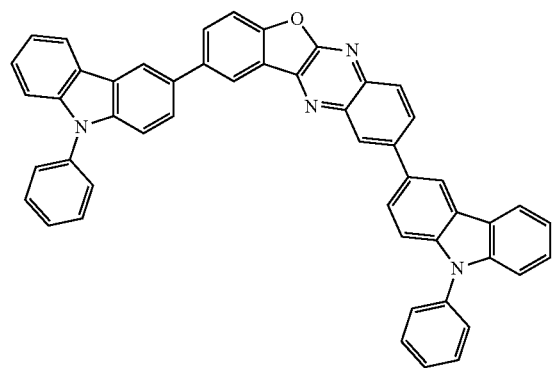
(200)
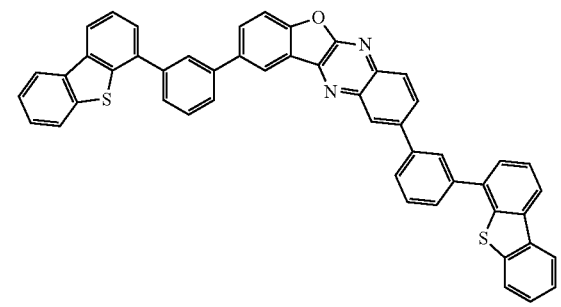
[Chemical Formulae 20]
(201)
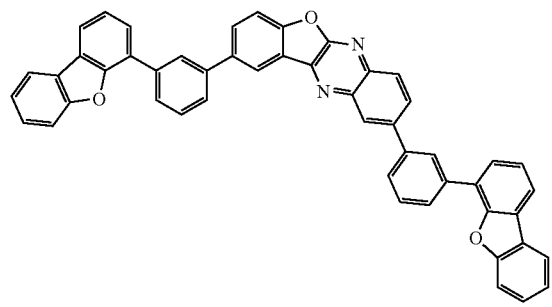
(202)
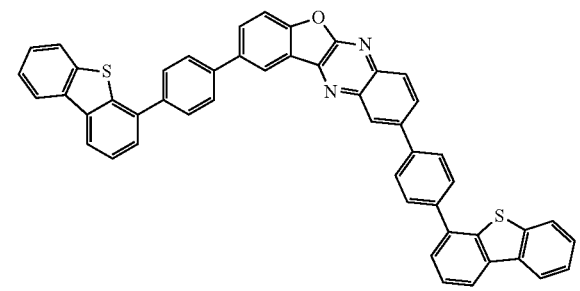
(203)
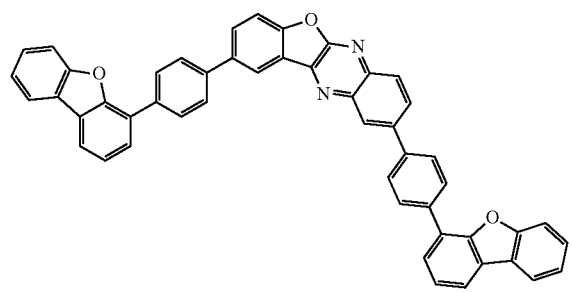
(204)
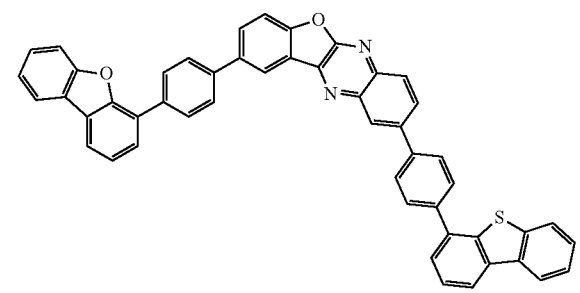

-continued
(205)
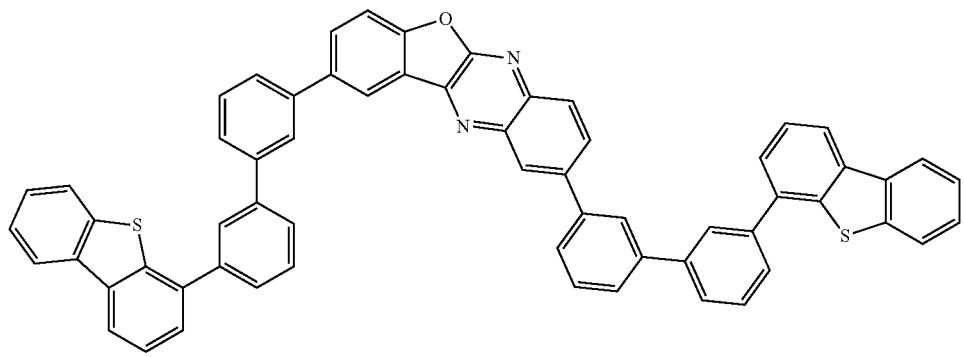
(206)
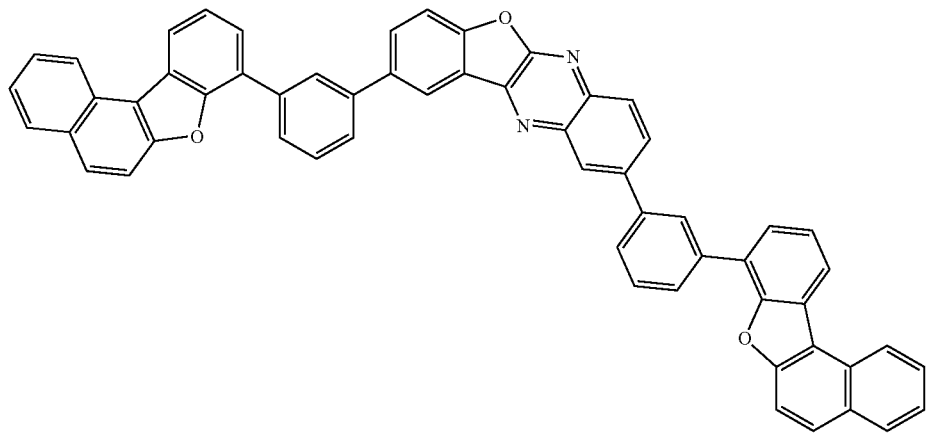
(207)
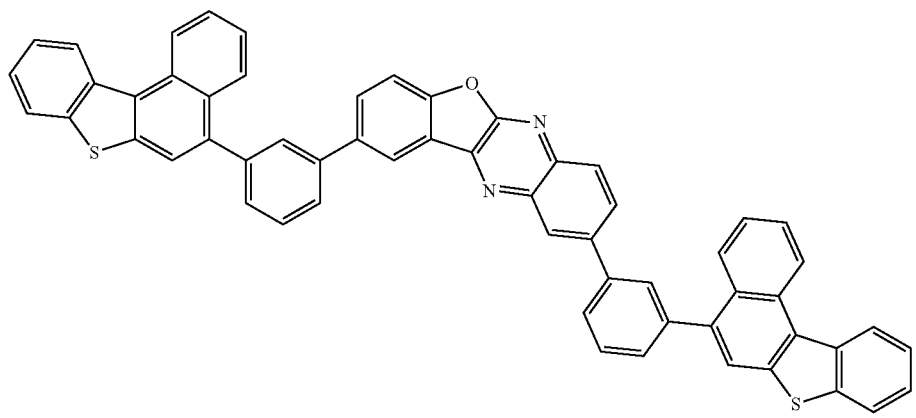
(208)
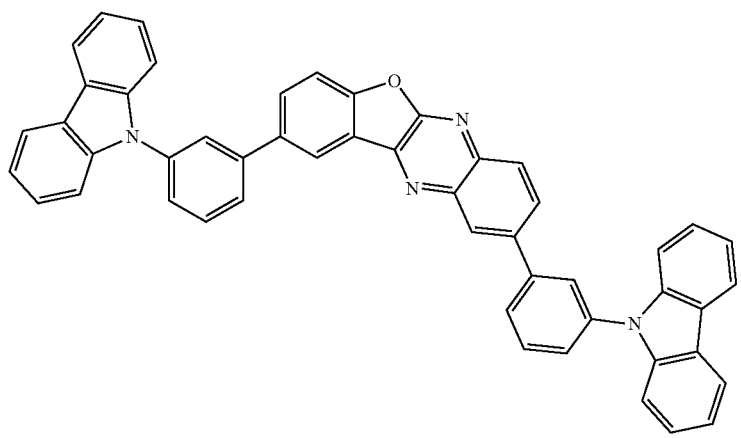

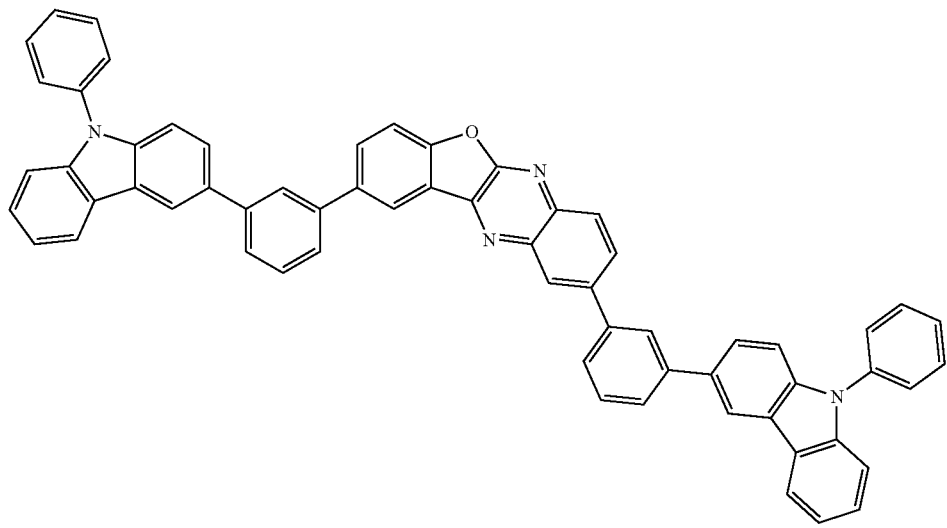
(209)
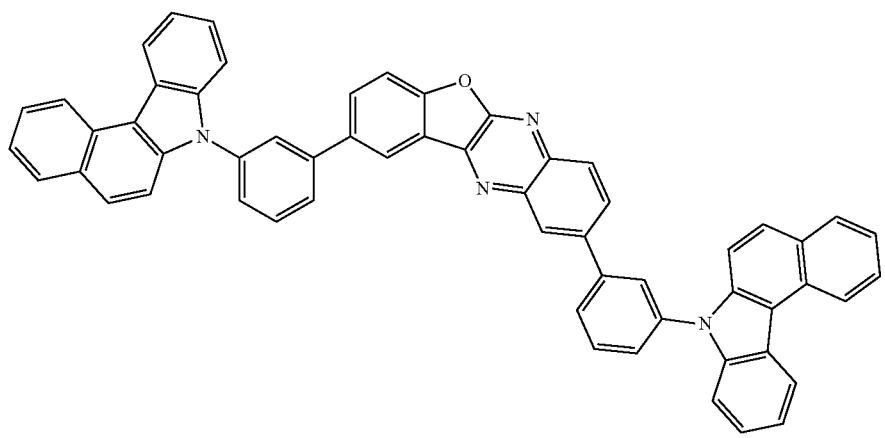
(210)
[Chemical Formulae 21]
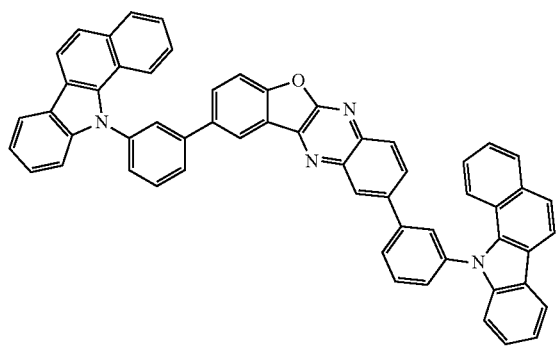
(211)
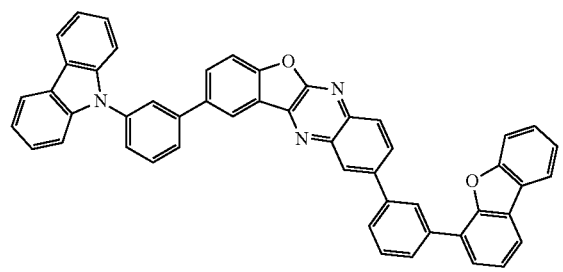
(212)

-continued
(213)
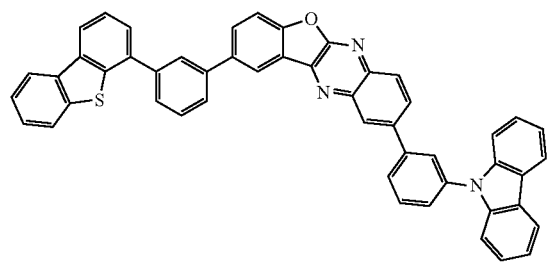
(214)
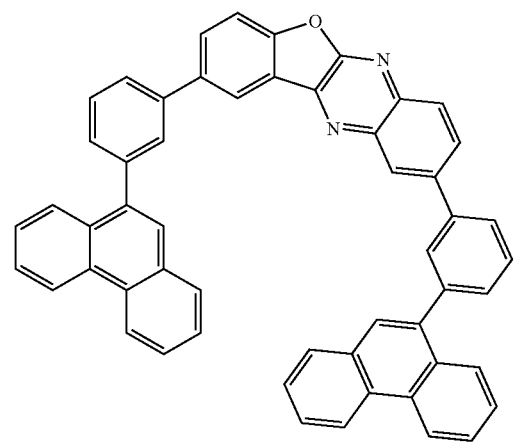
(215)
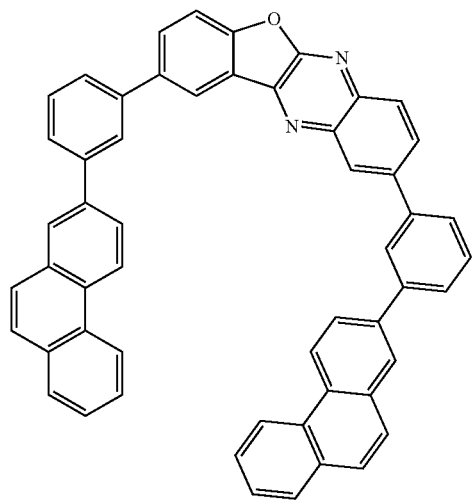
(216)
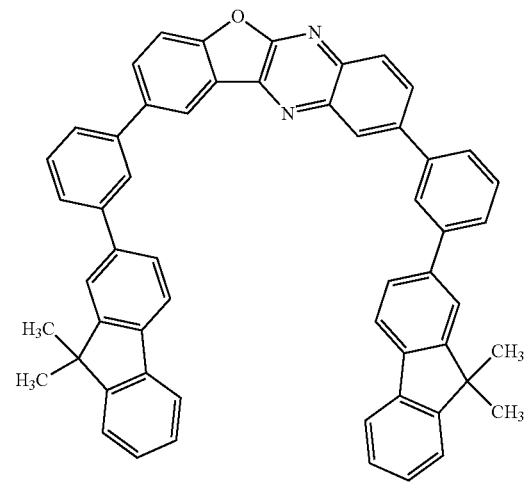
(217)
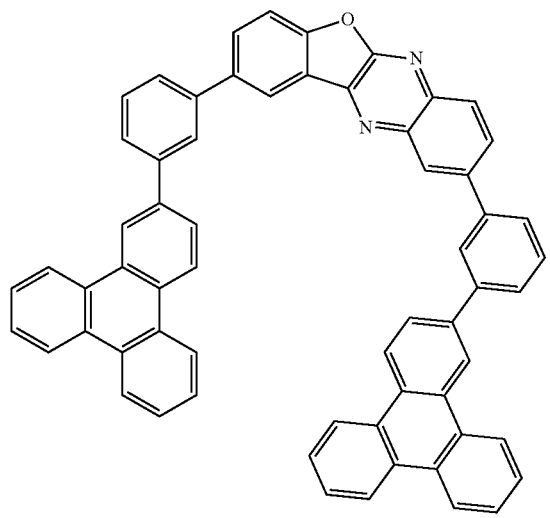
(218)
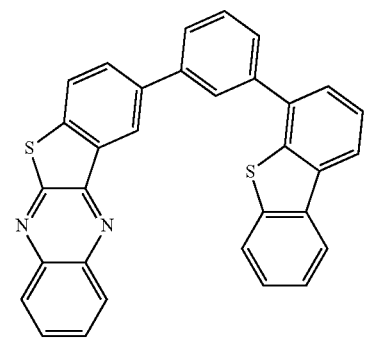

-continued
(219)
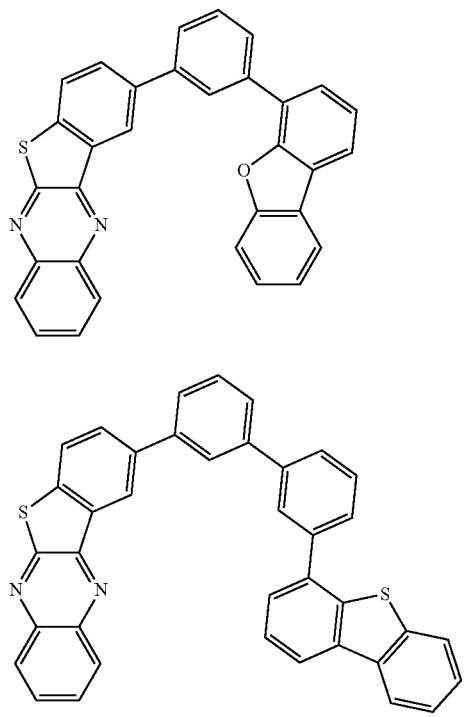
(220)
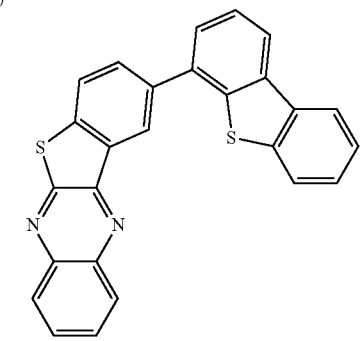
(221)
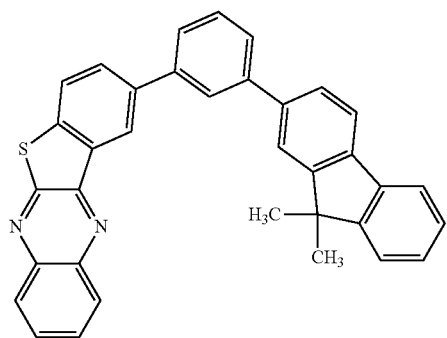
(222)
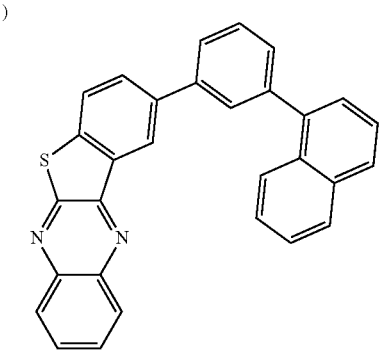
(223)
[Chemical Formulae 22]
(224)
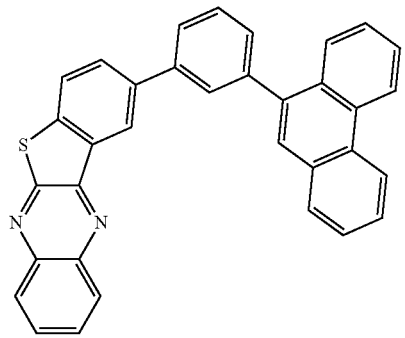
(225)
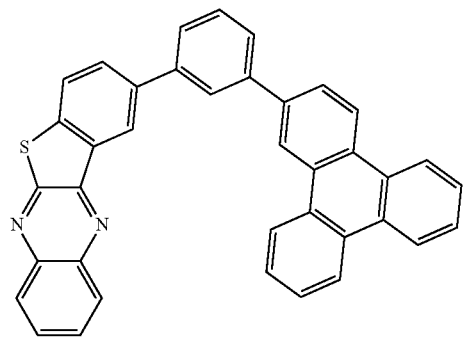

-continued
(226) 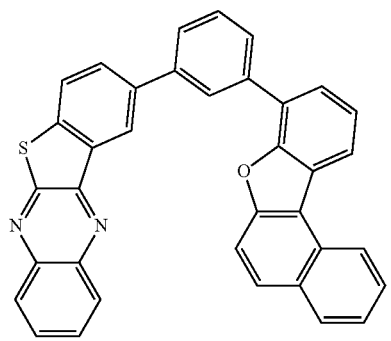
(227) 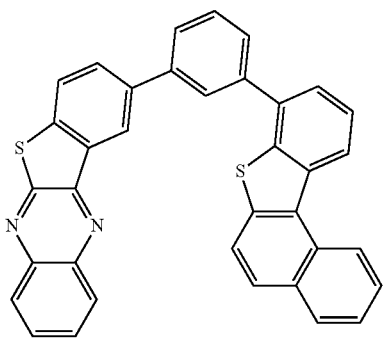
(228) 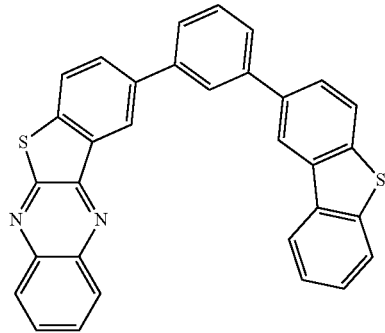
(229) 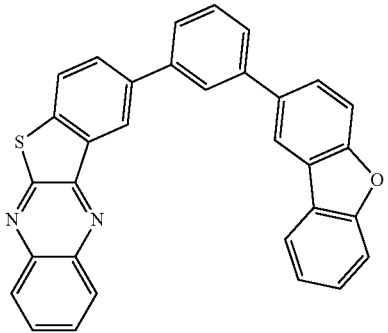
(230) 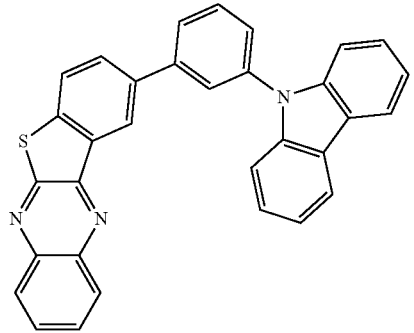
(231) 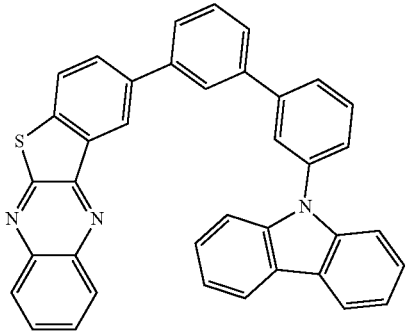
(232) 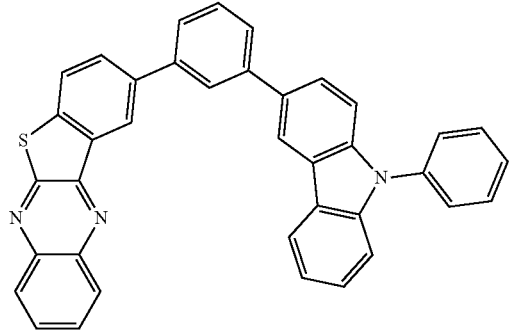
(233) 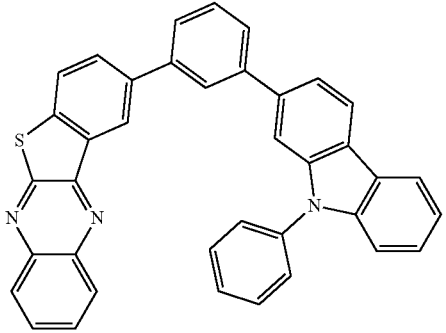

-continued
(234)
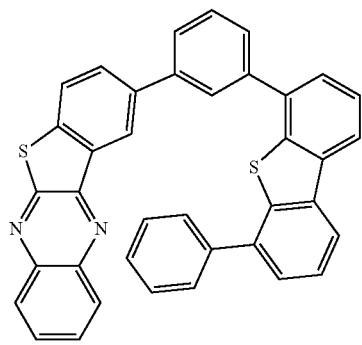
(235)
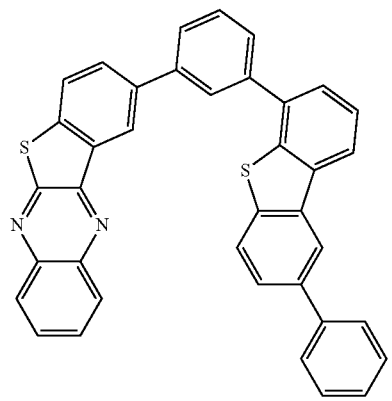
(236)
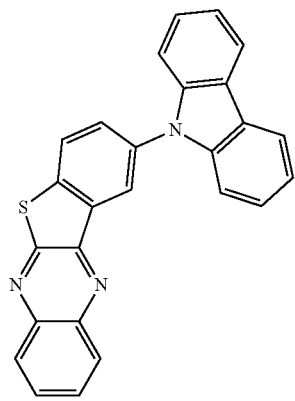
(237)
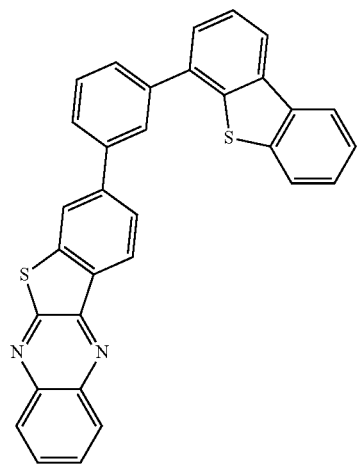
(238)
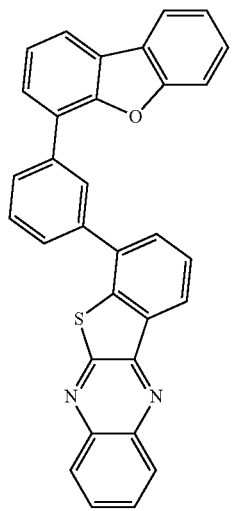
(239)
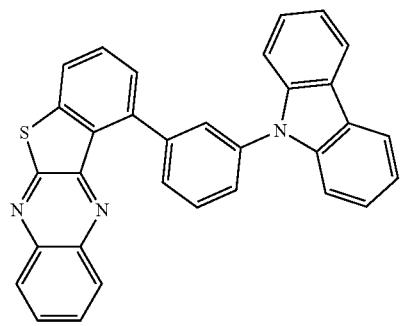

(240)
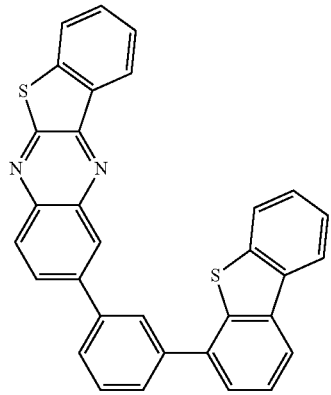
[Chemical Formulae 23]
(241)
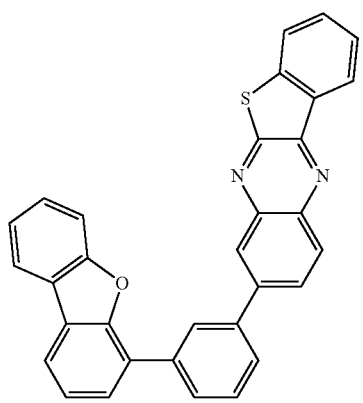
(242)
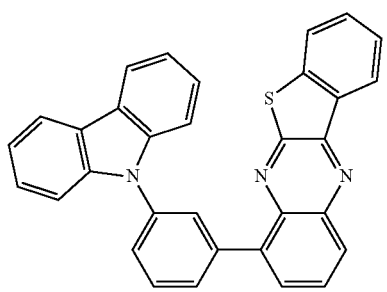
(243)
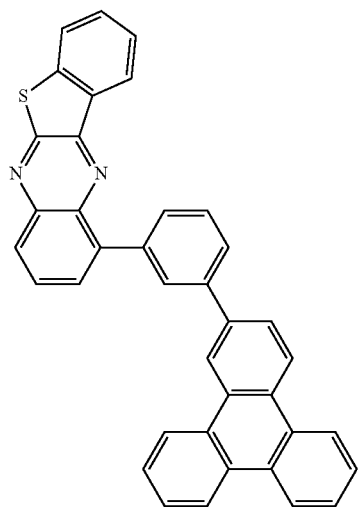
(244)
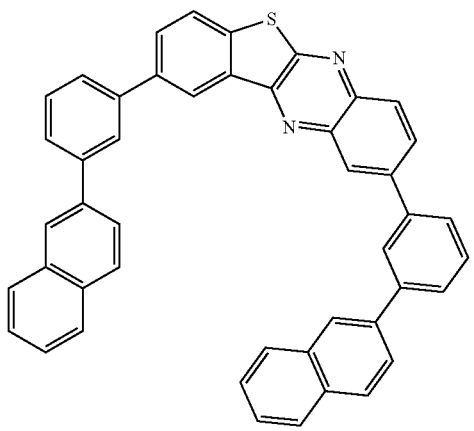
(245)
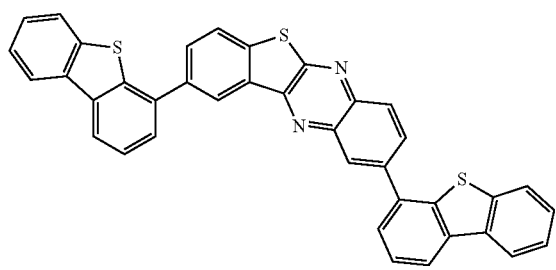
(246)
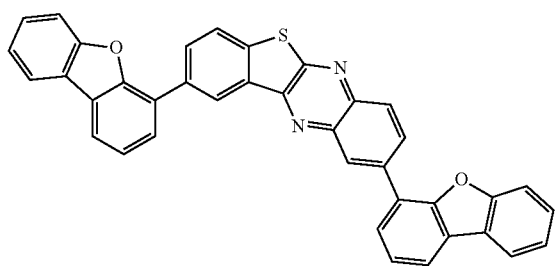

-continued
(247)
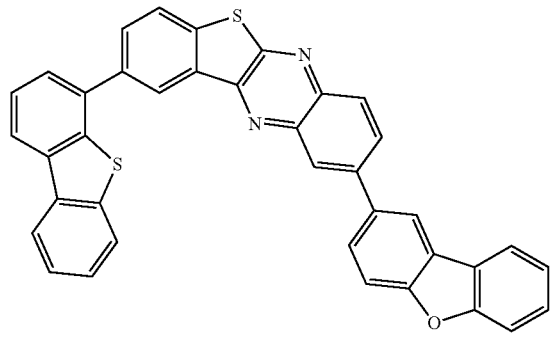
(248)
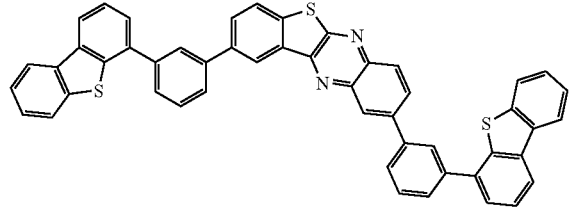
(249)
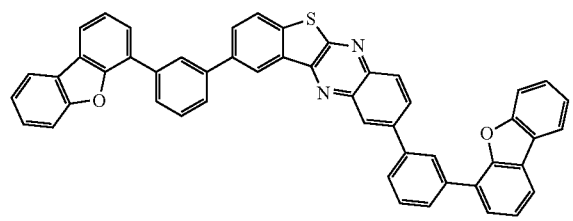
(250)
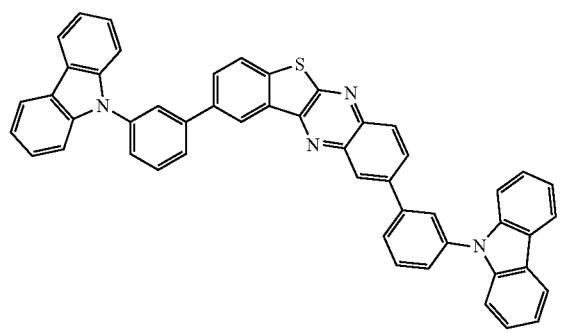
(251)
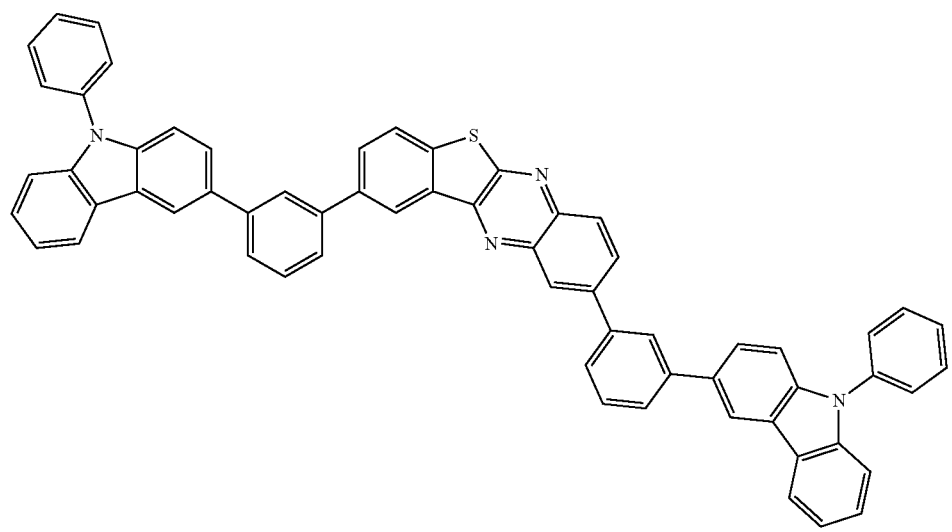
(252)
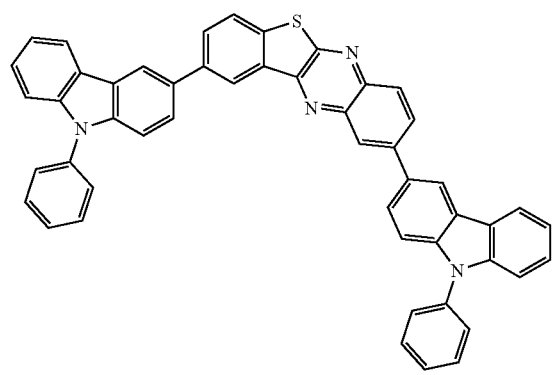
(253)
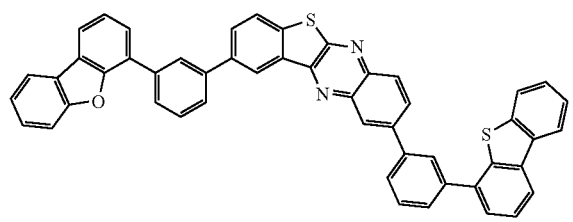

[Chemical Formulae 24]
(254)
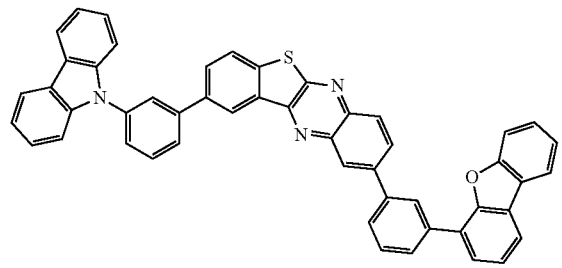
(255)
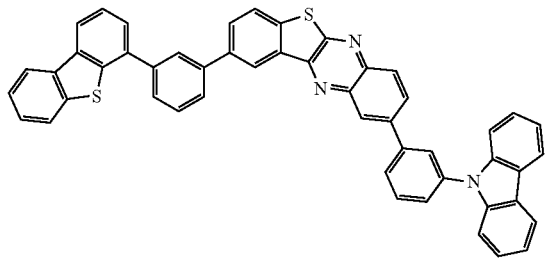
(256)
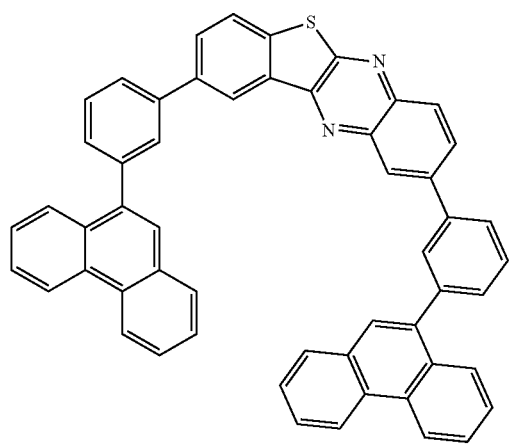
(257)
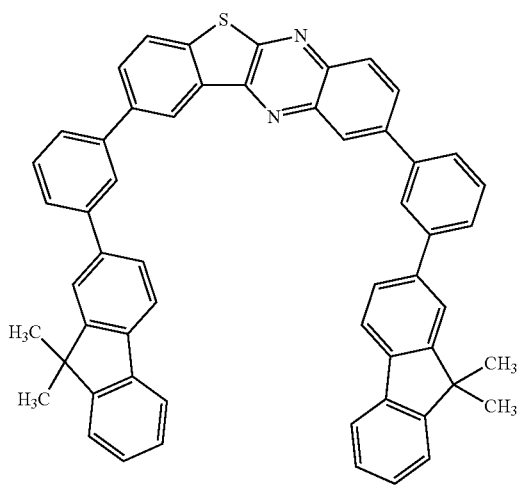
(258)
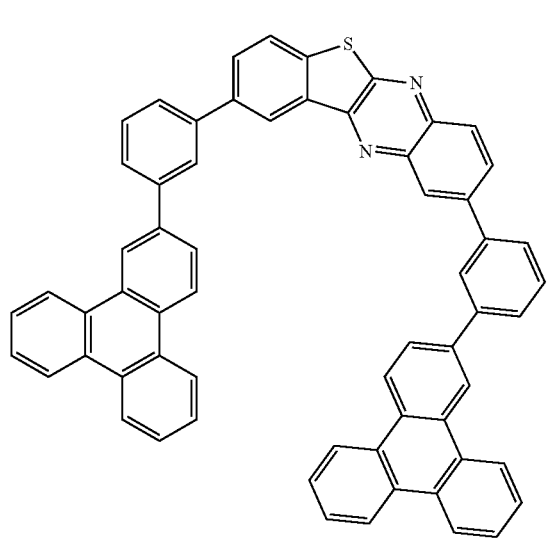
(259)
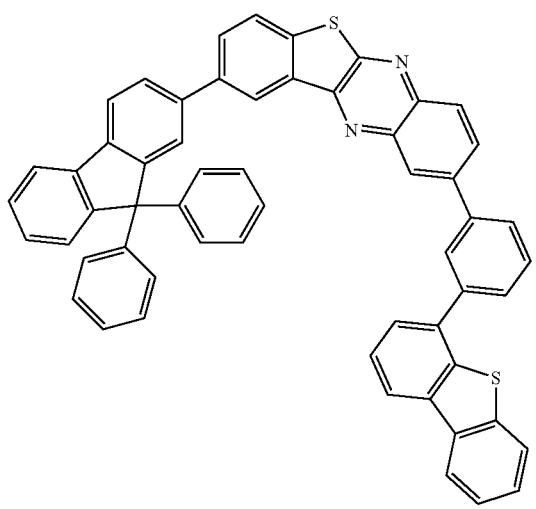

-continued
(260)
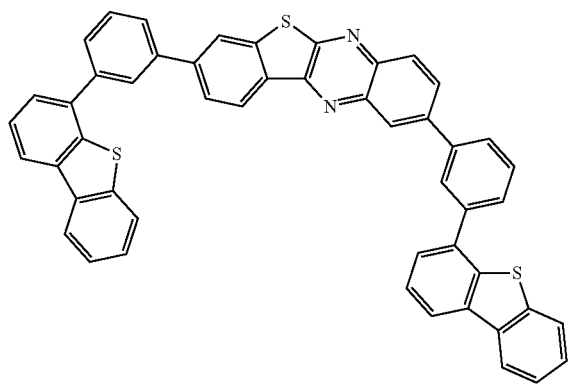
(261)
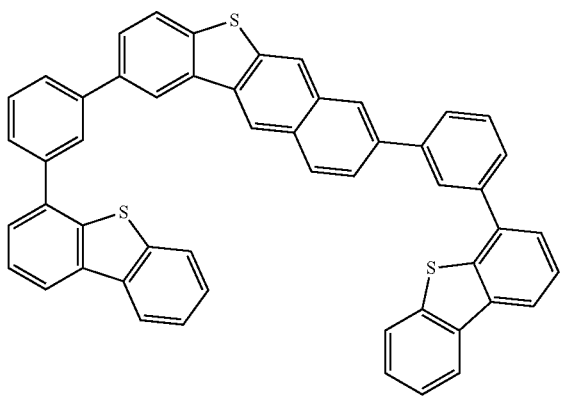
(262)
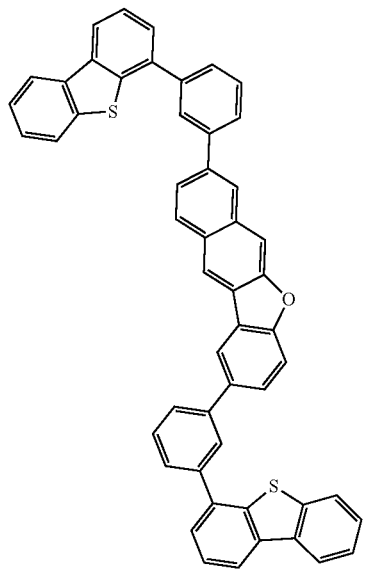
(263)
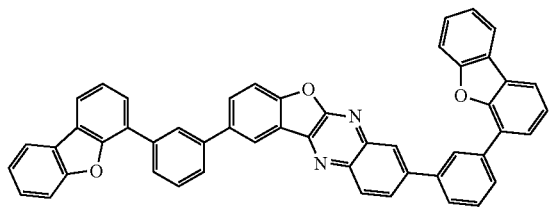
(264)
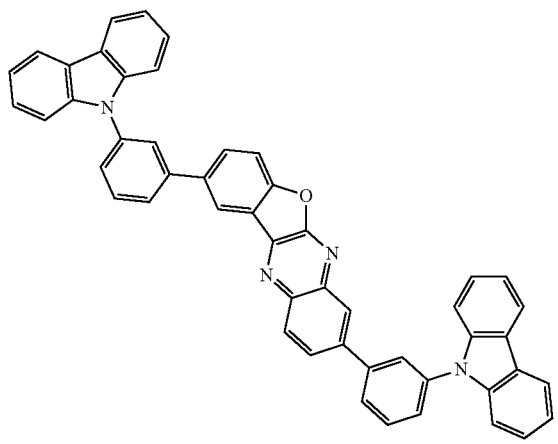
(265)
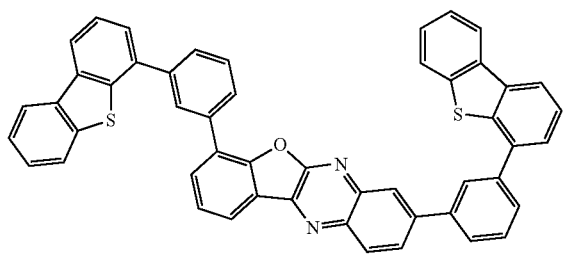

-continued (266)

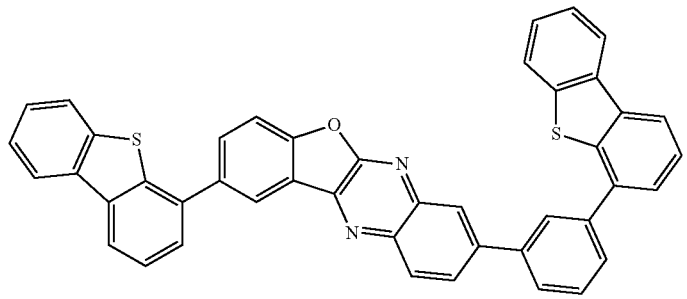

Note that organic compounds represented by Structural Formulae (100) to (266) are examples of the organic compound represented by General Formula (G1). The organic compound of one embodiment of the present invention is not limited thereto.

Next, an example of a method for synthesizing the organic compound of one embodiment of the present invention will be described.

<<Method for Synthesizing Organic Compound Represented by General Formula (G1)>>

First, an example of a method for synthesizing the organic compound represented by General Formula (G1) will be described.

[Chemical Formula 25]

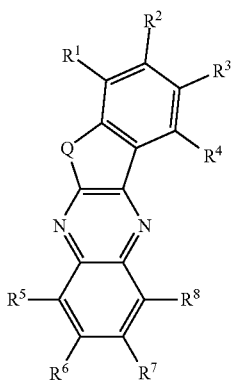

(G1)

In General Formula (G1), Q represents O or S, and each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. At least one of $R^1$ to $R^8$ includes a substituted or unsubstituted condensed aromatic or heteroaromatic ring having 3 to 24 carbon atoms.

First, a method for synthesizing a quinoxaline derivative (a3) is shown by a synthesis scheme (A-1). Specifically, a dihalogen compound, a compound having a ditriflate group, a compound having both a halogeno group and a triflate group, a compound having both a triflate group and an amino group, or a compound having both a halogeno group and an amino group of a quinoxaline derivative (a1) and an organoboron compound or a boronic acid of an aryl derivative (a2) having an alkoxy group or an alkyl sulfanyl group represented by "$R^{11}$-Q-" are subjected to the coupling by the Suzuki-Miyaura reaction in the presence of a palladium catalyst, whereby the quinoxaline derivative (a3) having an alkoxy group and any one of a halogeno group, a triflate group, and an amino group or having an alkyl sulfanyl group and any one of a halogeno group, a triflate group, and an amino group can be obtained.

[Chemical Formula 26]

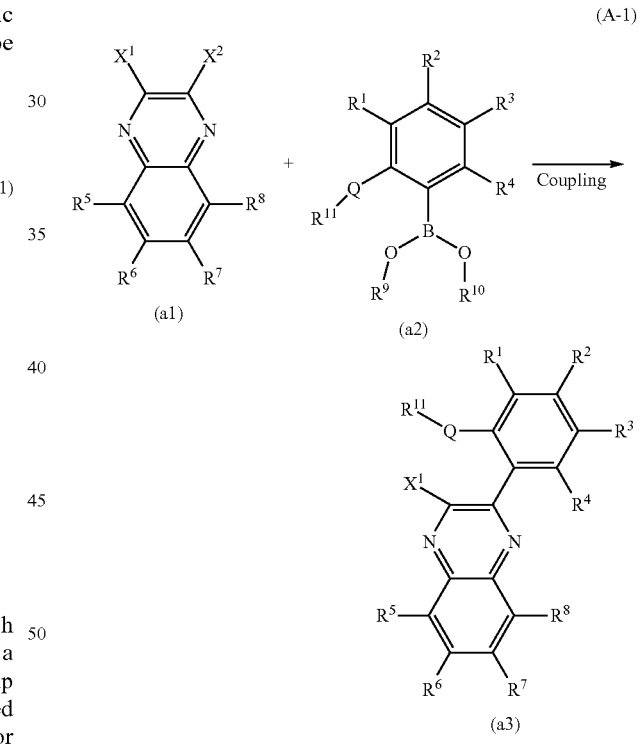

In the synthesis scheme (A-1), Q represents O or S, and each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. In the case where none of $R^1$ to $R^8$ is a halogeno group, at least one of $R^1$ to $R^8$ includes a substituted or unsubstituted condensed aromatic or heteroaromatic ring having 3 to 24 carbon atoms. In the synthesis scheme (A-1), $R^9$ and $R^{10}$, which may be the same or different from each other, represent either hydrogen or an alkyl group having 1 to 6 carbon atoms, and may be bonded to each other to form a ring. In addition, $R^{11}$ represents an alkyl group having 1 to 6 carbon atoms; $X^1$ represents a halogeno group, a triflate group, or an amino group; and $X^2$ represents a halogeno group or a triflate group. When $X^1$ is a halogeno group, the halogeno group is preferably fluorine or chlorine. When $X^2$ is a halogeno group, the halogeno group is preferably chlorine, iodine, or bromine.

For the synthesis scheme (A-1), palladium(II) acetate, tetrakis(triphenylphosphine)palladium(0), or the like can be used as the palladium catalyst. Examples of a ligand of the palladium catalyst include tri(ortho-tolyl)phosphine, triphenylphosphine, and tricyclohexylphosphine. As a base, an organic base such as sodium tert-butoxide, an inorganic base such as potassium carbonate or sodium carbonate, or the like can be used. As a solvent, any of the following can be used: toluene, xylene, benzene, an ether (e.g., 1,2-dimethoxyethane), an alcohol (e.g., ethanol), water, and a mixed solvent of any of them (e.g., a mixed solvent of toluene and ethanol, a mixed solvent of toluene and water, a mixed solvent of xylene and ethanol, a mixed solvent of xylene and water, or a mixed solvent of benzene and ethanol).

An organoboron compound or a boronic acid of a quinoxaline derivative and a halogen compound or a compound having a triflate group of an aryl derivative may be subjected to the coupling by the Suzuki-Miyaura reaction shown by the synthesis scheme (A-1).

Here, a method for synthesizing a quinoxaline derivative (a4) having a hydroxyl group and any one of a halogeno group, a triflate group, and an amino group by deprotection of a quinoxaline derivative (a3') having an alkoxy group and any one of a halogeno group, a triflate group, and an amino group is described using a synthesis scheme (A-2). Specifically, the quinoxaline derivative (a3') having an alkoxy group and any one of a halogeno group, a triflate group, and an amino group is deprotected with a Lewis acid, whereby the quinoxaline derivative (a4) having a hydroxyl group and any one of a halogeno group, a triflate group, and an amino group can be obtained. Note that in the case of a quinoxaline derivative having an amino group and an alkoxy group, deprotection is not performed in some cases.

[Chemical Formula 27]

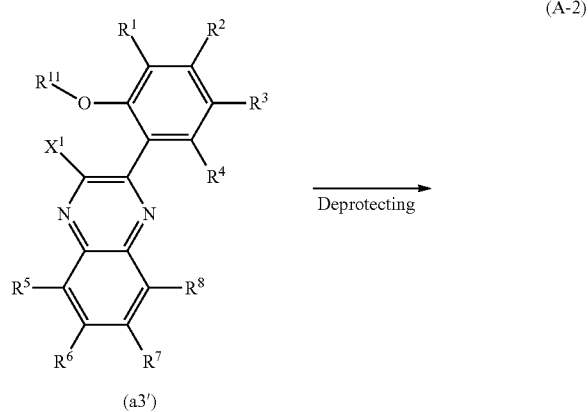

(a3')

-continued

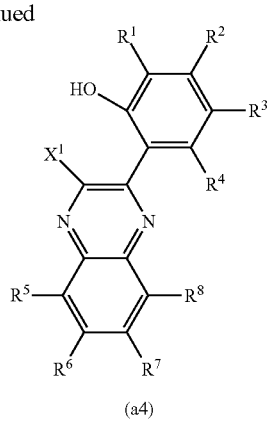

(a4)

In the synthesis scheme (A-2), each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. In the case where none of $R^1$ to $R^8$ is a halogeno group, at least one of $R^1$ to $R^8$ includes a substituted or unsubstituted condensed aromatic or heteroaromatic ring having 3 to 24 carbon atoms. In the synthesis scheme (A-2), $R^{11}$ represents an alkyl group having 1 to 6 carbon atoms, and $X^1$ represents a halogeno group, a triflate group, or an amino group. When $X^1$ is a halogeno group, the halogen group is preferably fluorine or chlorine.

When $R^{11}$ in the synthesis scheme (A-2) is a methyl group, boron tribromide, trimethyliodosilane, or the like can be used as the Lewis acid. When $R^{11}$ is a tert-butyl group, a trifluoroacetic acid, a 4 mol/L hydrochloric acid-ethyl acetate solution, or the like can be used as the Lewis acid. As a solvent, a halogen-based solvent such as dichloromethane, chloroform, or carbon tetrachloride; an aromatic hydrocarbon-based solvent such as toluene or xylene; or the like can be used.

Then, the organic compound (G1) of one embodiment of the present invention is synthesized by a synthesis method shown by a synthesis scheme (A-3). Specifically, the quinoxaline derivative (a3) having an alkyl sulfanyl group and any one of a halogeno group, a triflate group, and an amino group or having an amino group and an alkoxy group or the quinoxaline derivative (a4) having a hydroxyl group and any one of a halogeno group, a triflate group, and an amino group is intramolecularly cyclized, whereby the organic compound (G1) can be obtained. Note that in the case where at least one of $R^1$ to $R^8$ is a halogeno group, coupling can be performed with a boronic acid compound of a substituted or unsubstituted condensed aromatic or heteroaromatic ring having 3 to 24 carbon atoms after the cyclization to obtain the organic compound (G1).

[Chemical Formula 28]

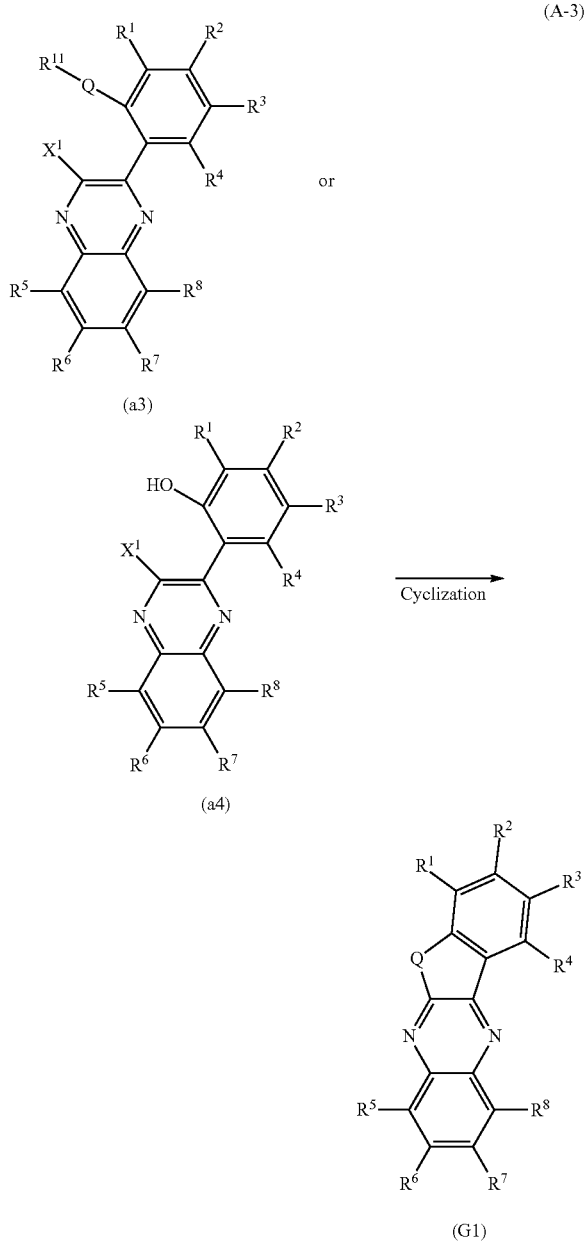

In the synthesis scheme (A-3), Q represents O or S, and each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms. In the case where none of $R^1$ to $R^8$ is a halogeno group, at least one of $R^1$ to $R^8$ includes a substituted or unsubstituted condensed aromatic or heteroaromatic ring having 3 to 24 carbon atoms. In the synthesis scheme (A-3), $R^{11}$ represents an alkyl group having 1 to 6 carbon atoms, and $X^1$ represents a halogeno group, a triflate group, or an amino group. When $X^1$ is a halogeno group, the halogeno group is preferably fluorine or chlorine.

In the case where Williamson ether synthesis cyclization is performed in the synthesis scheme (A-3), an inorganic base such as sodium hydride, potassium carbonate, or potassium hydroxide can be used, for example. A salt such as sodium iodide may be added. Examples of a solvent include aprotic polar solvents such as acetonitrile, N,N-dimethylformamide (DMF), dimethyl sulfoxide (DMSO), and N-methyl-pyrrolidone (NMP) and ketones such as cyclohexanone, 2-butanone, and acetone.

The above is the description of the method for synthesizing the organic compound (G1) of one embodiment of the present invention; however, the present invention is not limited thereto and a different synthesis method may be employed.

Note that the above organic compounds which are embodiments of the present invention each have an electron-transport property and a hole-transport property and thus can be used as a host material in a light-emitting layer or can be used in an electron-transport layer or a hole-transport layer. Furthermore, the above organic compounds are preferably used in combination with a substance that emits phosphorescence (phosphorescent material), as host materials. In addition, the above organic compounds emit fluorescence and thus can be used as light-emitting substances of light-emitting elements. Accordingly, light-emitting elements containing these organic compounds are also included as embodiments of the present invention.

With the use of the organic compound of one embodiment of the present invention, a light-emitting element, light-emitting device, electronic device, or lighting device having high emission efficiency can be obtained. It is also possible to obtain a light-emitting element, light-emitting device, electronic device, or lighting device with low power consumption.

In this embodiment, one embodiment of the present invention has been described. Other embodiments of the present invention are described in the other embodiments. Note that one embodiment of the present invention is not limited thereto. In other words, since various embodiments of the invention are described in this embodiment and the other embodiments, one embodiment of the present invention is not limited to a particular embodiment. For example, although an example of use in a light-emitting element is described in this embodiment, one embodiment of the present invention is not limited thereto. Depending on circumstances, one embodiment of the present invention may be used in objects other than a light-emitting element. Furthermore, depending on circumstances or conditions, one embodiment of the present invention need not be used in a light-emitting element.

The structure described in this embodiment can be used in appropriate combination with the structure described in any of the other embodiments.

Embodiment 2

In this embodiment, light-emitting elements of one embodiment of the present invention will be described.

<<Basic Structure of Light-Emitting Element>>

Basic structures of the light-emitting elements will be described. FIG. 1A illustrates a light-emitting element in which an EL layer having a light-emitting layer is provided between a pair of electrodes. Specifically, an EL layer 103 is provided between a first electrode 101 and a second electrode 102.

Figure 1B:
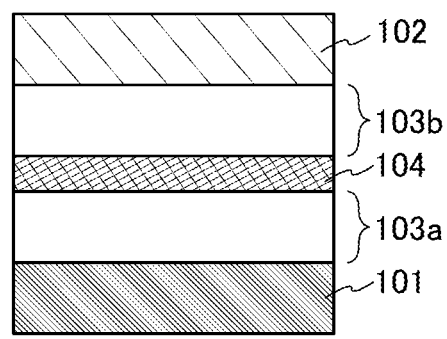

FIG. 1B illustrates a light-emitting element that has a stacked-layer structure (tandem structure) in which a plurality of EL layers (two EL layers 103a and 103b in FIG. 1B) are provided between a pair of electrodes and a charge generation layer 104 is provided between the EL layers. With the use of such a tandem light-emitting element, a light-emitting device which can be driven at low voltage with low power consumption can be obtained.

The charge generation layer 104 has a function of injecting electrons into one of the EL layers (103a or 103b) and injecting holes into the other of the EL layers (103b or 103a) when voltage is applied between the first electrode 101 and the second electrode 102. Thus, when voltage is applied to the first electrode 101 in FIG. 1B to make the potential of the first electrode 101 higher than that of the second electrode 102, the charge generation layer 104 injects electrons into the EL layer 103a and injects holes into the EL layer 103b.

Note that in terms of light extraction efficiency, the charge generation layer 104 preferably has a property of transmitting visible light (specifically, a visible light transmittance of 40% or higher). Furthermore, the charge generation layer 104 functions even if it has lower conductivity than the first electrode 101 or the second electrode 102.

Figure 1C:
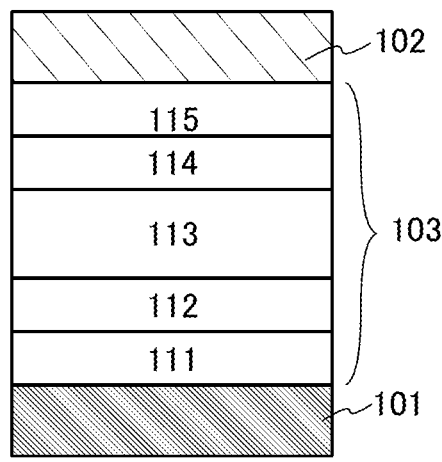

FIG. 1C illustrates a stacked-layer structure of the EL layer 103 in the light-emitting element of one embodiment of the present invention. In this case, the first electrode 101 is regarded as functioning as an anode. The EL layer 103 has a structure in which a hole-injection layer 111, a hole-transport layer 112, a light-emitting layer 113, an electron-transport layer 114, and an electron-injection layer 115 are stacked in this order over the first electrode 101. Even in the case where a plurality of EL layers are provided as in the tandem structure illustrated in FIG. 1B, the layers in each EL layer are sequentially stacked from the anode side as described above. When the first electrode 101 is a cathode and the second electrode 102 is an anode, the stacking order is reversed.

The light-emitting layer 113 included in the EL layers (103, 103a, and 103b) contains an appropriate combination of a light-emitting substance and a plurality of substances, so that fluorescence or phosphorescence of a desired emission color can be obtained. The light-emitting layer 113 may have a stacked-layer structure having different emission colors. In that case, the light-emitting substance and other substances are different between the stacked light-emitting layers. Alternatively, the plurality of EL layers (103a and 103b) in FIG. 1B may exhibit their respective emission colors. Also in that case, the light-emitting substance and other substances are different between the light-emitting layers.

In the light-emitting element of one embodiment of the present invention, for example, a micro optical resonator (microcavity) structure in which the first electrode 101 is a reflective electrode and the second electrode 102 is a transflective electrode can be employed in FIG. 1C, whereby light emission from the light-emitting layer 113 in the EL layer 103 can be resonated between the electrodes and light emission transmitted from the second electrode 102 can be intensified.

Note that when the first electrode 101 of the light-emitting element is a reflective electrode having a structure in which a reflective conductive material and a light-transmitting conductive material (transparent conductive film) are stacked, optical adjustment can be performed by controlling the thickness of the transparent conductive film. Specifically, when the wavelength of light from the light-emitting layer 113 is $\lambda$, the distance between the first electrode 101 and the second electrode 102 is preferably adjusted to around $m\lambda/2$ (m is a natural number).

To amplify desired light (wavelength: k) obtained from the light-emitting layer 113, the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) are preferably adjusted to around $(2m'+1)\lambda/4$ (m' is a natural number). Here, the light-emitting region means a region where holes and electrons are recombined in the light-emitting layer 113.

By such optical adjustment, the spectrum of specific monochromatic light from the light-emitting layer 113 can be narrowed and light emission with high color purity can be obtained.

In that case, the optical path length between the first electrode 101 and the second electrode 102 is, to be exact, the total thickness from a reflective region in the first electrode 101 to a reflective region in the second electrode 102. However, it is difficult to exactly determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer emitting the desired light is, to be exact, the optical path length between the reflective region in the first electrode 101 and the light-emitting region where the desired light is obtained in the light-emitting layer. However, it is difficult to precisely determine the reflective region in the first electrode 101 and the light-emitting region where the desired light is obtained in the light-emitting layer; thus, it is assumed that the above effect can be sufficiently obtained wherever the reflective region and the light-emitting region may be set in the first electrode 101 and the light-emitting layer emitting the desired light.

The light-emitting element in FIG. 1C has a microcavity structure, so that light (monochromatic light) with different wavelengths can be extracted even if the same EL layer is used. Thus, separate coloring for obtaining a plurality of emission colors (e.g., R, G, and B) is not necessary. Therefore, high resolution can be easily achieved. Note that a combination with coloring layers (color filters) is also possible. Furthermore, emission intensity of light with a specific wavelength in the front direction can be increased, whereby power consumption can be reduced.

In the light-emitting element of one embodiment of the present invention, at least one of the first electrode 101 and the second electrode 102 is a light-transmitting electrode (e.g., a transparent electrode or a transflective electrode). In the case where the light-transmitting electrode is a transparent electrode, the transparent electrode has a visible light transmittance of higher than or equal to 40%. In the case where the light-transmitting electrode is a transflective electrode, the transflective electrode has a visible light reflectance of higher than or equal to 20% and lower than or equal to 80%, and preferably higher than or equal to 40% and lower than or equal to 70%. These electrodes preferably have a resistivity of $1\times10^{-2}$ $\Omega$cm or less.

Furthermore, when one of the first electrode 101 and the second electrode 102 is a reflective electrode in the light-emitting element of one embodiment of the present invention, the visible light reflectance of the reflective electrode is higher than or equal to 40% and lower than or equal to 100%, and preferably higher than or equal to 70% and lower than or equal to 100%. This electrode preferably has a resistivity of $1\times10^{-2}$ $\Omega$cm or less.

<<Specific Structure and Fabrication Method of Light-Emitting Element>>

Specific structures and specific fabrication methods of light-emitting elements of embodiments of the present invention will be described with reference to FIGS. 1A to 1D. Here, a light-emitting element having the tandem structure in FIG. 1B and a microcavity structure will be described with reference to FIG. 1D. In the light-emitting element in FIG. 1D having a microcavity structure, the first electrode 101 is formed as a reflective electrode and the second electrode 102 is formed as a transflective electrode. Thus, a single-layer structure or a stacked-layer structure can be formed using one or more kinds of desired electrode materials. Note that the second electrode 102 is formed after formation of the EL layer 103b, with the use of a material selected as described above. For fabrication of these electrodes, a sputtering method or a vacuum evaporation method can be used.

<First Electrode and Second Electrode>

As materials used for the first electrode 101 and the second electrode 102, any of the materials below can be used in an appropriate combination as long as the functions of the electrodes described above can be fulfilled. For example, a metal, an alloy, an electrically conductive compound, a mixture of these, and the like can be appropriately used. Specifically, an In—Sn oxide (also referred to as ITO), an In—Si—Sn oxide (also referred to as ITSO), an In—Zn oxide, an In—W—Zn oxide, or the like can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table, which is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

Figure 1D:
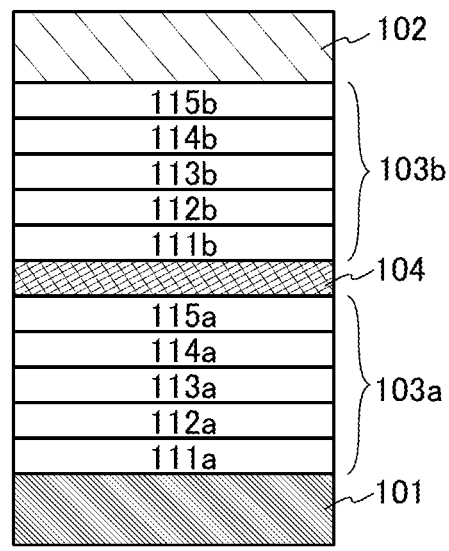

In the light-emitting element in FIG. 1D, when the first electrode 101 is an anode, a hole-injection layer 11a and a hole-transport layer 112a of the EL layer 103a are sequentially stacked over the first electrode 101 by a vacuum evaporation method. After the EL layer 103a and the charge generation layer 104 are formed, a hole-injection layer 111b and a hole-transport layer 112b of the EL layer 103b are sequentially stacked over the charge generation layer 104 in a similar manner.

<Hole-Injection Layer and Hole-Transport Layer>

The hole-injection layers (111, 111a, and 111b) inject holes from the first electrode 101 that is an anode or the charge generation layer (104) to the EL layers (103, 103a, and 103b) and each contain a material with a high hole-injection property.

As examples of the material with a high hole-injection property, transition metal oxides such as molybdenum oxide, vanadium oxide, ruthenium oxide, tungsten oxide, and manganese oxide can be given. Alternatively, it is possible to use any of the following materials: phthalocyanine-based compounds such as phthalocyanine (abbreviation: H₂Pc) and copper phthalocyanine (abbreviation: CuPc); aromatic amine compounds such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD); high molecular compounds such as poly(3,4-ethylenedioxythiophene)/poly(styrenesulfonic acid)(abbreviation: PEDOT/PSS); and the like.

Alternatively, as the material with a high hole-injection property, a composite material containing a hole-transport material and an acceptor material (an electron-accepting material) can also be used. In that case, the acceptor material extracts electrons from a hole-transport material, so that holes are generated in the hole-injection layers (111, 111a, and 111b) and the holes are injected into the light-emitting layers (113, 113a, and 113b) through the hole-transport layers (112, 112a, and 112b). Note that each of the hole-injection layers (111, 11a, and 1/1b) may be formed to have a single-layer structure using a composite material containing a hole-transport material and an acceptor material (electron-accepting material), or a stacked-layer structure in which a layer including a hole-transport material and a layer including an acceptor material (electron-accepting material) are stacked.

The hole-transport layers (112, 112a, and 112b) transport the holes, which are injected from the first electrode 101 or the charge generation layer by the hole-injection layers (111, 111a, and 111b), to the light-emitting layers (113, 113a, and 113b). Note that the hole-transport layers (112, 112a, and 112b) each contain a hole-transport material. It is particularly preferable that the HOMO level of the hole-transport material included in the hole-transport layers (112, 112a, and 112b) be the same as or close to that of the hole-injection layers (111, 111a, and 111b).

Examples of the acceptor material used for the hole-injection layers (111, 111a, and 111b) include an oxide of a metal belonging to any of Group 4 to Group 8 of the periodic table. Specifically, molybdenum oxide, vanadium oxide, niobium oxide, tantalum oxide, chromium oxide, tungsten oxide, manganese oxide, and rhenium oxide can be given. Among these, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. Specifically, 7,7,8,8-tetracyano-2,3,5,6-tetrafluoroquinodimethane (abbreviation: F₄-TCNQ), chloranil, 2,3,6,7,10,11-hexacyano-1,4,5,8,9,12-hexaazatriphenylene (abbreviation: HAT-CN), and the like can be used.

The hole-transport materials used for the hole-injection layers (111, 111a, and 111b) and the hole-transport layers (112, 112a, and 112b) are preferably substances with a hole mobility greater than or equal to 10-6 cm²/Vs. Note that other substances may be used as long as the substances have a hole-transport property higher than an electron-transport property.

Preferred hole-transport materials are 7-electron rich heteroaromatic compounds (e.g., carbazole derivatives and indole derivatives) and aromatic amine compounds, examples of which include compounds having an aromatic amine skeleton, such as 4,4'-bis[N-(1-naphthyl)-N-phenylamino]biphenyl (abbreviation: NPB or α-NPD), N,N-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 3-[4-(9-phenanthryl)-phenyl]-9-phenyl-9H-carbazole (abbreviation: PCPPn), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 4,4',4''-tris(carbazol-9-yl)triphenylamine (abbreviation: TCTA), 4,4',4''-tris(N,N-diphenylamino)triphenylamine (abbreviation: TDATA), and 4,4',4''-tris[N-(3-methylphenyl)-N-phenylamino]triphenylamine (abbreviation: MTDATA); compounds having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation:PCzPCA2), 3-[N-(1-naphthyl)-N-(9-phenyl-carbazol-3-yl)amino]-9-phenylcarbazole (abbreviation: PCzPCN1), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA); compounds having a thiophene skeleton, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

A high molecular compound such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)methacrylamide] (abbreviation: PTPDMA), or poly[N,N-bis(4-butylphenyl)-N,N-bis(phenyl)benzidine](abbreviation: Poly-TPD) can also be used.

Note that the hole-transport material is not limited to the above examples and may be one of or a combination of various known materials when used for the hole-injection layers (111, 111a, and 111b) and the hole-transport layers (112, 112a, and 112b). Note that the hole-transport layers (112, 112a, and 112b) may each be formed of a plurality of layers. That is, for example, the hole-transport layers may each have a stacked-layer structure of a first hole-transport layer and a second hole-transport layer.

In the light-emitting element in FIG. 1D, the light-emitting layer 113a is formed over the hole-transport layer 112a of the EL layer 103a by a vacuum evaporation method. After the EL layer 103a and the charge generation layer 104 are formed, the light-emitting layer 113b is formed over the hole-transport layer 112b of the EL layer 103b by a vacuum evaporation method.

<Light-Emitting Layer>

The light-emitting layers (113, 113a, and 113b) each contain a light-emitting substance. Note that as the light-emitting substance, a substance whose emission color is blue, violet, bluish violet, green, yellowish green, yellow, orange, red, or the like is appropriately used. When the plurality of light-emitting layers (113a and 113b) are formed using different light-emitting substances, different emission colors can be exhibited (for example, complementary emission colors are combined to achieve white light emission). Furthermore, a stacked-layer structure in which one light-emitting layer contains two or more kinds of light-emitting substances may be employed.

The light-emitting layers (113, 113a, and 113b) may each contain one or more kinds of organic compounds (a host material and an assist material) in addition to a light-emitting substance (guest material). As the one or more kinds of organic compounds, one or both of the hole-transport material and the electron-transport material described in this embodiment can be used.

There is no particular limitation on light-emitting substances other than the above that can be used for the light-emitting layers (113, 113a, and 113b), and a light-emitting substance that converts singlet excitation energy into light emission in the visible light range or a light-emitting substance that converts triplet excitation energy into light emission in the visible light range can be used. Examples of the light-emitting substance are given below.

As an example of the light-emitting substance that converts singlet excitation energy into light emission, a substance that emits fluorescence (fluorescent material) can be given. Examples of the substance that emits fluorescence include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N-bis(3-methylphenyl)-N,N-bis[3-(9-phenyl-9H-fluoren-9-yl)phenyl]pyrene-1,6-diamine (abbreviation: 1,6mMemFLPAPrn), N,N-diphenyl-N,N-bis[4-(9-phenyl-9H-fluoren-9-yl)phenyl]pyrene-1,6-diamine (abbreviation: 1,6FLPAPrn), N,N-bis(dibenzofuran-2-yl)-N,N-diphenylpyrene-1,6-diamine (abbreviation: 1,6FrAPrn), N,N-bis(dibenzothiophen-2-yl)-N,N-diphenylpyrene-1,6-diamine (abbreviation: 1,6ThAPrn), N,N-(pyrene-1,6-diyl)bis[(N-phenylbenzo[b]naphtho[1,2-d]furan)-6-amine](abbreviation: 1,6BnfAPrn), N,N-(pyrene-1,6-diyl)bis[(N-phenylbenzo[b]naphtho[1,2-d]furan)-8-amine] (abbreviation: 1,6BnfAPrn-02), and N,N-(pyrene-1,6-diyl)bis[(6,N-diphenylbenzo[b]naphtho[1,2-d]furan)-8-amine] (abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N''-(2-tert-butylanthracene-9,10-diyldi-4,1-phenylene)bis[N,N,N-triphenyl-1,4-phenylenedia mine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), or the like.

As examples of a light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit the respective emission colors (emission peaks) and thus, any of them is appropriately selected according to need.

As examples of a phosphorescent material which emits blue or green light and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [r(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [r(dmpimpt-Me)$_3$]); organometallic complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)); and the like can be given.

As examples of a phosphorescent material which emits green or yellow light and whose emission spectrum has a peak wavelength at greater than or equal to 495 nm and less than or equal to 590 nm, the following substances can be given.

For example, organometallic complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN3]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); organometallic complexes such as bis(2,4-diphenyl-1,3-oxazolato-N,C$^{2'}$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^{2'}$)iridium(III) acetylacetonate (abbreviation: [Ir(bt)$_2$(acac)]); and rare earth metal complexes such as tris(acetylacetonato)(monophenanthroline)terbium(III)(abbreviation: [Tb(acac)$_3$(Phen)])canbe given.

As examples of a phosphorescent material which emits yellow or red light and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III) (abbreviation: [Ir(dlnpm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III)(abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic complexes having a pyridine skeleton, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]) can be given.

As the organic compounds (the host material and the assist material) used in the light-emitting layers (113, 113a, and 113b), one or more kinds of substances having a larger energy gap than the light-emitting substance (the guest material) are used. Note that any of the hole-transport materials listed above and the electron-transport materials given below may be used as the organic compounds (the host material and the assist material).

When the light-emitting substance is a fluorescent material, it is preferable to use, as the host material, an organic compound that has a high energy level in a singlet excited state and has a low energy level in a triplet excited state. For example, an anthracene derivative or a tetracene derivative is preferably used. Specific examples include 9-phenyl-3-

[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 5,12-diphenyltetracene, and 5,12-bis(biphenyl-2-yl)tetracene.

In the case where the light-emitting substance is a phosphorescent material, an organic compound having triplet excitation energy (energy difference between a ground state and a triplet excited state) which is higher than that of the light-emitting substance is preferably selected as the host material. In that case, it is possible to use a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, a phenanthroline derivative, an aromatic amine, a carbazole derivative, and the like.

Specific examples include metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)-tris(1-phenyl-1H-benzimidazole) (abbreviation: TPBI), bathophenanthroline (abbreviation: Bphen), bathocuproine (abbreviation: BCP), 2,9-bis(naphthalen-2-yl)-4,7-diphenyl-1,10-phenanthroline (abbreviation: NBphen), and 9-[4-(5-phenyl-1,3,4-oxadiazol-2-yl)phenyl]-9H-carbazole (abbreviation: CO11); and aromatic amine compounds such as NPB, TPD, and BSPB.

In addition, condensed polycyclic aromatic compounds such as anthracene derivatives, phenanthrene derivatives, pyrene derivatives, chrysene derivatives, and dibenzo[g,p]chrysene derivatives can be used. Specifically, 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine(abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N,N,N',N',N'',N''-octaphenyldibenzo[g,p]chrysene-2,7,10,15-tetraamine (abbreviation: DBC1), 9-[4-(10-phenyl-9-anthracenyl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), or the like can be used.

In the case where a plurality of organic compounds are used for the light-emitting layers (113, 113a, and 113b), compounds that form an exciplex are preferably used in combination with a phosphorescent substance. With such a structure, light emission can be obtained by exciplex-triplet energy transfer (ExTET), which is energy transfer from an exciplex to a light-emitting substance. In that case, any of various organic compounds can be combined appropriately to be used; it is particularly preferable to combine a compound that easily accepts holes (hole-transport material) and a compound that easily accepts electrons (electron-transport material) to form an exciplex efficiently. The organic compound of one embodiment of the present invention has a low LUMO level and thus is suitable for the compound that easily accepts electrons. When the HOMO level of the compound that easily accepts holes, which is combined with the organic compound of one embodiment of the present invention, is lower than or equal to −5.3 eV, excitation energy can be transferred from an exciplex to a light-emitting substance efficiently. This is further preferable in terms of improving the efficiency of a phosphorescent light-emitting element, improving the reliability, and reducing the driving voltage. As the hole-transport material and the electron-transport material, specifically, any of the materials described in this embodiment can be used.

The TADF material is a material that can up-convert a triplet excited state into a singlet excited state (i.e., reverse intersystem crossing is possible) using a little thermal energy and efficiently exhibits light emission (fluorescence) from the singlet excited state. The TADF is efficiently obtained under the condition where the difference in energy between the triplet excited level and the singlet excited level is greater than or equal to 0 eV and less than or equal to 0.2 eV, preferably greater than or equal to 0 eV and less than or equal to 0.1 eV. Note that "delayed fluorescence" exhibited by the TADF material refers to light emission having the same spectrum as normal fluorescence and an extremely long lifetime. The lifetime is 10-6 seconds or longer, preferably 10-3 seconds or longer.

Examples of the TADF material include fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP).

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (PIC-TRZ), 2-{4-[3-(N-phenyl-9H-carbazol-3-yl)-9H-carbazol-9-yl]phenyl}-4,6-diphenyl-1,3,5-triazine (PCCzPTzn), 2-[4-(10H-phenoxazin-10-yl)phenyl]-4,6-diphenyl-1,3,5-triazine (PXZ-TRZ), 3-[4-(5-phenyl-5,10-dihydrophenazin-10-yl)phenyl]-4,5-diphenyl-1,2,4-triazole (PPZ-3TPT), 3-(9,9-dimethyl-9H-acridin-10-yl)-9H-xanthen-9-one (ACRXTN), bis[4-(9,9-dimethyl-9,10-dihydroacridine)phenyl]sulfone (DMAC-DPS), or 10-phenyl-10H,10'H-spiro[acridin-9,9'-anthracen]-10'-one (ACRSA) can be used. Note that a substance in which the π-electron rich heteroaromatic ring is directly bonded to the π-electron deficient heteroaromatic ring is particularly preferable because both the donor property of the π-electron rich heteroaromatic ring and the acceptor property of the π-electron deficient heteroaromatic ring are increased and the energy difference between the singlet excited state and the triplet excited state becomes small.

Note that when a TADF material is used, the TADF material can be combined with another organic compound.

In the light-emitting element in FIG. 1D, the electron-transport layer 114a is formed over the light-emitting layer 113a of the EL layer 103a by a vacuum evaporation method. After the EL layer 103a and the charge generation layer 104 are formed, the electron-transport layer 114b is formed over the light-emitting layer 113b of the EL layer 103b by a vacuum evaporation method.

<Electron-Transport Layer>

The electron-transport layers (114, 114a, and 114b) transport the electrons, which are injected from the second electrode 102 by the electron-injection layers (115, 115a, and 115b), to the light-emitting layers (113, 113a, and 113b). Note that the electron-transport layers (114, 114a, and 114b) each contain an electron-transport material. It is preferable that the electron-transport materials included in the electron-transport layers (114, 114a, and 114b) be substances with an electron mobility of higher than or equal to $1 \times 10^{-6}$ cm$^2$/Vs. Note that other substances may also be used as long as the substances have an electron-transport property higher than a hole-transport property.

Examples of the electron-transport material include metal complexes having a quinoline ligand, a benzoquinoline ligand, an oxazole ligand, and a thiazole ligand; an oxadiazole derivative; a triazole derivative; a phenanthroline derivative; a pyridine derivative; and a bipyridine derivative. In addition, a π-electron deficient heteroaromatic compound such as a nitrogen-containing heteroaromatic compound can also be used.

Specifically, it is possible to use metal complexes such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, and bis[2-(2-hydroxyphenyl)benzothiazolato]zinc (abbreviation: Zn(BTZ)$_2$), heteroaromatic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole(abbreviation: p-EtTAZ), bathophenanthroline (abbreviation: Bphen), bathocuproine (abbreviation: BCP), and 4,4'-bis(5-methylbenzoxazol-2-yl)stilbene (abbreviation: BzOs), and quinoxaline derivatives and dibenzoquinoxaline derivatives such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used.

Each of the electron-transport layers (114, 114a, and 114b) is not limited to a single layer, but may be a stack of two or more layers each containing any of the above substances.

In the light-emitting element in FIG. 1D, the electron-injection layer 115a is formed over the electron-transport layer 114a of the EL layer 103a by a vacuum evaporation method. Subsequently, the EL layer 103a and the charge generation layer 104 are formed, the components up to the electron-transport layer 114b of the EL layer 103b are formed, and then the electron-injection layer 115b is formed thereover by a vacuum evaporation method.

<Electron-Injection Layer>

The electron-injection layers (115, 115a, and 115b) each contain a substance having a high electron-injection property. The electron-injection layers (115, 115a, and 115b) can each be formed using an alkali metal, an alkaline earth metal, or a compound thereof, such as lithium fluoride (LiF), cesium fluoride (CsF), calcium fluoride (CaF$_2$), or lithium oxide (LiO$_x$). A rare earth metal compound like erbium fluoride (ErF$_3$) can also be used. Electride may also be used for the electron-injection layers (115, 115a, and 115b). Examples of the electride include a substance in which electrons are added at high concentration to calcium oxide-aluminum oxide. Any of the substances for forming the electron-transport layers (114, 114a, and 114b), which are given above, can also be used.

A composite material in which an organic compound and an electron donor (donor) are mixed may also be used for the electron-injection layers (115, 115a, and 115b). Such a composite material is excellent in an electron-injection property and an electron-transport property because electrons are generated in the organic compound by the electron donor. The organic compound here is preferably a material excellent in transporting the generated electrons; specifically, for example, the electron-transport materials for forming the electron-transport layers (114, 114a, and 114b) (e.g., a metal complex or a heteroaromatic compound) can be used. As the electron donor, a substance showing an electron-donating property with respect to the organic compound may be used. Preferable examples are an alkali metal, an alkaline earth metal, and a rare earth metal. Specifically, lithium, cesium, magnesium, calcium, erbium, ytterbium, and the like can be given. Furthermore, an alkali metal oxide and an alkaline earth metal oxide are preferable, and a lithium oxide, a calcium oxide, a barium oxide, and the like can be given. Alternatively, a Lewis base such as magnesium oxide can be used. Further alternatively, an organic compound such as tetrathiafulvalene (abbreviation: TTF) can be used.

In the case where light obtained from the light-emitting layer 113b is amplified in the light-emitting element illustrated in FIG. 1D, the optical path length between the second electrode 102 and the light-emitting layer 113b is preferably less than one fourth of the wavelength λ of light emitted from the light-emitting layer 113b. In that case, the optical path length can be adjusted by changing the thickness of the electron-transport layer 114b or the electron-injection layer 115b.

<Charge Generation Layer>

In the light-emitting element illustrated in FIG. 1D, the charge generation layer 104 has a function of injecting electrons into the EL layer 103a and injecting holes into the EL layer 103b when a voltage is applied between the first electrode (anode) 101 and the second electrode (cathode) 102. The charge generation layer 104 may have either a structure in which an electron acceptor (acceptor) is added to a hole-transport material or a structure in which an electron donor (donor) is added to an electron-transport material. Alternatively, both of these structures may be stacked. Note that forming the charge generation layer 104 by using any of the above materials can suppress an increase in drive voltage caused by the stack of the EL layers.

In the case where the charge generation layer 104 has a structure in which an electron acceptor is added to a hole-transport material, any of the materials described in this embodiment can be used as the hole-transport material. As the electron acceptor, it is possible to use 7,7,8,8-tetracyano-2,3,5,6-tetrafluoroquinodimethane (abbreviation: $F_4$-TCNQ), chloranil, and the like. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, rhenium oxide, or the like is used.

In the case where the charge generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

<Substrate>

The light-emitting element described in this embodiment can be formed over any of a variety of substrates. Note that the type of the substrate is not limited to a certain type. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of a flexible substrate, an attachment film, and a base material film include plastics typified by polyethylene terephthalate (PET), polyethylene naphthalate (PEN), and polyether sulfone (PES); a synthetic resin such as acrylic; polypropylene; polyester; polyvinyl fluoride; polyvinyl chloride; polyamide; polyimide; aramid; epoxy; an inorganic vapor deposition film; and paper.

For fabrication of the light-emitting element in this embodiment, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layers (111a and 111b), the hole-transport layers (112a and 112b), the light-emitting layers (113a and 113b), the electron-transport layers (114a and 114b), the electron-injection layers (115a and 115b)) included in the EL layers and the charge generation layer 104 of the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, micro-contact printing, or nanoimprint lithography), or the like.

Note that materials that can be used for the functional layers (the hole-injection layers (111a and 111b), the hole-transport layers (112a and 112b), the light-emitting layers (113a and 113b), the electron-transport layers (114a and 114b), and the electron-injection layers (115a and 115b)) that are included in the EL layers (103a and 103b) and the charge generation layer 104 in the light-emitting element described in this embodiment are not limited to the above materials, and other materials can be used in combination as long as the functions of the layers are fulfilled. For example, a high molecular compound (e.g., an oligomer, a dendrimer, or a polymer), a middle molecular compound (a compound between a low molecular compound and a high molecular compound with a molecular weight of 400 to 4000), an inorganic compound (e.g., a quantum dot material), or the like can be used. The quantum dot may be a colloidal quantum dot, an alloyed quantum dot, a core-shell quantum dot, a core quantum dot, or the like.

The structures described in this embodiment can be combined with any of the structures described in the other embodiments as appropriate.

Embodiment 3

Figure 2A:
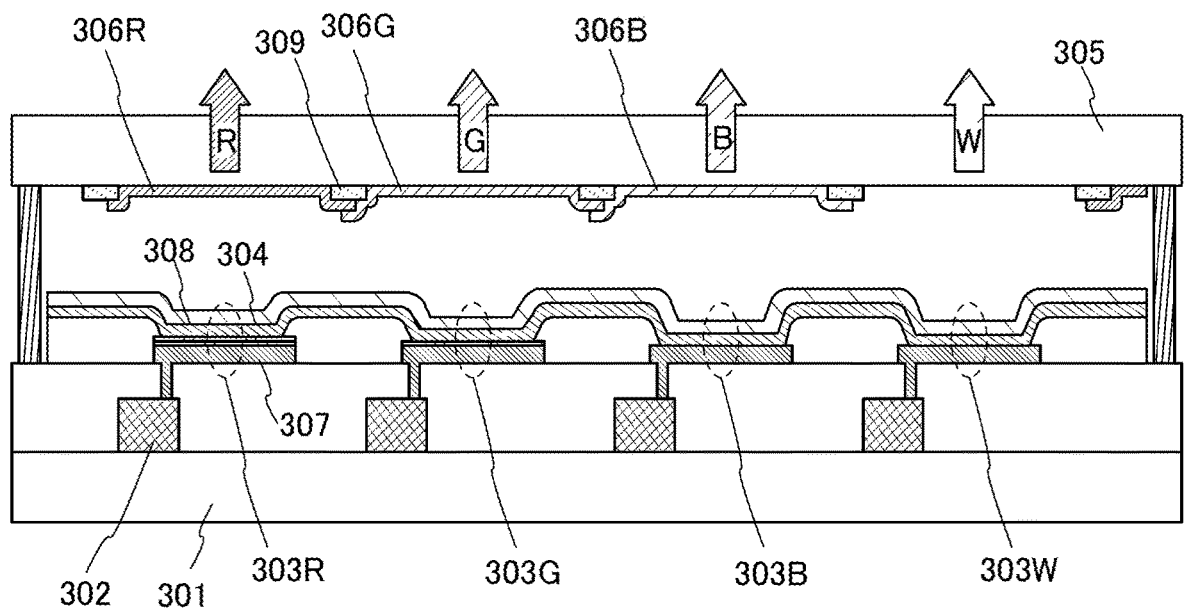
FIGS. 2A and 2B illustrate a light-emitting device.

In this embodiment, the light-emitting device of one embodiment of the present invention will be described with reference to FIG. 2A. Note that a light-emitting device illustrated in FIG. 2A is an active matrix light-emitting device in which transistors (FETs) 302 are electrically connected to light-emitting elements (303R, 303G, 303B, and 303W) over a first substrate 301. The light-emitting elements (303R, 303G, 303B, and 303W) include a common EL layer 304 and each have a microcavity structure in which the optical path length between electrodes is adjusted depending on the emission color of the light-emitting element. The light-emitting device is a top-emission light-emitting device in which light is emitted from the EL layer 304 through color filters (306R, 306G, and 306B) formed on a second substrate 305.

The light-emitting device illustrated in FIG. 2A is fabricated such that a first electrode 307 functions as a reflective electrode and a second electrode 308 functions as a transflective electrode. Note that description in any of the other embodiments can be referred to as appropriate for electrode materials for the first electrode 307 and the second electrode 308.

Figure 2B:
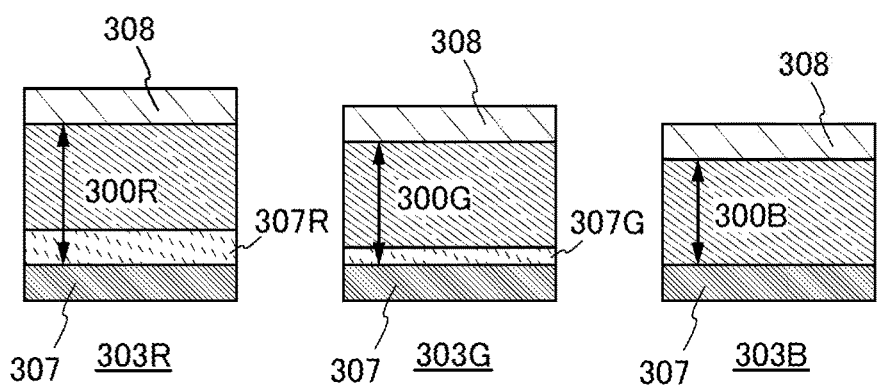

In the case where the light-emitting element 303R functions as a red light-emitting element, the light-emitting element 303G functions as a green light-emitting element, the light-emitting element 303B functions as a blue light-emitting element, and the light-emitting element 303W functions as a white light-emitting element in FIG. 2A, for example, a gap between the first electrode 307 and the second electrode 308 in the light-emitting element 303R is adjusted to have an optical path length 300R, a gap between the first electrode 307 and the second electrode 308 in the light-emitting element 303G is adjusted to have an optical path length 300G, and a gap between the first electrode 307 and the second electrode 308 in the light-emitting element 303B is adjusted to have an optical path length 300B as illustrated in FIG. 2B. Note that optical adjustment can be performed in such a manner that a conductive layer 307G is stacked over the first electrode 307 in the light-emitting element 303G and conductive layer 307R is stacked over the first electrode 307 in the light-emitting element 303R as illustrated in FIG. 2B.

The second substrate 305 is provided with the color filters (306R, 306G, and 306B). Note that the color filters each transmit visible light in a specific wavelength range and blocks visible light in a specific wavelength range. Thus, as illustrated in FIG. 2A, the color filter 306R that transmits only light in the red wavelength range is provided in a position overlapping with the light-emitting element 303R, whereby red light emission can be obtained from the light-emitting element 303R. Furthermore, the color filter 306G that transmits only light in the green wavelength range is provided in a position overlapping with the light-emitting element 303G, whereby green light emission can be obtained from the light-emitting element 303G. Moreover, the color filter 306B that transmits only light in the blue wavelength range is provided in a position overlapping with the light-emitting element 303B, whereby blue light emission can be obtained from the light-emitting element 303B. Note that the light-emitting element 303W can emit white light without a color filter. Note that a black layer (black matrix) 309 may be provided at an end portion of each color filter. The color filters (306R, 306G, and 306B) and the black layer 309 may be covered with an overcoat layer formed using a transparent material.

Although the light-emitting device in FIG. 2A has a structure in which light is extracted from the second substrate 305 side (top emission structure), a structure in which light is extracted from the first substrate 301 side where the FETs 302 are formed (bottom emission structure) may be employed. Note that in the light-emitting device having a top emission structure, the first substrate 301 can be a light-blocking substrate or a light-transmitting substrate, whereas in a light-emitting device having a bottom emission structure, the first substrate 301 needs to be a light-transmitting substrate.

In FIG. 2A, the light-emitting elements are the red light-emitting element, the green light-emitting element, the blue light-emitting element, and the white light-emitting element; however, the light-emitting elements of one embodiment of the present invention are not limited to the above, and a yellow light-emitting element or an orange light-emitting element may be used. Note that description in any of the other embodiments can be referred to as appropriate for materials that are used for the EL layers (a light-emitting layer, a hole-injection layer, a hole-transport layer, an electron-transport layer, an electron-injection layer, a charge generation layer, and the like) to fabricate each of the light-emitting elements. In that case, a color filter needs to be appropriately selected depending on the emission color of the light-emitting element.

With the above structure, a light-emitting device including light-emitting elements that exhibit a plurality of emission colors can be fabricated.

Note that the structures described in this embodiment can be combined with any of the structures described in the other embodiments as appropriate.

Embodiment 4

In this embodiment, a light-emitting device that is one embodiment of the present invention will be described.

The use of the element structure of the light-emitting element of one embodiment of the present invention allows fabrication of an active matrix light-emitting device or a passive matrix light-emitting device. Note that an active matrix light-emitting device has a structure including a combination of a light-emitting element and a transistor (FET). Thus, each of a passive matrix light-emitting device and an active matrix light-emitting device is one embodiment of the present invention. Note that any of the light-emitting elements described in other embodiments can be used in the light-emitting device described in this embodiment.

In this embodiment, an active matrix light-emitting device will be described with reference to FIGS. 3A and 3B.

Figure 3A:
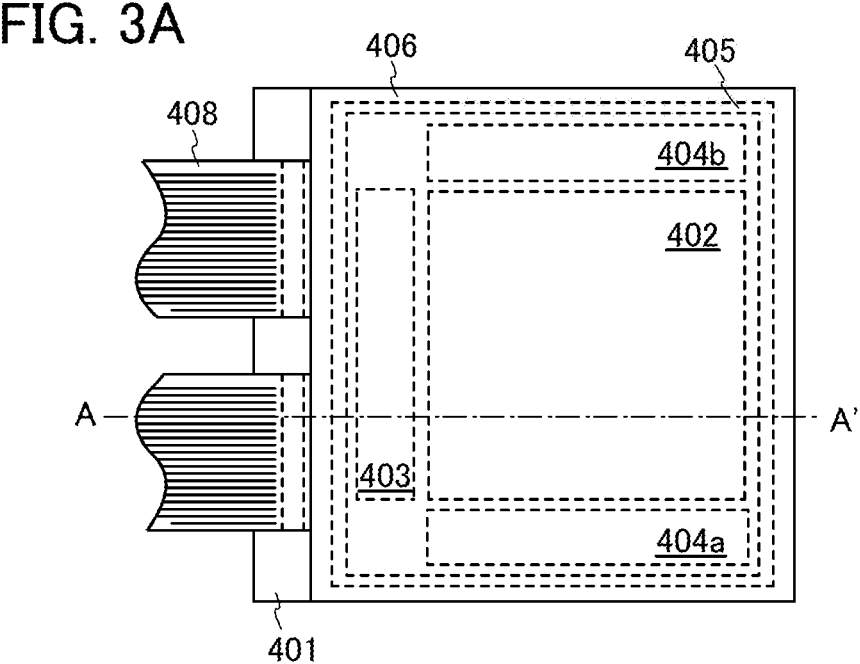
FIGS. 3A and 3B illustrate a light-emitting device.
Figure 3B:
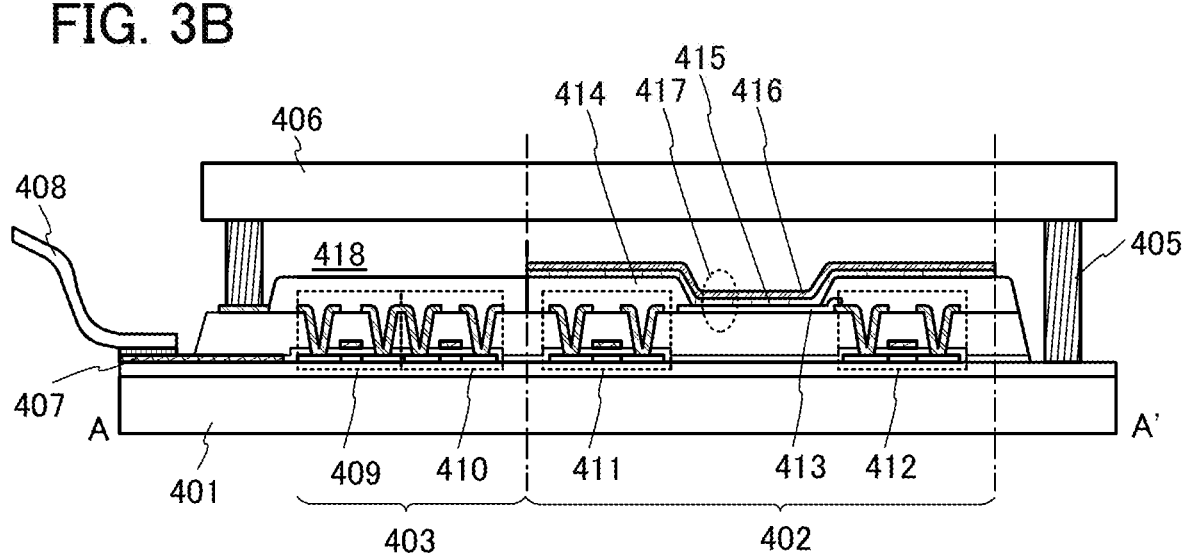

FIG. 3A is a top view illustrating the light-emitting device and FIG. 3B is a cross-sectional view taken along chain line A-A' in FIG. 3A. The active matrix light-emitting device includes a pixel portion 402, a driver circuit portion (source line driver circuit) 403, and driver circuit portions (gate line driver circuits) (404a and 404b) that are provided over a first substrate 401. The pixel portion 402 and the driver circuit portions (403, 404a, and 404b) are sealed between the first substrate 401 and a second substrate 406 with a sealant 405.

A lead wiring 407 is provided over the first substrate 401. The lead wiring 407 is connected to an FPC 408 that is an external input terminal. Note that the FPC 408 transmits a signal (e.g., a video signal, a clock signal, a start signal, or a reset signal) or a potential from the outside to the driver circuit portions (403, 404a, and 404b). The FPC 408 may be provided with a printed wiring board (PWB). Note that the light-emitting device provided with an FPC or a PWB is included in the category of a light-emitting device.

FIG. 3B illustrates a cross-sectional structure of the light-emitting device.

The pixel portion 402 includes a plurality of pixels each of which includes an FET (switching FET) 411, an FET (current control FET) 412, and a first electrode 413 electrically connected to the FET 412. Note that the number of FETs included in each pixel is not particularly limited and can be set appropriately.

As FETs 409, 410, 411, and 412, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 409, 410, 411, and 412, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be suppressed.

For the semiconductor, a Group 14 element, a compound semiconductor, an oxide semiconductor, an organic semiconductor, or the like can be used, for example. As a typical example, a semiconductor containing silicon, a semiconductor containing gallium arsenide, or an oxide semiconductor containing indium can be used.

The driver circuit portion 403 includes the FET 409 and the FET 410. The FET 409 and the FET 410 may be formed with a circuit including transistors having the same conductivity type (either n-channel transistors or p-channel transistors) or a CMOS circuit including an n-channel transistor and a p-channel transistor. Furthermore, a driver circuit may be provided outside.

An end portion of the first electrode 413 is covered with an insulator 414. The insulator 414 can be formed using an organic compound such as a negative photosensitive resin or a positive photosensitive resin (acrylic resin), or an inorganic compound such as silicon oxide, silicon oxynitride, or silicon nitride. The insulator 414 preferably has a curved surface with curvature at an upper end portion or a lower end portion thereof. In that case, favorable coverage with a film formed over the insulator 414 can be obtained.

An EL layer 415 and a second electrode 416 are stacked over the first electrode 413. The EL layer 415 includes a light-emitting layer, a hole-injection layer, a hole-transport layer, an electron-transport layer, an electron-injection layer, a charge generation layer, and the like.

The structure and materials described in any of the other embodiments can be used for the components of a light-emitting element 417 described in this embodiment. Although not illustrated, the second electrode 416 is electrically connected to the FPC 408 that is an external input terminal.

Although the cross-sectional view in FIG. 3B illustrates only one light-emitting element 417, a plurality of light-emitting elements are arranged in a matrix in the pixel portion 402. Light-emitting elements that emit light of three kinds of colors (R, G, and B) are selectively formed in the pixel portion 402, whereby a light-emitting device capable of displaying a full-color image can be obtained. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of some of the above colors are used in combination with the light-emitting elements that emit light of three kinds of colors (R, G, and B), whereby effects such as an improvement in color purity and a reduction in power consumption can be achieved. Alternatively, a light-emitting device which is capable of displaying a full-color image may be fabricated by a combination with color filters.

When the second substrate 406 and the first substrate 401 are bonded to each other with the sealant 405, the FETs (409, 410, 411, and 412) and the light-emitting element 417 over the first substrate 401 are provided in a space 418 surrounded by the first substrate 401, the second substrate 406, and the sealant 405. Note that the space 418 may be filled with an inert gas (e.g., nitrogen or argon) or an organic substance (including the sealant 405).

An epoxy-based resin, glass frit, or the like can be used for the sealant 405. It is preferable to use a material that is permeable to as little moisture and oxygen as possible for the sealant 405. As the second substrate 406, a substrate that can be used as the first substrate 401 can be similarly used. Thus, any of the various substrates described in the other embodiments can be appropriately used. As the substrate, a glass substrate, a quartz substrate, or a plastic substrate made of fiber reinforced plastic (FRP), polyvinyl fluoride (PVF), polyester, acrylic, or the like can be used. In the case where glass frit is used for the sealant, the first substrate 401 and the second substrate 406 are preferably glass substrates in terms of adhesion.

Accordingly, the active matrix light-emitting device can be obtained.

In the case where the active matrix light-emitting device is provided over a flexible substrate, the FETs and the light-emitting element may be directly formed over the flexible substrate; alternatively, the FETs and the light-emitting element may be formed over a substrate provided with a separation layer and then separated at the separation layer by application of heat, force, laser, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. With the use of any of these substrates, an increase in durability, an increase in heat resistance, a reduction in weight, and a reduction in thickness can be achieved.

Note that the structures described in this embodiment can be combined with any of the structures described in the other embodiments as appropriate.

Embodiment 5

In this embodiment, examples of a variety of electronic devices and an automobile manufactured using a light-emitting device of one embodiment of the present invention will be described.

Examples of the electronic device including the light-emitting device are television devices (also referred to as TV or television receivers), monitors for computers and the like, cameras such as digital cameras and digital video cameras, digital photo frames, cellular phones (also referred to as mobile phones or portable telephone devices), portable game machines, portable information terminals, audio playback devices, large game machines such as pachinko machines, and the like. Specific examples of the electronic devices are illustrated in FIGS. 4A, 4B, 4C, 4D, 4D'-1, and 4D'-2 and FIGS. 5A to 5C.

Figure 4A:
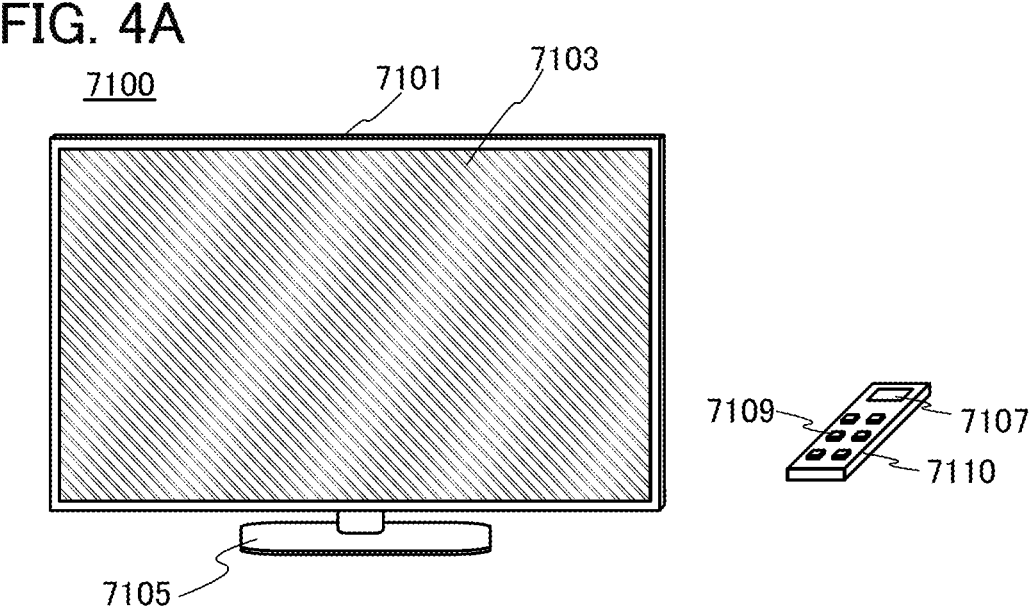
FIGS. 4A, 4B, 4C, 4D, 4D'-1, and 4D'-2 illustrate electronic devices.

FIG. 4A illustrates an example of a television device. In a television device 7100, a display portion 7103 is incorporated in a housing 7101. The display portion 7103 can display images and may be a touch panel (input/output device) including a touch sensor (input device). Note that the light-emitting device of one embodiment of the present invention can be used for the display portion 7103. In addition, here, the housing 7101 is supported by a stand 7105.

The television device 7100 can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

Figure 4B:
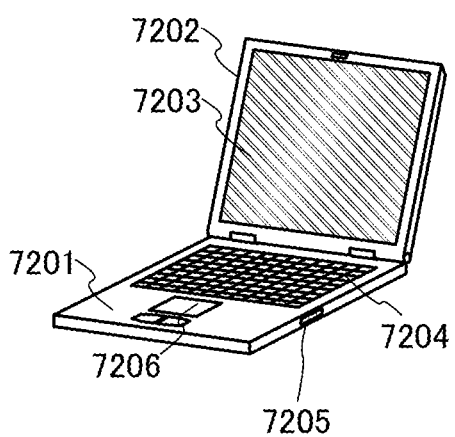

FIG. 4B illustrates a computer, which includes a main body 7201, a housing 7202, a display portion 7203, a keyboard 7204, an external connection port 7205, a pointing device 7206, and the like. Note that this computer can be manufactured using the light-emitting device of one embodiment of the present invention for the display portion 7203. The display portion 7203 may be a touch panel (input/output device) including a touch sensor (input device).

Figure 4C:
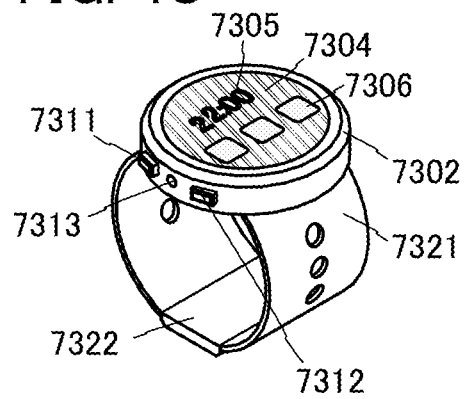

FIG. 4C illustrates a smart watch, which includes a housing 7302, a display portion 7304, operation buttons 7311 and 7312, a connection terminal 7313, a band 7321, a clasp 7322, and the like.

The display portion 7304 mounted in the housing 7302 serving as a bezel includes a non-rectangular display region. The display portion 7304 can display an icon 7305 indicating time, another icon 7306, and the like. The display portion 7304 may be a touch panel (input/output device) including a touch sensor (input device).

The smart watch illustrated in FIG. 4C can have a variety of functions, such as a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display portion 7304.

Figure 4D:
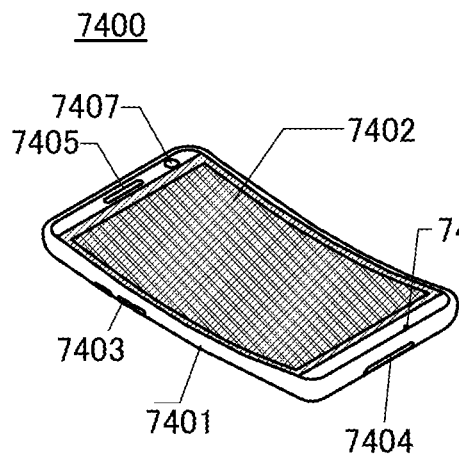
Figure 4D:
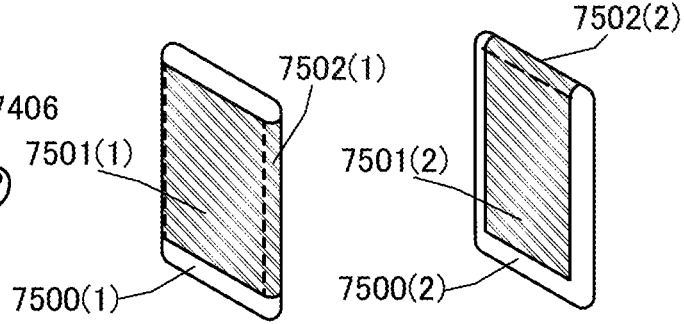

FIG. 4D illustrates an example of a cellular phone (e.g., smartphone). A cellular phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming the light-emitting element of one embodiment of the present invention over a flexible substrate, the light-emitting device can be used for the display portion 7402 having a curved surface as illustrated in FIG. 4D.

When the display portion 7402 of the cellular phone 7400 illustrated in FIG. 4D is touched with a finger or the like, data can be input to the cellular phone 7400. In addition, operations such as making a call and composing e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or composing e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyroscope sensor or an acceleration sensor is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, by providing a backlight or a sensing light source that emits near-infrared light in the display portion, an image of a finger vein, a palm vein, or the like can be taken.

The light-emitting device can be used for a cellular phone having a structure illustrated in FIG. 4D'-1 or FIG. 4D'-2, which is another structure of the cellular phone (e.g., smartphone).

Note that in the case of the structure illustrated in FIG. 4D'-1 or FIG. 4D'-2, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the cellular phone is placed in the user's breast pocket.

Figure 5A:
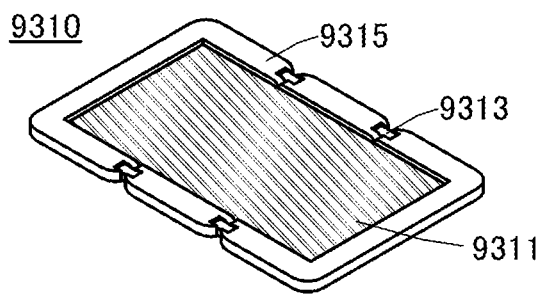
FIGS. 5A to 5C illustrate an electronic device.
Figure 5B:
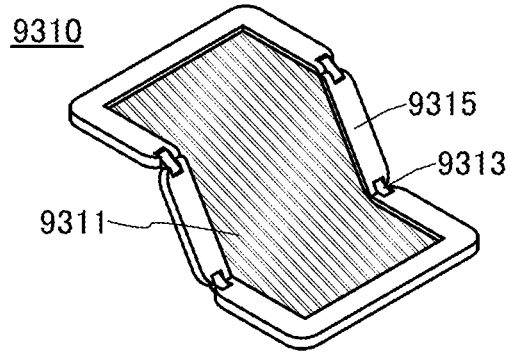
Figure 5C:
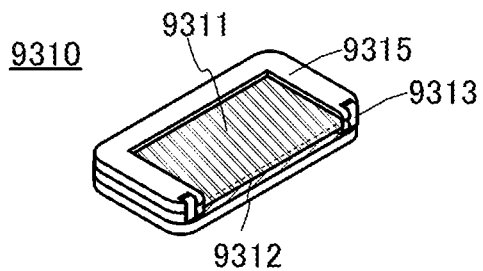

Another electronic device including a light-emitting device is a foldable portable information terminal illustrated in FIGS. 5A to 5C. FIG. 5A illustrates a portable information terminal 9310 which is opened. FIG. 5B illustrates the portable information terminal 9310 which is being opened or being folded. FIG. 5C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (input/output device) including a touch sensor (input device). By bending the display portion 9311 at a connection portion between two housings 9315 with the use of the hinges 9313, the portable information terminal 9310 can be reversibly changed in shape from an opened state to a folded state. The light-emitting device of one embodiment of the present invention can be used for the display portion 9311. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application and the like can be smoothly performed.

Figure 6A:
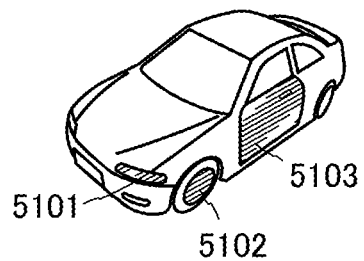
FIGS. 6A and 6B illustrate an automobile.
Figure 6B:
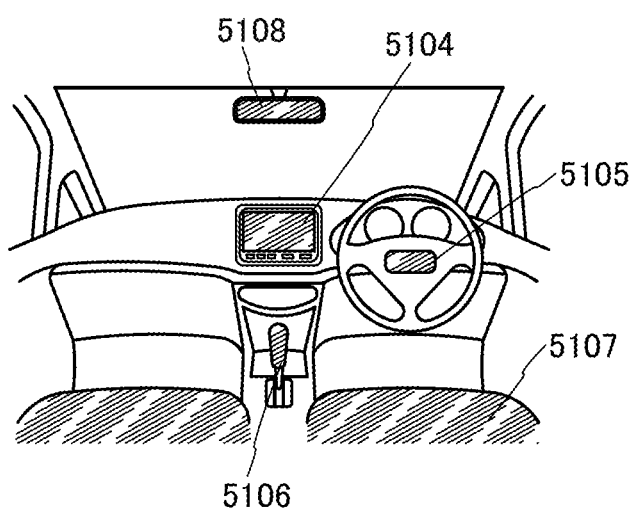

FIGS. 6A and 6B illustrate an automobile including a light-emitting device. The light-emitting device can be incorporated in the automobile, and specifically, can be included in lights 5101 (including lights of the rear part of the car), a wheel cover 5102, a part or the whole of a door 5103, or the like on the outer side of the automobile which is illustrated in FIG. 6A. The light-emitting device can also be included in a display portion 5104, a steering wheel 5105, a gear lever 5106, a seat 5107, an inner rearview mirror 5108, or the like on the inner side of the automobile which is illustrated in FIG. 6B, or in a part of a glass window.

As described above, the electronic devices and the automobile can be obtained using the light-emitting device of one embodiment of the present invention. Note that the light-emitting device can be used for electronic devices and automobiles in a variety of fields without being limited to those described in this embodiment.

Note that the structures described in this embodiment can be combined with any of the structures described in the other embodiments as appropriate.

Embodiment 6

In this embodiment, the structures of lighting devices each fabricated using the light-emitting element of one embodiment of the present invention will be described with reference to FIGS. 7A to 7D.

Figure 7A:
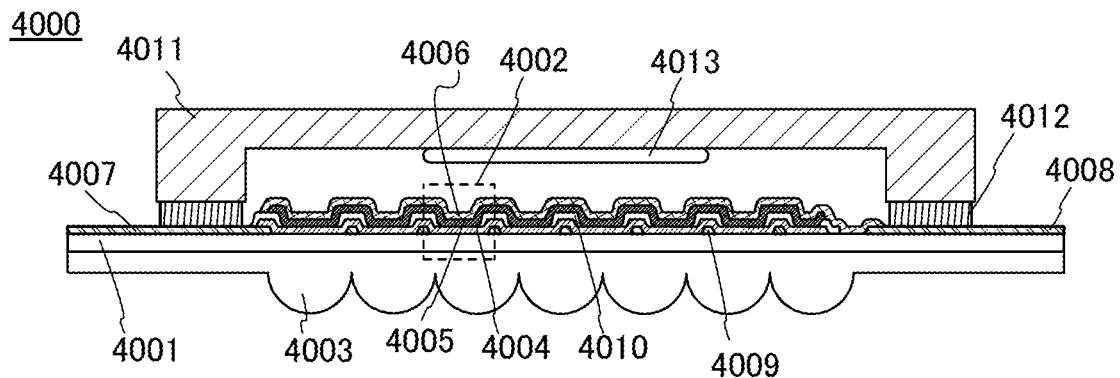
FIGS. 7A to 7D each illustrate a lighting device.
Figure 7B:
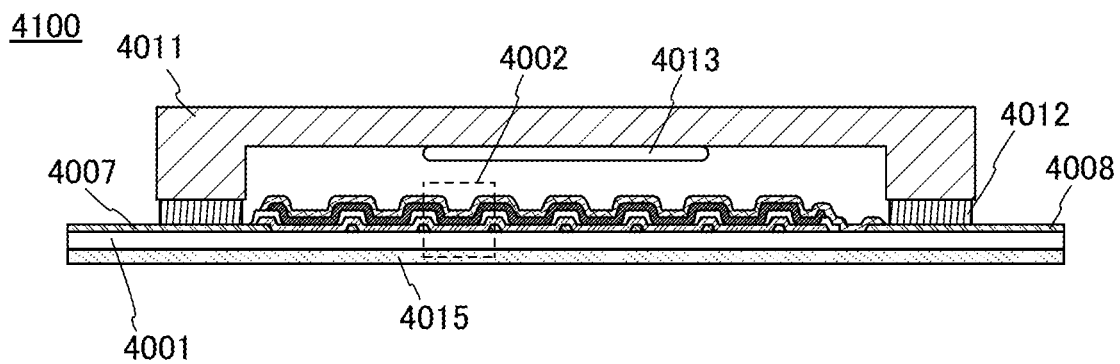
Figure 7C:
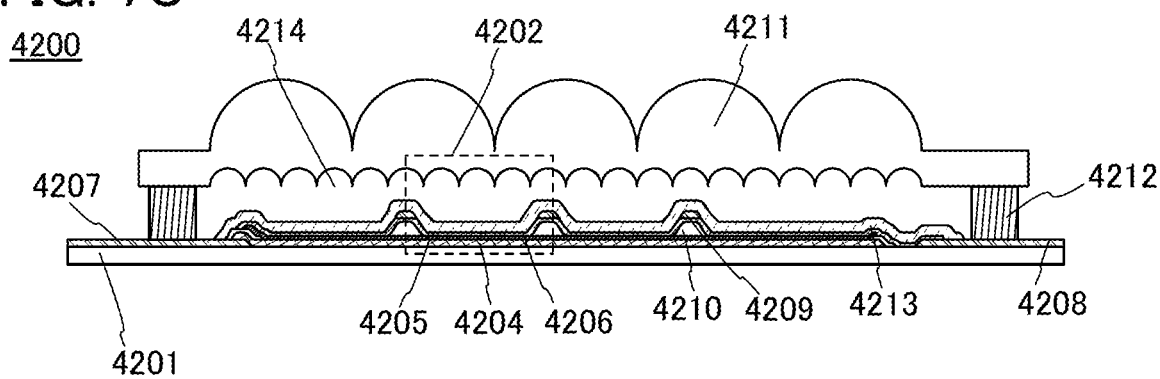
Figure 7D:
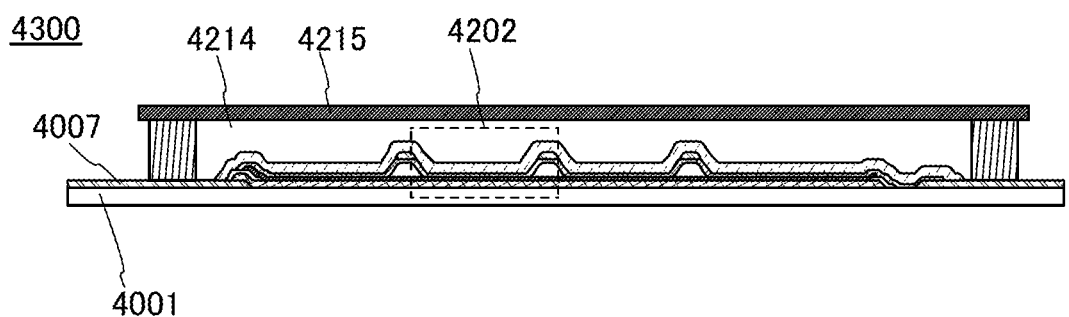

FIGS. 7A to 7D are examples of cross-sectional views of lighting devices. FIGS. 7A and 7B illustrate bottom-emission lighting devices in which light is extracted from the substrate side, and FIGS. 7C and 7D illustrate top-emission lighting devices in which light is extracted from the sealing substrate side.

A lighting device 4000 illustrated in FIG. 7A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting element 4002. The substrate 4003 has the unevenness illustrated in FIG. 7A, whereby the extraction efficiency of light emitted from the light-emitting element 4002 can be increased.

Instead of the substrate 4003, a diffusion plate 4015 may be provided on the outside of the substrate 4001 as in a lighting device 4100 illustrated in FIG. 7B.

A lighting device 4200 illustrated in FIG. 7C includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting element 4202. The sealing substrate 4211 has the unevenness illustrated in FIG. 7C, whereby the extraction efficiency of light emitted from the light-emitting element 4202 can be increased.

Instead of the sealing substrate 4211, a diffusion plate 4215 may be provided over the light-emitting element 4202 as in a lighting device 4300 illustrated in FIG. 7D.

Note that the EL layers 4005 and 4205 in this embodiment can include the organic compound of one embodiment of the present invention.

Note that the structures described in this embodiment can be combined with any of the structures described in the other embodiments as appropriate.

Embodiment 7

Figure 8:
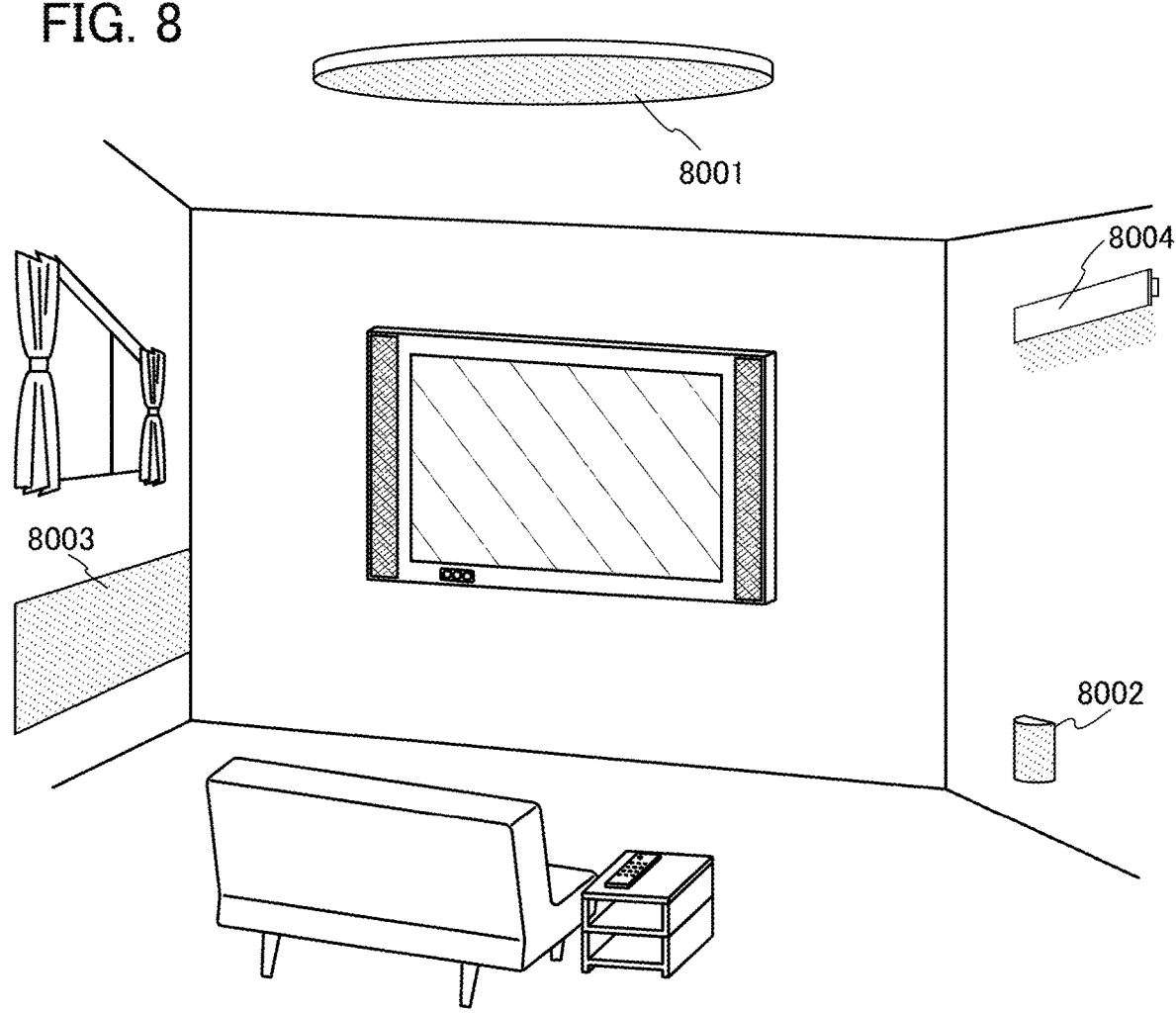
FIG. 8 illustrates lighting devices.

In this embodiment, application examples of a lighting device fabricated using the light-emitting element of one embodiment of the present invention will be described with reference to FIG. 8.

A ceiling light 8001 can be used as an indoor lighting device. Examples of the ceiling light 8001 include a direct-mount light and an embedded light. Besides, application to a cord pendant light (light that is suspended from a ceiling by a cord) is also possible.

A foot light 8002 lights a floor so that safety on the floor can be improved. For example, it can be effectively used in a bedroom, on a staircase, or on a passage. In that case, the size or shape of the foot light can be changed depending on the area or structure of a room.

A sheet-like lighting 8003 is a thin sheet-like lighting device. The sheet-like lighting, which is attached to a wall when used, is space-saving and thus can be used for a wide variety of uses. Furthermore, the area of the sheet-like lighting can be increased. The sheet-like lighting can also be used on a wall or housing having a curved surface.

In addition, a lighting device 8004 in which the direction of light from a light source is controlled to be only a desired direction can be used.

Besides the above examples, when the light-emitting device of one embodiment of the present invention is used as part of furniture in a room, a lighting device that functions as the furniture can be obtained.

As described above, a variety of lighting devices that include the light-emitting device can be obtained. Note that these lighting devices are also embodiments of the present invention.

The structures described in this embodiment can be combined with any of the structures described in the other embodiments as appropriate.

Embodiment 8

In this embodiment, touch panels including the light-emitting element of one embodiment of the present invention or the light-emitting device of one embodiment of the present invention will be described with reference to FIGS. 9A and 9B, FIGS. 10A and 10B, FIGS. 11A and 11B, FIGS. 12A and 12B, and FIG. 13.

Figure 9A:
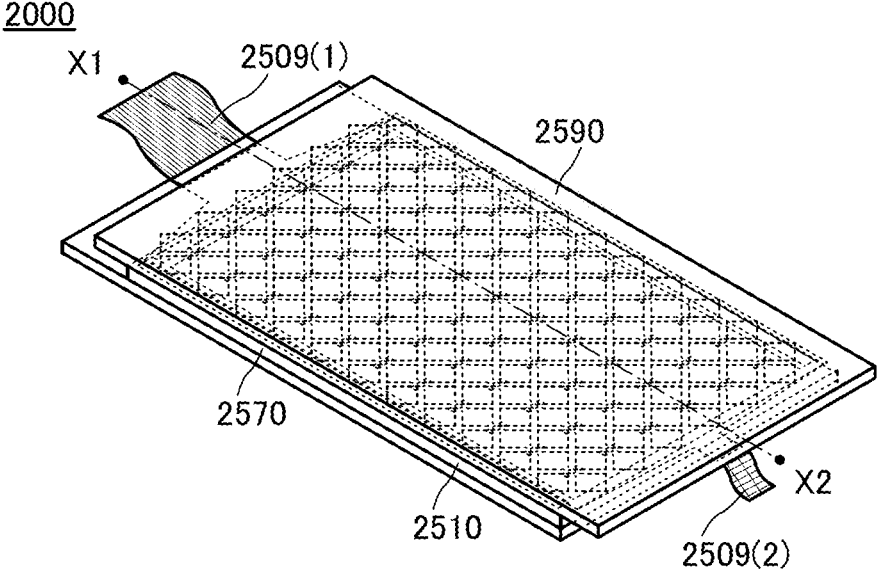
FIGS. 9A and 9B illustrate an example of a touch panel.
Figure 9B:
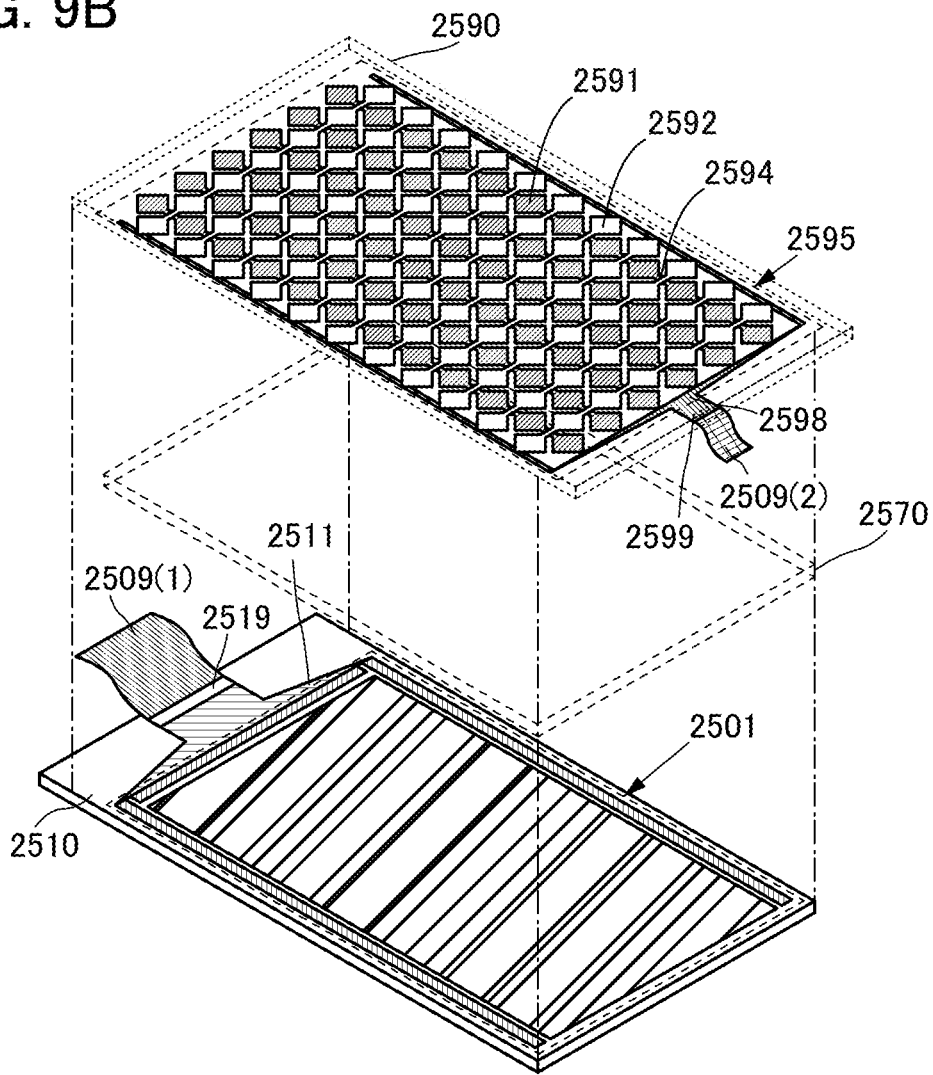

FIGS. 9A and 9B are perspective views of a touch panel 2000. Note that FIGS. 9A and 9B illustrate only main components of the touch panel 2000 for simplicity.

The touch panel 2000 includes a display panel 2501 and a touch sensor 2595 (see FIG. 9B). The touch panel 2000 includes a substrate 2510, a substrate 2570, and a substrate 2590.

The display panel 2501 includes, over the substrate 2510, a plurality of pixels and a plurality of wirings 2511 through which signals are supplied to the pixels. The plurality of wirings 2511 are led to a peripheral portion of the substrate 2510, and parts of the plurality of wirings 2511 form a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and parts of the plurality of wirings 2598 form a terminal 2599. The terminal 2599 is electrically connected to an FPC 2509(2). Note that in FIG. 9B, electrodes, wirings, and the like of the touch sensor 2595 provided on the back side of the substrate 2590 (the side facing the substrate 2570) are indicated by solid lines for clarity.

As the touch sensor 2595, a capacitive touch sensor can be used, for example. Examples of the capacitive touch sensor include a surface capacitive touch sensor, a projected capacitive touch sensor, and the like.

Examples of the projected capacitive touch sensor are a self-capacitive touch sensor, a mutual capacitive touch sensor, and the like, which differ mainly in the driving method. The use of a mutual capacitive type is preferable because multiple points can be sensed simultaneously.

First, an example of using a projected capacitive touch sensor will be described below with reference to FIG. 9B. Note that in the case of a projected capacitive touch sensor, a variety of sensors that can sense proximity or touch of a sensing target such as a finger can be used.

The projected capacitive touch sensor 2595 includes electrodes 2591 and electrodes 2592. The electrodes 2591 are electrically connected to any of the plurality of wirings 2598, and the electrodes 2592 are electrically connected to any of the other wirings 2598. The electrodes 2592 each have a shape of a plurality of quadrangles arranged in one direction with one corner of a quadrangle connected to one corner of another quadrangle with a wiring 2594, as illustrated in FIGS. 9A and 9B. In the same manner, the electrodes 2591 each have a shape of a plurality of quadrangles arranged with one corner of a quadrangle connected to one corner of another quadrangle; however, the direction in which the electrodes 2591 are connected is a direction crossing the direction in which the electrodes 2592 are connected. Note that the direction in which the electrodes 2591 are connected and the direction in which the electrodes 2592 are connected are not necessarily perpendicular to each other, and the electrodes 2591 may be arranged to intersect with the electrodes 2592 at an angle greater than 0° and less than 90°.

The intersecting area of the electrode 2592 and the wiring 2594 is preferably as small as possible. Such a structure allows a reduction in the area of a region where the electrodes are not provided, reducing variation in transmittance. As a result, variation in luminance of light passing through the touch sensor 2595 can be reduced.

Note that the shapes of the electrodes 2591 and the electrodes 2592 are not limited thereto and can be any of a variety of shapes. For example, the plurality of electrodes 2591 may be provided so that a space between the electrodes 2591 is reduced as much as possible, and the plurality of electrodes 2592 may be provided with an insulating layer located between the electrodes 2591 and 2592. In this case, it is preferable to provide, between two adjacent electrodes 2592, a dummy electrode electrically insulated from these electrodes because the area of regions having different transmittances can be reduced.

Figure 10A:
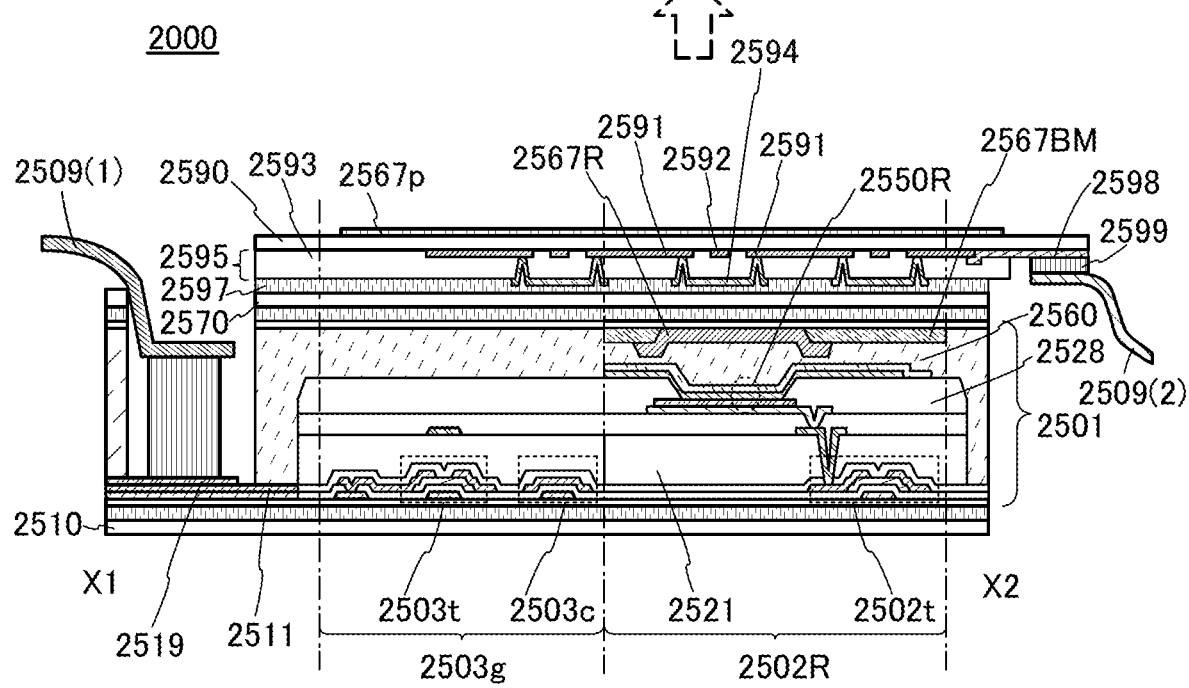
FIGS. 10A and 10B illustrate an example of a touch panel.
Figure 10B:
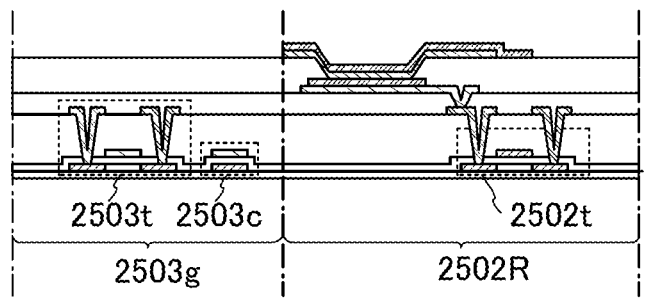

Next, the touch panel 2000 will be described in detail with reference to FIGS. 10A and 10B. FIGS. 10A and 10B correspond to cross-sectional views taken along dashed-dotted line X1-X2 in FIG. 9A.

The touch panel 2000 includes the touch sensor 2595 and the display panel 2501.

The touch sensor 2595 includes the electrodes 2591 and the electrodes 2592 provided in a staggered arrangement in contact with the substrate 2590, an insulating layer 2593 covering the electrodes 2591 and the electrodes 2592, and the wiring 2594 that electrically connects the adjacent electrodes 2591 to each other. Between the adjacent electrodes 2591, the electrode 2592 is provided.

The electrodes 2591 and the electrodes 2592 can be formed using a light-transmitting conductive material. As a light-transmitting conductive material, a conductive oxide such as indium oxide, indium tin oxide, indium zinc oxide, zinc oxide, or zinc oxide to which gallium is added can be used. A graphene compound may be used as well. When a graphene compound is used, it can be formed, for example, by reducing a graphene oxide film. As a reducing method, a method with application of heat, a method with laser irradiation, or the like can be employed.

For example, the electrodes 2591 and 2592 can be formed by depositing a light-transmitting conductive material on the substrate 2590 by a sputtering method and then removing an unneeded portion by any of various patterning techniques such as photolithography.

Examples of a material for the insulating layer 2593 include a resin such as an acrylic resin or an epoxy resin, a resin having a siloxane bond, and an inorganic insulating material such as silicon oxide, silicon oxynitride, or aluminum oxide.

The adjacent electrodes 2591 are electrically connected to each other with the wiring 2594 formed in part of the insulating layer 2593. Note that a material for the wiring 2594 preferably has higher conductivity than materials for the electrodes 2591 and 2592 to reduce electrical resistance.

The wiring 2598 is electrically connected to any of the electrodes 2591 and 2592. Part of the wiring 2598 functions as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Through the terminal 2599, the wiring 2598 and the FPC 2509(2) are electrically connected to each other. The terminal 2599 can be formed using any of various kinds of anisotropic conductive films (ACF), anisotropic conductive pastes (ACP), and the like.

An adhesive layer 2597 is provided in contact with the wiring 2594. That is, the touch sensor 2595 is attached to the display panel 2501 so that they overlap with each other with the adhesive layer 2597 provided therebetween. Note that the substrate 2570 as illustrated in FIG. 10A may be provided over the surface of the display panel 2501 that is in contact with the adhesive layer 2597; however, the substrate 2570 is not always needed.

The adhesive layer 2597 has a light-transmitting property. For example, a thermosetting resin or an ultraviolet curable resin can be used; specifically, a resin such as an acrylic resin, a urethane-based resin, an epoxy-based resin, or a siloxane-based resin can be used.

The display panel 2501 in FIG. 10A includes, between the substrate 2510 and the substrate 2570, a plurality of pixels arranged in a matrix and a driver circuit. Each pixel includes a light-emitting element and a pixel circuit that drives the light-emitting element.

In FIG. 10A, a pixel 2502R is shown as an example of the pixel of the display panel 2501, and a scan line driver circuit 2503g is shown as an example of the driver circuit.

The pixel 2502R includes a light-emitting element 2550R and a transistor 2502t that can supply electric power to the light-emitting element 2550R.

The transistor 2502t is covered with an insulating layer 2521. The insulating layer 2521 has a function of providing a flat surface by covering unevenness caused by the transistor and the like that have been already formed. The insulating layer 2521 may serve also as a layer for preventing diffusion of impurities. That is preferable because a reduction in the reliability of the transistor or the like due to diffusion of impurities can be prevented.

The light-emitting element 2550R is electrically connected to the transistor 2502t through a wiring. It is one electrode of the light-emitting element 2550R that is directly connected to the wiring. An end portion of the one electrode of the light-emitting element 2550R is covered with an insulator 2528.

The light-emitting element 2550R includes an EL layer between a pair of electrodes. A coloring layer 2567R is provided to overlap with the light-emitting element 2550R, and part of light emitted from the light-emitting element 2550R is transmitted through the coloring layer 2567R and extracted in the direction indicated by an arrow in the drawing. A light-blocking layer 2567BM is provided at an end portion of the coloring layer, and a sealing layer 2560 is provided between the light-emitting element 2550R and the coloring layer 2567R.

Note that when the sealing layer 2560 is provided on the side from which light from the light-emitting element 2550R is extracted, the sealing layer 2560 preferably has a light-transmitting property. The sealing layer 2560 preferably has a higher refractive index than the air.

The scan line driver circuit 2503g includes a transistor 2503t and a capacitor 2503c. Note that the driver circuit and the pixel circuits can be formed in the same process over the same substrate. Thus, in a manner similar to that of the transistor 2502t in the pixel circuit, the transistor 2503t in the driver circuit (the scan line driver circuit 2503g) is also covered with the insulating layer 2521.

The wirings 2511 through which a signal can be supplied to the transistor 2503t are provided. The terminal 2519 is provided in contact with the wiring 2511. The terminal 2519 is electrically connected to the FPC 2509(1), and the FPC 2509(1) has a function of supplying signals such as an image signal and a synchronization signal. Note that a printed wiring board (PWB) may be attached to the FPC 2509(1).

Although the case where the display panel 2501 illustrated in FIG. 10A includes a bottom-gate transistor is described, the structure of the transistor is not limited thereto, and any of transistors with various structures can be used. In each of the transistors 2502t and 2503t illustrated in FIG. 10A, a semiconductor layer containing an oxide semiconductor can be used for a channel region. Alternatively, a semiconductor layer containing amorphous silicon or a semiconductor layer containing polycrystalline silicon that is obtained by crystallization process such as laser annealing can be used for a channel region.

FIG. 10B illustrates the structure that includes a top-gate transistor instead of the bottom-gate transistor illustrated in FIG. 10A. The kind of the semiconductor layer that can be used for the channel region does not depend on the structure of the transistor.

In the touch panel 2000 illustrated in FIG. 10A, an anti-reflection layer 2567p overlapping with at least the pixel is preferably provided on a surface of the touch panel on the side from which light from the pixel is extracted, as illustrated in FIG. 10A. As the anti-reflection layer 2567p, a circular polarizing plate or the like can be used.

For the substrates 2510, 2570, and 2590 in FIG. 10A, for example, a flexible material having a vapor permeability of $1 \times 10^{-5}$ g/(m$^2$-day) or lower, preferably $1 \times 10^{-6}$ g/(m$^2$-day) or lower, can be favorably used. Alternatively, it is preferable to use the materials that make these substrates have substantially the same coefficient of thermal expansion. For example, the coefficients of linear expansion of the materials are $1 \times 10^{-3}$/K or lower, preferably $5 \times 10^{-5}$/K or lower, and further preferably $1 \times 10^{-5}$/K or lower.

Next, a touch panel 2000' having a structure different from that of the touch panel 2000 illustrated in FIGS. 10A and 10B will be described with reference to FIGS. 11A and 11B. It can be used as a touch panel like the touch panel 2000.

Figure 11A:
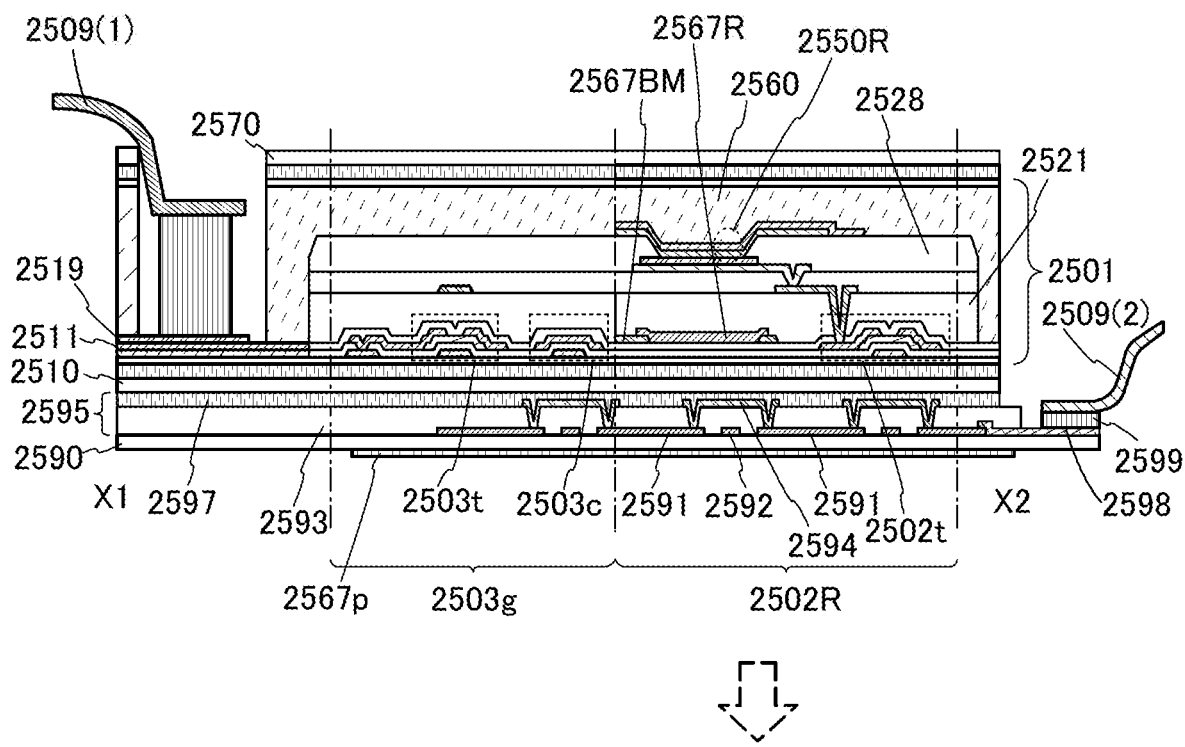
FIGS. 11A and 11B illustrate an example of a touch panel.
Figure 11B:
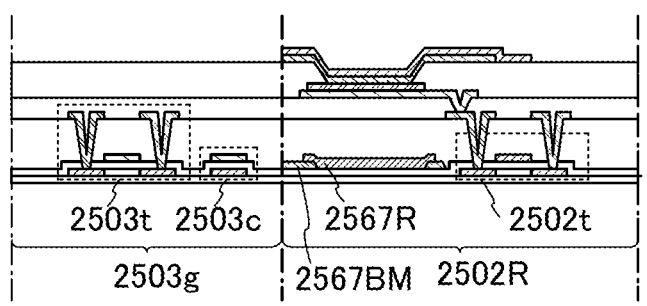

FIGS. 11A and 11B are cross-sectional views of the touch panel 2000'. In the touch panel 2000' illustrated in FIGS. 11A and 11B, the position of the touch sensor 2595 relative to the display panel 2501 is different from that in the touch panel 2000 illustrated in FIGS. 10A and 10B. Only different structures will be described below, and the above description of the touch panel 2000 can be referred to for the other similar structures.

The coloring layer 2567R overlaps with the light-emitting element 2550R. The light-emitting element 2550R illustrated in FIG. 11A emits light to the side where the transistor 2502t is provided. That is, (part of) light emitted from the light-emitting element 2550R passes through the coloring layer 2567R and is extracted in the direction indicated by an arrow in FIG. 11A. Note that the light-blocking layer 2567BM is provided at an end portion of the coloring layer 2567R.

The touch sensor 2595 is provided on the transistor 2502t side (the far side from the light-emitting element 2550R) of the display panel 2501 (see FIG. 11A).

The adhesive layer 2597 is in contact with the substrate 2510 of the display panel 2501 and attaches the display panel 2501 and the touch sensor 2595 to each other in the structure illustrated in FIG. 11A. The substrate 2510 is not necessarily provided between the display panel 2501 and the touch sensor 2595 that are attached to each other by the adhesive layer 2597.

As in the touch panel 2000, transistors with a variety of structures can be used for the display panel 2501 in the touch panel 2000'. Although a bottom-gate transistor is used in FIG. 11A, a top-gate transistor may be used as illustrated in FIG. 11B.

An example of a driving method of the touch panel will be described with reference to FIGS. 12A and 12B.

Figure 12A:
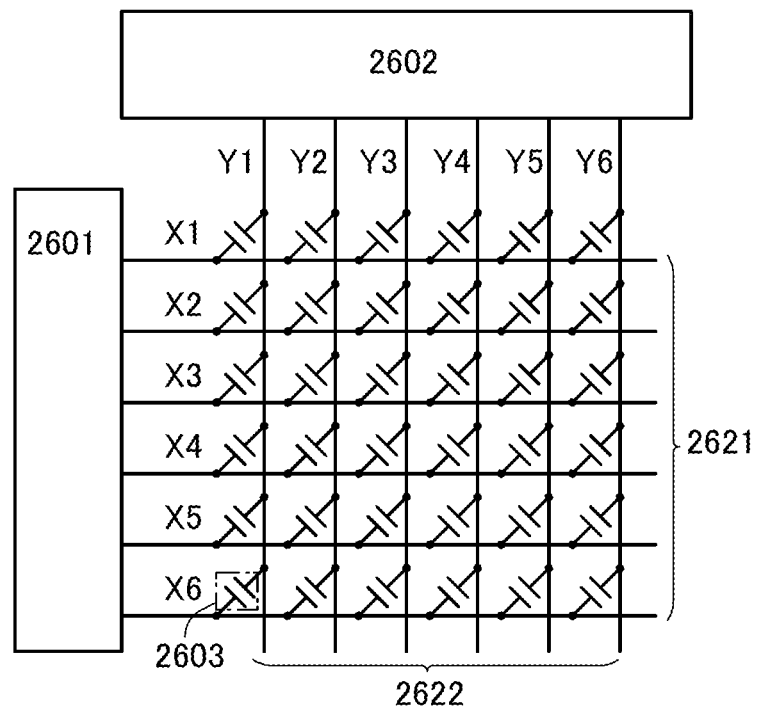
FIGS. 12A and 12B are a block diagram and a timing chart of a touch sensor.

FIG. 12A is a block diagram illustrating the structure of a mutual capacitive touch sensor. FIG. 12A illustrates a pulse voltage output circuit 2601 and a current sensing circuit 2602. Note that in FIG. 12A, six wirings X1 to X6 represent electrodes 2621 to which a pulse voltage is applied, and six wirings Y1 to Y6 represent electrodes 2622 that detect changes in current. FIG. 12A also illustrates capacitors 2603 that are each formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for detecting changes in current flowing through the wirings Y1 to Y6 that are caused by the change in mutual capacitance in the capacitor 2603. No change in current value is detected in the wirings Y1 to Y6 when there is no approach or contact of a sensing target, whereas a decrease in current value is detected when mutual capacitance is decreased owing to the approach or contact of a sensing target. Note that an integrator circuit or the like is used for sensing of current values.

Figure 12B:
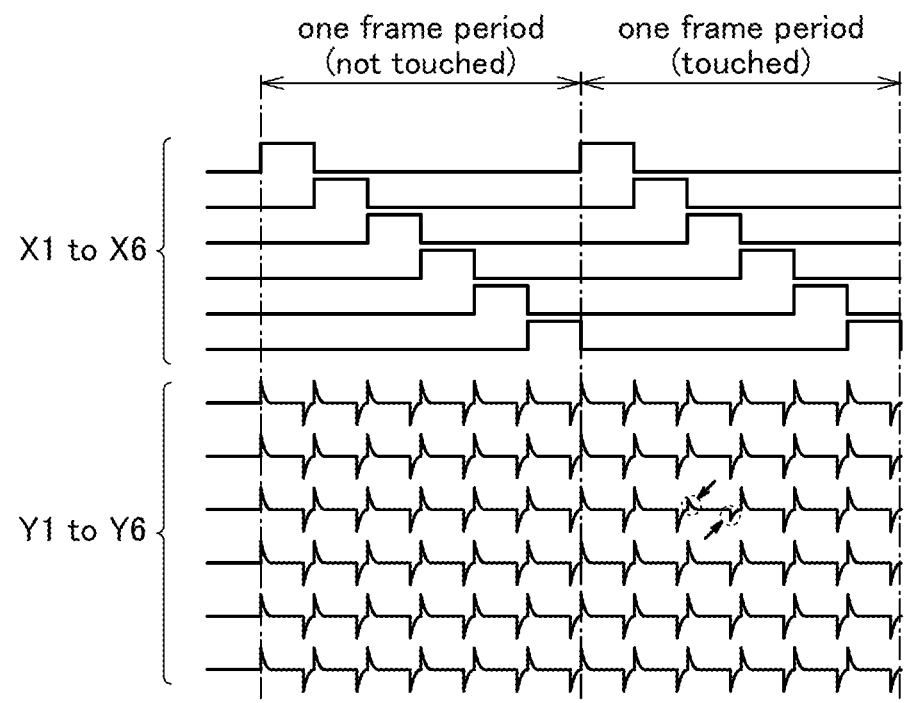

FIG. 12B is a timing chart showing input and output waveforms in the mutual capacitive touch sensor illustrated in FIG. 12A. In FIG. 12B, sensing of a sensing target is performed in all the rows and columns in one frame period. FIG. 12B shows a period when a sensing target is not sensed (not touched) and a period when a sensing target is sensed (touched). Sensed current values of the wirings Y1 to Y6 are shown as the waveforms of voltage values.

A pulse voltage is sequentially applied to the wirings X1 to X6, and the waveforms of the wirings Y1 to Y6 change in response to the pulse voltage. When there is no approach or contact of a sensing target, the waveforms of the wirings Y1 to Y6 change uniformly in response to changes in the voltages of the wirings X1 to X6. The current value is decreased at the point of approach or contact of a sensing target and accordingly the waveform of the voltage value changes. By detecting a change in mutual capacitance in this manner, the approach or contact of a sensing target can be sensed.

Figure 13:
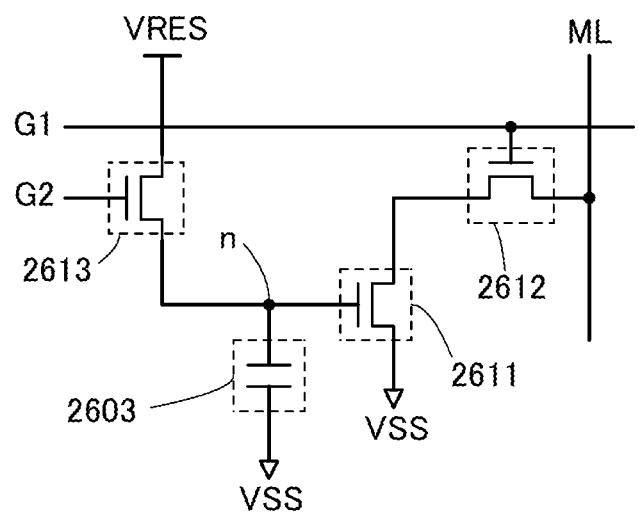
FIG. 13 is a circuit diagram of a touch sensor.

Although FIG. 12A illustrates a passive-type touch sensor in which only the capacitor 2603 is provided at the intersection of wirings as a touch sensor, an active-type touch sensor including a transistor and a capacitor may be used. FIG. 13 illustrates an example of a sensor circuit included in an active-type touch sensor.

The sensor circuit in FIG. 13 includes the capacitor 2603 and transistors 2611, 2612, and 2613.

A signal G2 is input to agate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit in FIG. 13 will be described. First, a potential for turning on the transistor 2613 is supplied as the signal G2, and a potential with respect to the voltage VRES is thus applied to a node n connected to the gate of the transistor 2611. Then, a potential for turning off the transistor 2613 is applied as the signal G2, whereby the potential of the node n is maintained. Then, mutual capacitance of the capacitor 2603 changes owing to the approach or contact of a sensing target such as a finger; accordingly, the potential of the node n is changed from VRES.

In reading operation, a potential for turning on the transistor 2612 is supplied as the signal G1. A current flowing through the transistor 2611, that is, a current flowing through the wiring ML is changed depending on the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, it is preferable to use such a transistor as the transistor 2613 because the potential of the node n can be held for a long time and the frequency of operation of resupplying VRES to the node n (refresh operation) can be reduced.

Note that the structures described in this embodiment can be combined with any of the structures described in the other embodiments as appropriate.

Embodiment 9

In this embodiment, as a display device including the light-emitting element of one embodiment of the present invention, a display device which includes a reflective liquid crystal element and a light-emitting element and is capable of performing display both in a transmissive mode and a reflective mode will be described with reference to FIGS. 14A, 14B1, and 14B2, FIG. 15, and FIG. 16. Such a display device can also be referred to as a transmissive OLED and reflective LC hybrid display (TR-hybrid display).

The display device described in this embodiment can be driven with extremely low power consumption for displaying an image using the reflective mode in a bright place such as outdoors. Meanwhile, in a dark place such as indoors or in a night environment, an image can be displayed at an optimal luminance with the use of the transmissive mode. Thus, by combination of these modes, the display device can display an image with lower power consumption and higher contrast than a conventional display panel.

As an example of the display device of this embodiment, description will be made of a display device in which a liquid crystal element provided with a reflective electrode and a light-emitting element are stacked and an opening in the reflective electrode is provided in a position overlapping with the light-emitting element. Visible light is reflected by the reflective electrode in the reflective mode and light emitted from the light-emitting element is emitted through the opening in the reflective electrode in the transmissive mode. Note that transistors used for driving these elements (the liquid crystal element and the light-emitting element) are preferably formed on the same plane. It is preferable that the liquid crystal element and the light-emitting element be stacked with an insulating layer therebetween.

Figure 14A:
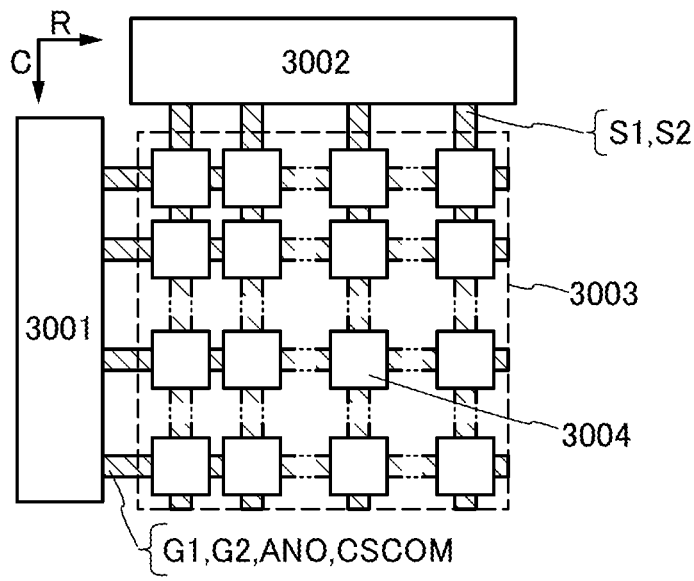
Figure 14A:
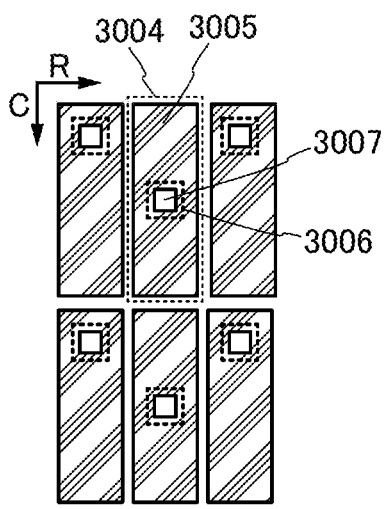
Figure 14A:
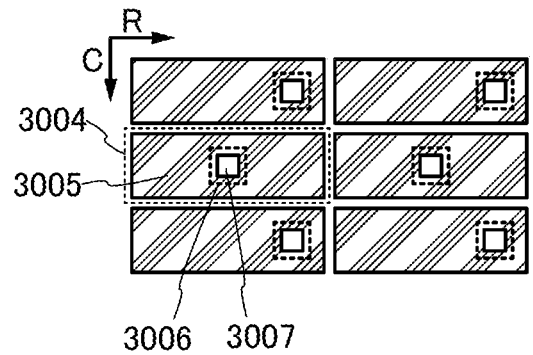

FIG. 14A is a block diagram illustrating a display device described in this embodiment. A display device 3000 includes a circuit (G) 3001, a circuit (S) 3002, and a display portion 3003. In the display portion 3003, a plurality of pixels 3004 are arranged in an R direction and a C direction in a matrix. A plurality of wirings G1, wirings G2, wirings ANO, and wirings CSCOM are electrically connected to the circuit (G) 3001. These wirings are also electrically connected to the plurality of pixels 3004 arranged in the R direction. A plurality of wirings S1 and wirings S2 are electrically connected to the circuit (S) 3002, and these wirings are also electrically connected to the plurality of pixels 3004 arranged in the C direction.

Each of the plurality of pixels 3004 includes a liquid crystal element and a light-emitting element. The liquid crystal element and the light-emitting element include portions overlapping with each other.

FIG. 14B1 shows the shape of a conductive film 3005 serving as a reflective electrode of the liquid crystal element included in the pixel 3004. Note that an opening 3007 is provided in a position 3006 which is part of the conductive film 3005 and which overlaps with the light-emitting element. That is, light emitted from the light-emitting element is emitted through the opening 3007.

The pixels 3004 in FIG. 14B1 are arranged such that the adjacent pixels 3004 in the R direction exhibit different colors. Furthermore, the openings 3007 are provided so as not to be arranged in a line in the R direction. Such arrangement has an effect of suppressing crosstalk between the light-emitting elements of adjacent pixels 3004. Furthermore, there is an advantage that element formation is facilitated.

The opening 3007 can have a polygonal shape, a quadrangular shape, an elliptical shape, a circular shape, a cross shape, a stripe shape, or a slit-like shape, for example.

FIG. 14B2 illustrates another example of the arrangement of the conductive films 3005.

The ratio of the opening 3007 to the total area of the conductive film 3005 (excluding the opening 3007) affects the display of the display device. That is, a problem is caused in that as the area of the opening 3007 is larger, the display using the liquid crystal element becomes darker; in contrast, as the area of the opening 3007 is smaller, the display using the light-emitting element becomes darker. Furthermore, in addition to the problem of the ratio of the opening, a small area of the opening 3007 itself also causes a problem in that extraction efficiency of light emitted from the light-emitting element is decreased. The ratio of the opening 3007 to the total area of the conductive film 3005 (excluding the opening 3007) is preferably 5% or more and 60% or less because the display quality can be maintained even when the liquid crystal element and the light-emitting element are used in a combination.

Figure 15:
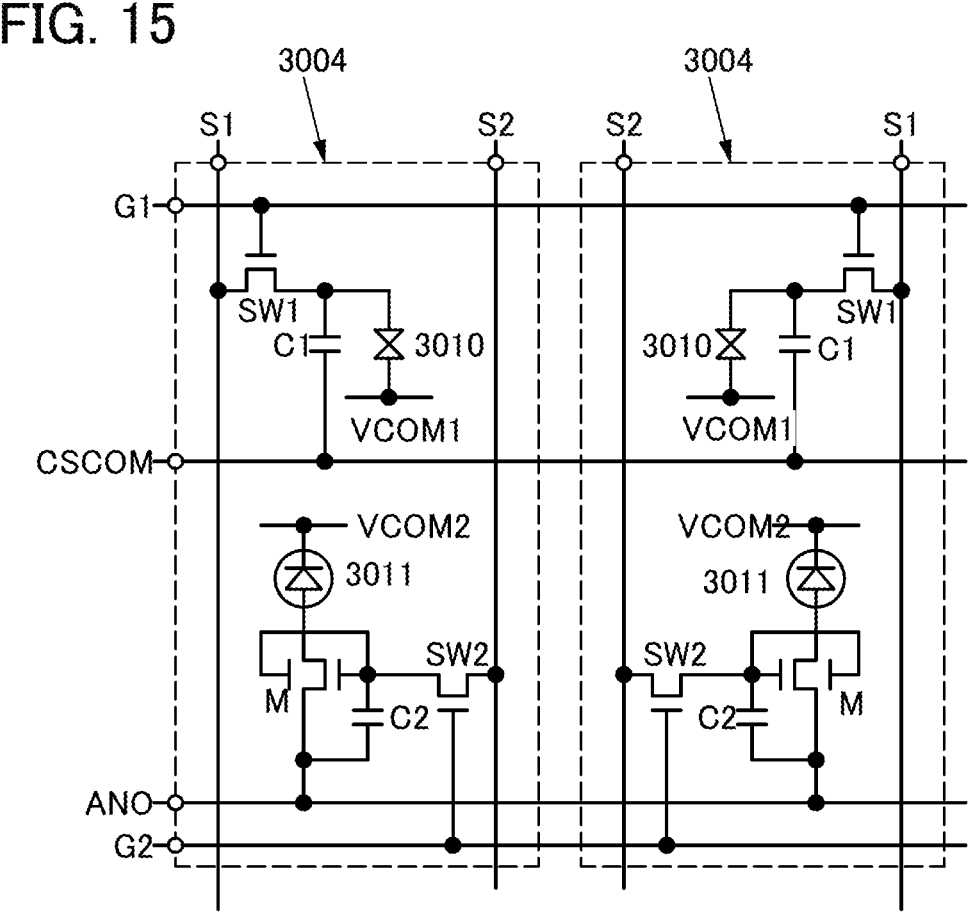
FIG. 15 illustrates a circuit configuration of a display device.

Next, an example of a circuit configuration of the pixel 3004 is described with reference to FIG. 15. FIG. 15 illustrates two adjacent pixels 3004.

The pixel 3004 includes a transistor SW1, a capacitor C1, a liquid crystal element 3010, a transistor SW2, a transistor M, a capacitor C2, a light-emitting element 3011, and the like. Note that these components are electrically connected to any of the wiring G1, the wiring G2, the wiring ANO, the wiring CSCOM, the wiring S, and the wiring S2 in the pixel 3004. The liquid crystal element 3010 and the light-emitting element 3011 are electrically connected to a wiring VCOM1 and a wiring VCOM2, respectively.

A gate of the transistor SW1is connected to the wiring G1. One of a source and a drain of the transistor SW1is connected to the wiring S1, and the other of the source and the drain is connected to one electrode of the capacitor C1 and one electrode of the liquid crystal element 3010. The other electrode of the capacitor C1 is connected to the wiring CSCOM. The other electrode of the liquid crystal element 3010 is connected to the wiring VCOM1.

A gate of the transistor SW2 is connected to the wiring G2. One of a source and a drain of the transistor SW2 is connected to the wiring S2, and the other of the source and the drain is connected to one electrode of the capacitor C2 and a gate of the transistor M. The other electrode of the capacitor C2 is connected to one of a source and a drain of the transistor M and the wiring ANO. The other of the source and the drain of the transistor M is connected to one electrode of the light-emitting element 3011. Furthermore, the other electrode of the light-emitting element 3011 is connected to the wiring VCOM2.

Note that the transistor M includes two gates between which a semiconductor is provided and which are electrically connected to each other. With such a structure, the amount of current flowing through the transistor M can be increased.

The on/off state of the transistor SW Iis controlled by a signal from the wiring G1. A predetermined potential is applied from the wiring VCOM1. Furthermore, orientation of liquid crystals of the liquid crystal element 3010 can be controlled by a signal from the wiring S1. A predetermined potential is applied from the wiring CSCOM.

The on/off state of the transistor SW2 is controlled by a signal from the wiring G2. By the difference between the potentials applied from the wiring VCOM2 and the wiring ANO, the light-emitting element 3011 can emit light. Furthermore, the conduction state of the transistor M can be controlled by a signal from the wiring S2.

Accordingly, in the structure of this embodiment, in the case of the reflective mode, the liquid crystal element 3010 is controlled by the signals supplied from the wiring G1 and the wiring S1 and optical modulation is utilized, whereby an image can be displayed. In the case of the transmissive mode, the light-emitting element 3011 can emit light when the signals are supplied from the wiring G2 and the wiring S2. In the case where both modes are performed at the same time, desired driving can be performed on the basis of the signals from the wiring G1, the wiring G2, the wiring S1, and the wiring S2.

Figure 16:
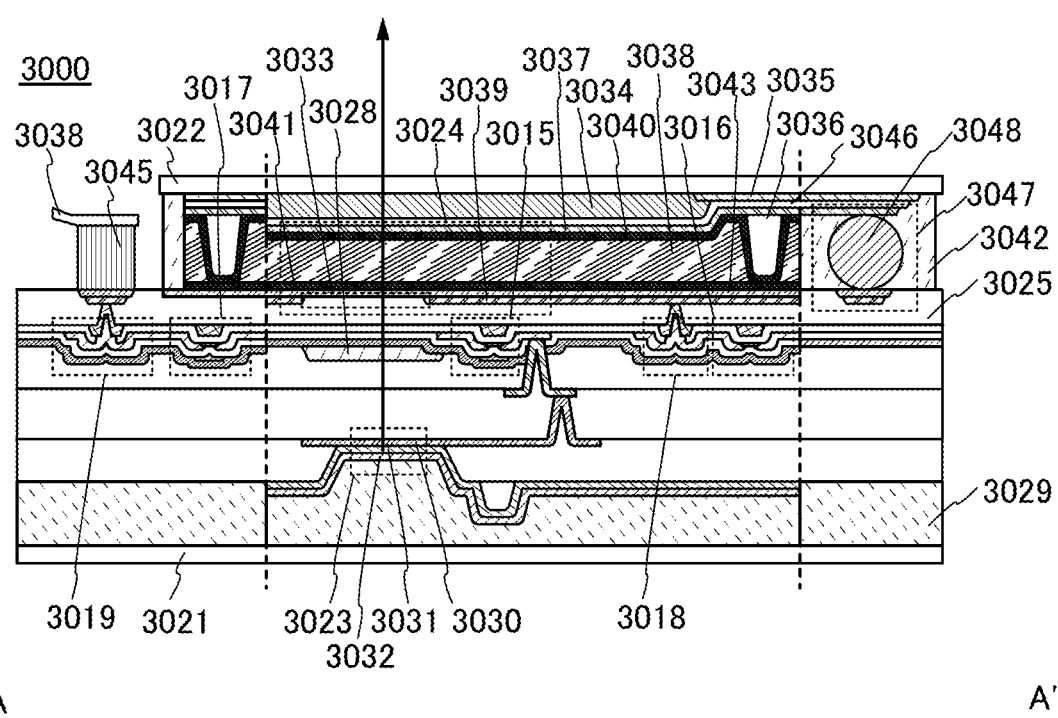
FIG. 16 illustrates a cross-sectional structure of a display device.

Next, specific description will be given with reference to FIG. 16, a schematic cross-sectional view of the display device 3000 described in this embodiment.

The display device 3000 includes a light-emitting element 3023 and a liquid crystal element 3024 between substrates 3021 and 3022. Note that the light-emitting element 3023 and the liquid crystal element 3024 are formed with an insulating layer 3025 positioned therebetween. That is, the light-emitting element 3023 is positioned between the substrate 3021 and the insulating layer 3025, and the liquid crystal element 3024 is positioned between the substrate 3022 and the insulating layer 3025.

A transistor 3015, a transistor 3016, a transistor 3017, a coloring layer 3028, and the like are provided between the insulating layer 3025 and the light-emitting element 3023.

A bonding layer 3029 is provided between the substrate 3021 and the light-emitting element 3023. The light-emitting element 3023 includes a conductive layer 3030 serving as one electrode, an EL layer 3031, and a conductive layer 3032 serving as the other electrode which are stacked in this order over the insulating layer 3025. In the light-emitting element 3023 that is a bottom emission light-emitting element, the conductive layer 3032 and the conductive layer 3030 contain a material that reflects visible light and a material that transmits visible light, respectively. Light emitted from the light-emitting element 3023 is transmitted through the coloring layer 3028 and the insulating layer 3025 and then transmitted through the liquid crystal element 3024 via an opening 3033, thereby being emitted to the outside of the substrate 3022.

In addition to the liquid crystal element 3024, a coloring layer 3034, a light-blocking layer 3035, an insulating layer 3046, a structure 3036, and the like are provided between the insulating layer 3025 and the substrate 3022. The liquid crystal element 3024 includes a conductive layer 3037 serving as one electrode, a liquid crystal 3038, a conductive layer 3039 serving as the other electrode, alignment films 3040 and 3041, and the like. Note that the liquid crystal element 3024 is a reflective liquid crystal element and the conductive layer 3039 serves as a reflective electrode; thus, the conductive layer 3039 is formed using a material with high reflectivity. Furthermore, the conductive layer 3037 serves as a transparent electrode, and thus is formed using a material that transmits visible light. The alignment films 3040 and 3041 are provided on the conductive layers 3037 and 3039 and in contact with the liquid crystal 3038. The insulating layer 3046 is provided so as to cover the coloring layer 3034 and the light-blocking layer 3035 and serves as an overcoat. Note that the alignment films 3040 and 3041 are not necessarily provided.

The opening 3033 is provided in part of the conductive layer 3039. A conductive layer 3043 is provided in contact with the conductive layer 3039. Since the conductive layer 3043 has a light-transmitting property, a material transmitting visible light is used for the conductive layer 3043.

The structure 3036 serves as a spacer that prevents the substrate 3022 from coming closer to the insulating layer 3025 than required. The structure 3036 is not necessarily provided.

One of a source and a drain of the transistor 3015 is electrically connected to the conductive layer 3030 in the light-emitting element 3023. For example, the transistor 3015 corresponds to the transistor M in FIG. 15.

One of a source and a drain of the transistor 3016 is electrically connected to the conductive layer 3039 and the conductive layer 3043 in the liquid crystal element 3024 through a terminal portion 3018. That is, the terminal portion 3018 has a function of electrically connecting the conductive layers provided on both surfaces of the insulating layer 3025. The transistor 3016 corresponds to the transistor SW1 in FIG. 15.

A terminal portion 3019 is provided in a region where the substrates 3021 and 3022 do not overlap with each other. The terminal portion 3019 electrically connects the conductive layers provided on both surfaces of the insulating layer 3025 like the terminal portion 3018. The terminal portion 3019 is electrically connected to a conductive layer obtained by processing the same conductive film as the conductive layer 3043. Thus, the terminal portion 3019 and an FPC 3044 can be electrically connected to each other through a connection layer 3045.

A connection portion 3047 is provided in part of a region where a bonding layer 3042 is provided. In the connection portion 3047, the conductive layer obtained by processing the same conductive film as the conductive layer 3043 and part of the conductive layer 3037 are electrically connected with a connector 3048. Accordingly, a signal or a potential input from the FPC 3044 can be supplied to the conductive layer 3037 through the connector 3048.

The structure 3036 is provided between the conductive layer 3037 and the conductive layer 3043. The structure 3036 has a function of maintaining a cell gap of the liquid crystal element 3024.

As the conductive layer 3043, a metal oxide, a metal nitride, or an oxide such as an oxide semiconductor whose resistance is reduced is preferably used. In the case of using an oxide semiconductor, a material in which at least one of the concentrations of hydrogen, boron, phosphorus, nitrogen, and other impurities and the number of oxygen vacancies is made to be higher than those in a semiconductor layer of a transistor is used for the conductive layer 3043.

Note that the structures described in this embodiment can be combined with any of the structures described in the other embodiments as appropriate.

Example 1

Synthesis Example 1

In this example, a method for synthesizing 2-[3-(dibenzothiophen-4-yl)phenyl]benzofuro[2,3-b]quinoxaline (abbreviation: 2mDBtPBfqn) represented by Structural Formula (100) in Embodiment 1, which is the organic compound of one embodiment of the present invention, will be described. The structure of 2mDBtPBfqn is shown below.

[Chemical Formula 29]

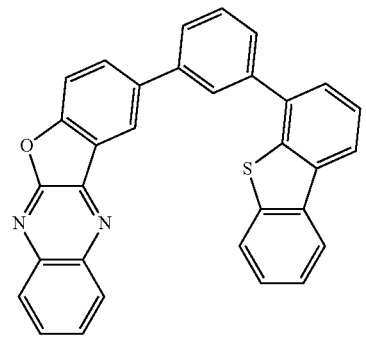

(100)

(2mDBtPBfqn)

Step 1: Synthesis of
2-(5-chloro-2-methoxy)-3-chloroquinoxaline

Into a 200-mL three-neck flask were put 1.8 g (10 mmol) of a 5-chloro-2-methoxyphenylboronic acid, 2.0 g (10 mmol) of 2,3-dichloroquinoxaline, 60 mg (0.2 mmol) of tri(o-tolyl)phosphine, 35 mL of toluene, 15 mL of ethanol, and 10 mL of a 2M aqueous solution of potassium carbonate. This mixture was degassed under reduced pressure, and the air in the system was replaced with nitrogen. Then, 22 mg (0.1 mmol) of palladium(II) acetate was added to the mixture, and the resulting mixture was refluxed at 80° C. for 4 hours.

After the reflux, the mixture was separated into an organic layer and an aqueous layer, and the aqueous layer was subjected to extraction with ethyl acetate. The obtained extracted solution and the organic layer were combined and washed with saturated saline. The obtained solution was dried with magnesium sulfate. This mixture was gravity-filtered, and the obtained filtrate was concentrated to give a black oily substance. This oily substance was purified by silica gel column chromatography (using a developing solvent in which the ratio of toluene to hexane was 3:2) to give an oily substance. The obtained oily substance was recrystallized from hexane, so that 1.6 g of a white solid of a target substance was obtained in a yield of 52%. A synthesis scheme (a-1) of Step 1 is shown below.

[Chemical Formula 30]

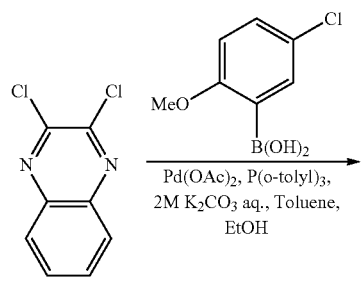
(a-1)

Step 2: Synthesis of 4-chloro-2-(3-chloroquinoxalin-2-yl)phenol

Next, into a 200-mL three-neck flask were put 1.6 g (5.2 mmol) of 2-(5-chloro-2-methoxy)-3-chloroquinoxaline and 10 mL of dichloromethane. Then, 10 mL (10 mmol) of boron tribromide (a 1M dichloromethane solution) was dripped to this solution with a dropping funnel at 0° C. under a nitrogen stream. After the dripping, the solution was stirred at room temperature for 18 hours. After the stirring, about 30 mL of water was added to the solution, and the resulting solution was stirred for 1 hour. After that, about 50 mL of a saturated aqueous solution of sodium hydrogen carbonate was added, and the resulting solution was stirred for 1 hour. Then, this mixture was separated into an organic layer and an aqueous layer, and the aqueous layer was subjected to extraction with dichloromethane. The obtained extracted solution and the organic layer were combined and washed with a saturated sodium thiosulfate aqueous solution. The obtained solution was dried with magnesium sulfate, and then the mixture was gravity-filtered. The obtained filtrate was concentrated to give a solid. The obtained solid was washed with hexane, so that 1.4 g of a yellow solid of a target substance was obtained in a yield of 93%. A synthesis scheme (a-2) of Step 2 is shown below.

[Chemical Formula 31]

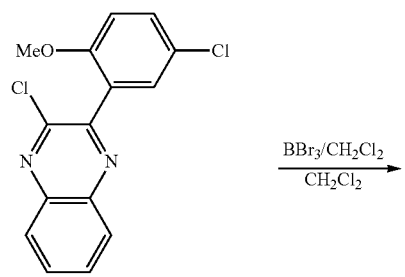
(a-2)

Step 3: Synthesis of 2-chlorobenzofuro[2,3-b]quinoxaline

Then, into a 200-mL three-neck flask were put 1.4 g (5.2 mmol) of 4-chloro-2-(3-chloroquinoxalin-2-yl)phenol, 25 mL of N-methyl-2-pyrrolidone (NMP), and 1.4 g (10 mmol) of potassium carbonate. This flask was subjected to stirring at 160° C. for 3 hours. After the stirring, this mixture was cooled down to room temperature and added to about 100 mL of water. The obtained mixture was separated into an organic layer and an aqueous layer, and the aqueous layer was subjected to extraction with toluene. The obtained extracted solution and the organic layer were combined and washed with a dilute hydrochloric acid and saturated saline. The obtained solution was dried with magnesium sulfate, and then the mixture was gravity-filtered. The obtained filtrate was concentrated to give a solid. The obtained solid was washed with hexane, so that 0.8 g of a pale brown solid of a target substance was obtained in a yield of 64%. A synthesis scheme (a-3) of Step 3 is shown below.

[Chemical Formula 32]

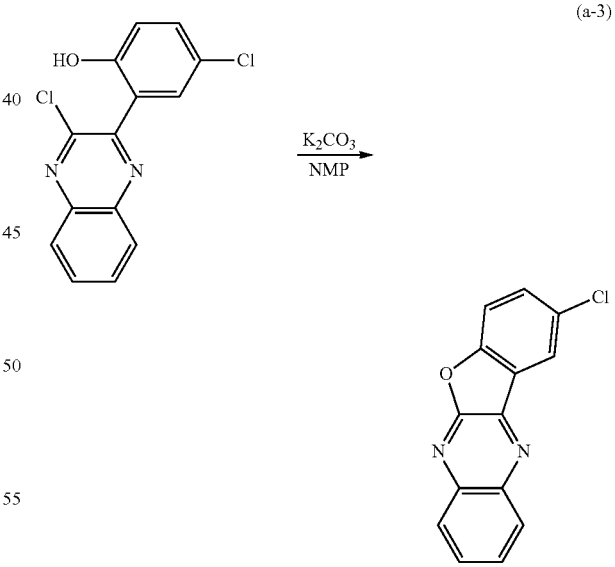
(a-3)

Step 4: Synthesis of 2mDBtPBfqn

Into a 200-mL three-neck flask were put 0.8 g (3.0 mmol) of 2-chlorobenzofuro[2,3-b]quinoxaline, 0.9 g (3.0 mmol) of a 3-(dibenzothiophen-4-yl)phenylboronic acid, 1.3 g (6.0 mmol) of tripotassium phosphate, and 21 mg (0.060 mmol) of di(1-adamantyl)-n-butylphosphine, and the air in the flask was replaced with nitrogen.

To this mixture, 15 mL of diethylene glycol dimethyl ether and 0.7 g (9.0 mmol) of tert-butyl alcohol were added. While the pressure was reduced, the mixture was stirred to be degassed. Then, 6.7 mg (0.030 mmol) of palladium(II) acetate was added to the mixture, and the resulting mixture was stirred at 180° C. in a nitrogen stream for 24 hours. After the stirring, water was added to the mixture to separate the obtained mixture into an organic layer and an aqueous layer, and the aqueous layer was subjected to extraction with toluene. The obtained extracted solution and the organic layer were combined and washed with saturated saline. After the washing, the solution was dried with magnesium sulfate, and then the mixture was gravity-filtered. The obtained filtrate was concentrated to give a solid. The obtained solid was purified by silica gel column chromatography (using a developing solvent in which the ratio of hexane to toluene was 5:1) to give a solid. The obtained solid was recrystallized from toluene/hexane, so that 0.4 g of a pale yellow powder of a target substance was obtained in a yield of 24%. A synthesis scheme (a-4) of Step 4 is shown below.

[Chemical Formula 33]

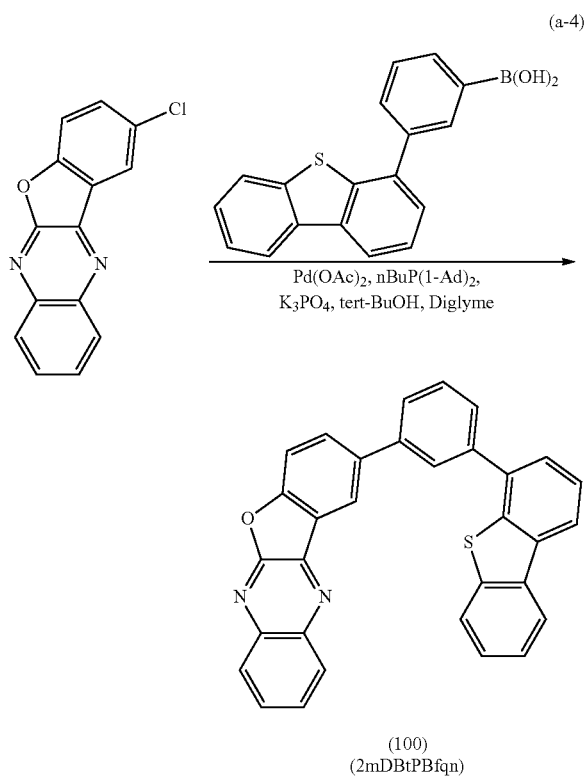

(100)
(2mDBtPBfqn)

By repeating the above procedure, 1.3 g of a target substance 2mDBtPBfqn was synthesized.

By a train sublimation method, 1.3 g of the obtained pale yellow powder of 2mDBtPBfqn was purified. In the purification by sublimation, the pale yellow powder was heated at 260° C. under a pressure of 10 Pa with a flow rate of an argon gas of 5.0 mL/min. After the purification by sublimation, 1.1 g of a pale yellow solid of 2mDBtPBfqn was obtained at a collection rate of 89%.

Figure 17:
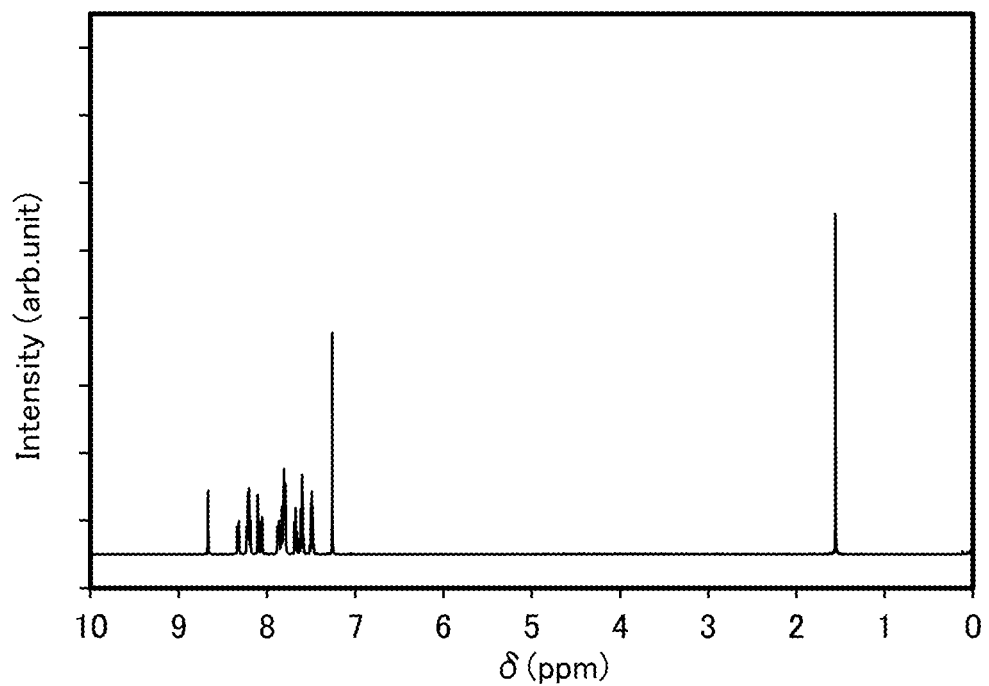
FIG. 17 is the $^1$H-NMR chart of an organic compound represented by Structural Formula (100).

Analysis results by nuclear magnetic resonance (H-NMR) spectroscopy of the pale yellow solid obtained in Step 4 are shown below. FIG. 17 shows the $^1$H-NMR chart. The results revealed that 2mDBtPBfqn, the organic compound of one embodiment of the present invention represented by Structural Formula (100), was obtained in this example.

$^1$H NMR (CDCl$_3$, 500 MHz): δ=7.47-7.52 (m, 2H), 7.59-7.63 (m, 2H), 7.68 (t, J=7.5 Hz, 1H), 7.79-7.88 (m, 6H), 8.06 (dd, J$_1$=9.0 Hz, J$_2$=1.5 Hz, 1H), 8.10 (s, 1H), 8.19-8.23 (m, 3H), 8.33 (dd, J$_1$=7.0 Hz, J$_2$=2.0 Hz, 1H), 8.67 (d, J=1.5 Hz, 1H).

Figure 18:
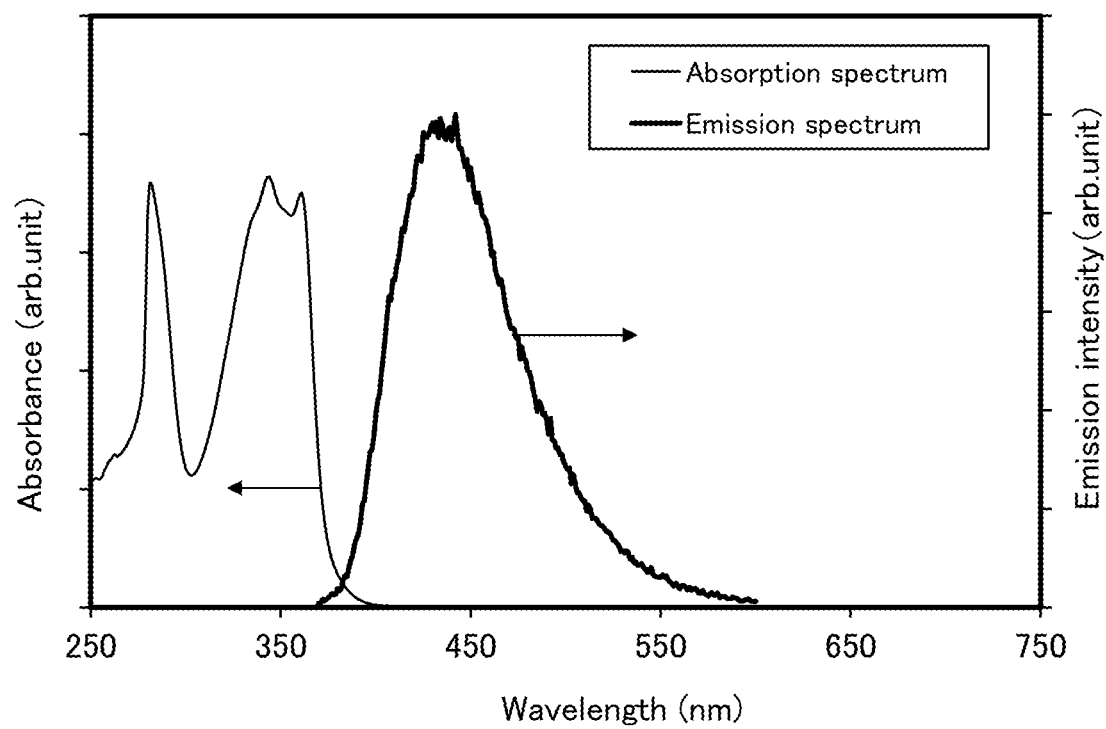
FIG. 18 shows the ultraviolet-visible absorption spectrum and the emission spectrum of the organic compound represented by Structural Formula (100) in a solution.
Figure 19:
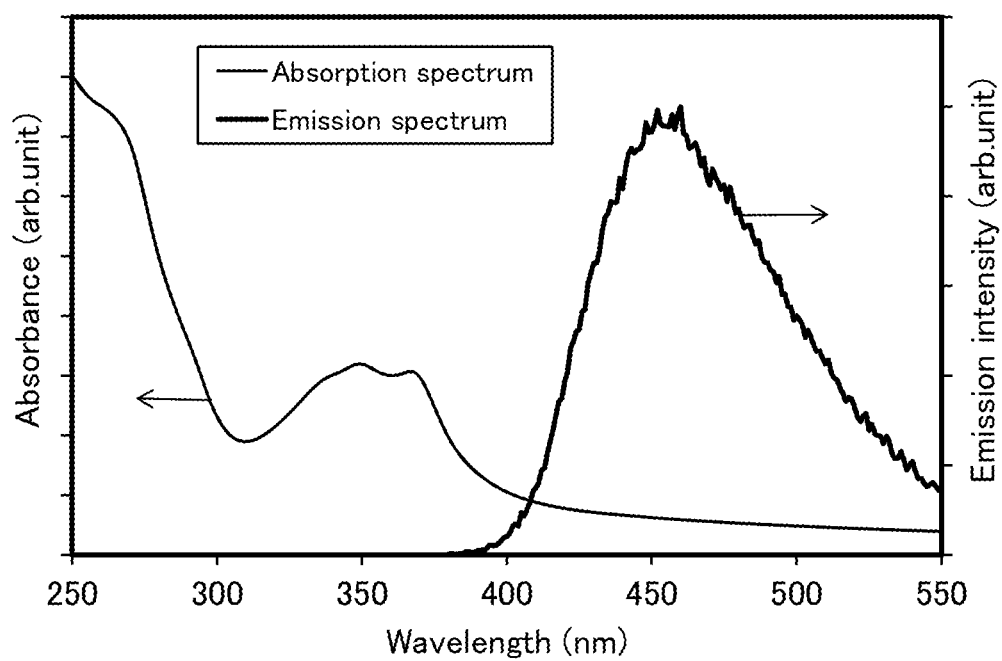
FIG. 19 shows the ultraviolet-visible absorption spectrum and the emission spectrum of the organic compound represented by Structural Formula (100) in a solid thin film.

Then, the ultraviolet-visible absorption spectra (hereinafter, simply referred to as "absorption spectra") and emission spectra of 2mDBtPBfqn in a toluene solution and that in a solid thin film were measured. The solid thin film was formed over a quartz substrate by a vacuum evaporation method. The absorption spectra were measured with an ultraviolet-visible light spectrophotometer (V550 type, produced by JASCO Corporation). The emission spectra were measured with a fluorescence spectrophotometer (FS920, produced by Hamamatsu Photonics K.K.). FIG. 18 shows the measurement results of the absorption and emission spectra of 2mDBtPBfqn in the toluene solution. The horizontal axis represents the wavelength and the vertical axes represent the absorbance and emission intensity. FIG. 19 shows the measurement results of the absorption and emission spectra of 2mDBtPBfqn in the solid thin film. The horizontal axis represents the wavelength and the vertical axes represent the absorbance and emission intensity.

FIG. 18 shows that 2mDBtPBfqn in the toluene solution has absorption peaks at around 281 nm, 344 nm, and 361 nm, and an emission wavelength peak at around 434 nm. FIG. 19 shows that 2mDBtPBfqn in the solid thin film has absorption peaks at around 244 nm, 265 nm, 336 nm, 349 nm, and 368 nm, and an emission wavelength peak at around 459 nm (an excitation wavelength of 365 nm).

Next, 2mDBtPBfqn was subjected to cyclic voltammetry (CV) measurement. An electrochemical analyzer (ALS model 600A or 600C, produced by BAS Inc.) was used for the CV measurement.

As for a solution used for the CV measurement, dehydrated dimethylformamide (DMF, produced by Sigma-Aldrich Inc., 99.8%, Catalog No. 227056-12) was used as a solvent, and tetra-n-butylammonium perchlorate (electrochemical grade, Wako Pure Chemical Industries, Ltd., manufacturer's code: 043999, CAS. No. 1923-70-2), which was a supporting electrolyte, was dissolved in the solvent so that the concentration of tetra-n-butylammonium perchlorate can be 100 mmol/L. Furthermore, the measurement target was dissolved in the solution so that the concentration thereof can be 2 mmol/L. Then, the solution was put into an electrochemical cell, electrodes were set, and then degasification by argon bubbling was performed for approximately 30 minutes.

The electrodes used for the measurement were a platinum electrode (produced by BAS Inc., PTE platinum electrode) as a working electrode, a platinum electrode (produced by BAS Inc., Pt counter electrode) as an auxiliary electrode, and a reference electrode for nonaqueous solvent (produced by BAS Inc., RE-7 reference electrode for nonaqueous solvent (Ag/Ag$^+$)) as a reference electrode. In the CV measurement, room temperature (20° C. to 25° C.) and a scan rate of 0.1 V/sec were employed. The potential energy of the reference electrode with respect to the vacuum level was assumed to be −4.94 eV in this example.

Figure 31A:
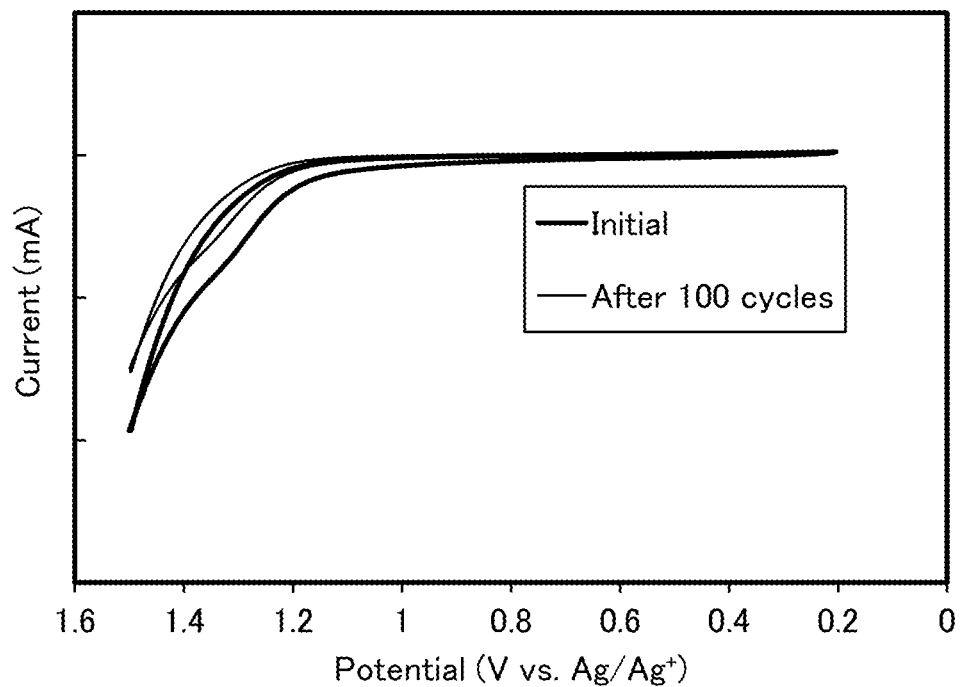
FIGS. 31A and 31B show the oxidation reaction characteristics and the reduction reaction characteristics of the organic compound represented by Structural Formula (100).

In the measurements of the oxidation reaction characteristics, scanning in which the potential of the working electrode with respect to the reference electrode was changed from 1.20 V to 1.50 V and then changed from 1.50 V to 1.20 V was regarded as one cycle, and 100 cycles were measured. FIG. 31A shows the measurement results after the first cycle as "Initial" and the measurement results after the hundredth cycle as "After 100 cycles."

The measurement results of the oxidation reaction characteristics revealed that 2mDBtPBfqn showed excellent properties against repeated redox reactions between an oxidized state and a neutral state without large variations in oxidation peak even after 100 cycles.

Figure 31B:
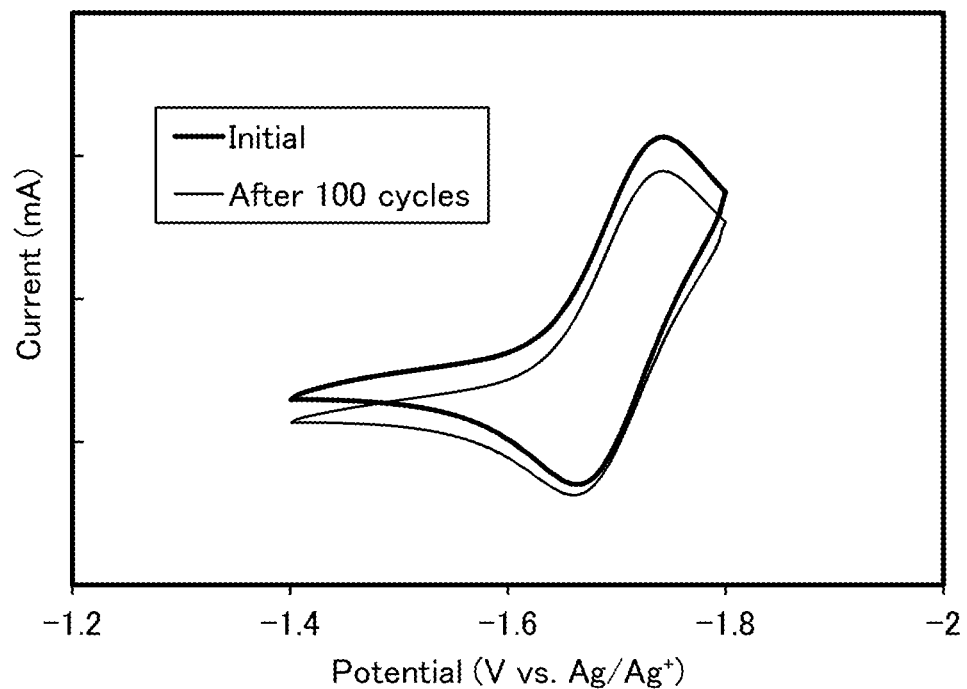

In the measurements of the reduction reaction characteristics, scanning in which the potential of the working electrode with respect to the reference electrode was changed from −1.40 V to −1.80 V and then changed from −1.80 V to −1.40 V was regarded as one cycle, and 100 cycles were measured. FIG. 31B shows the measurement results after the first cycle as "Initial" and the measurement results after the hundredth cycle as "After 100 cycles."

The measurement results of the reduction reaction characteristics revealed that 2mDBtPBfqn showed high resistance to repeated redox reactions between a reduced state and a neutral state without large variations in reduction peak even after 100 cycles.

The HOMO and LUMO levels of 2mDBtPBfqn were calculated also from the CV measurement results.

According to the measurement results of the oxidation reaction characteristics of 2mDBtPBfqn, an oxidation peak potential $E_{pa}$ was 1.31 V and a reduction peak potential $E_{pc}$ was 1.19 V. Therefore, a half-wave potential (an intermediate potential between $E_{pa}$ and $E_{pc}$) was determined to be 1.25 V. This means that 2mDBtPBfqn is oxidized with an electric energy of 1.25 [V vs. Ag/Ag$^+$], and this energy corresponds to the HOMO level. Note that since the potential energy of the reference electrode, which was used in this example, with respect to the vacuum level was calculated to be −4.94 [eV], the HOMO level of 2mDBtPBfqn was found to be as follows: −4.94−1.25=−6.19 [eV].

According to the measurement results of the reduction reaction characteristics of 2mDBtPBfqn, the reduction peak potential $E_{pc}$ was −1.74 V and the oxidation peak potential $E_{p}a$ was −1.66 V. Therefore, a half-wave potential (an intermediate potential between $E_{pa}$ and $E_{pc}$) was determined to be −1.70 V. This means that 2mDBtPBfqn is reduced with an electric energy of −1.70 [V vs. Ag/Ag$^+$], and this energy corresponds to the LUMO level. Thus, similarly to the above, the potential energy of the reference electrode with respect to the vacuum level was calculated to be −4.94 [eV]; accordingly, the LUMO level of 2mDBtPBfqn was found to be as follows: −4.94−(−1.70)=−3.24 [eV].

Example 2

Figure 20:
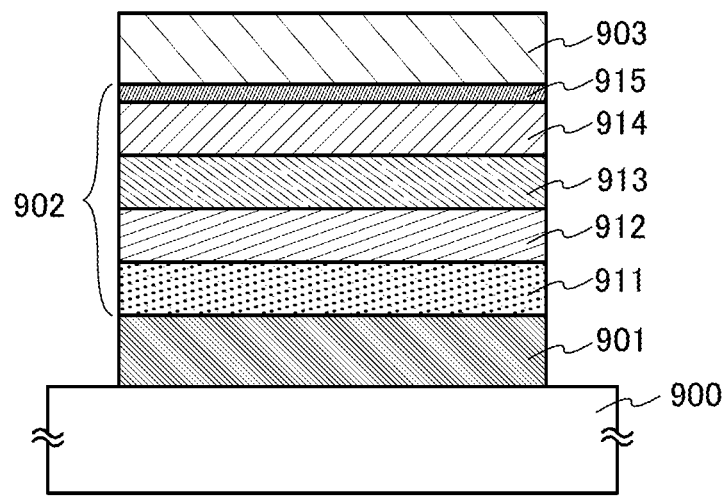
FIG. 20 illustrates a light-emitting element.
Figure 21:
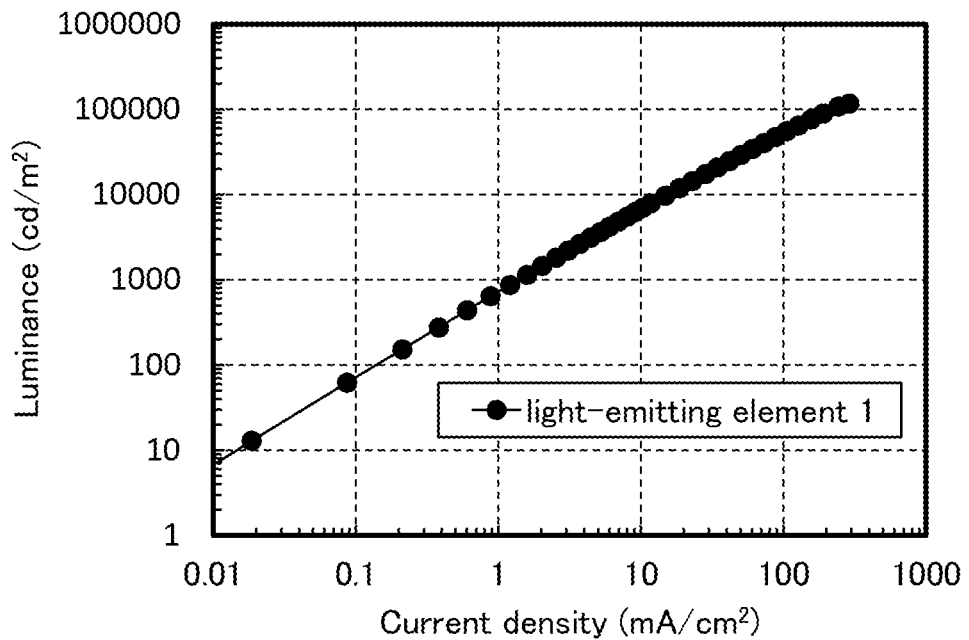
FIG. 21 shows the current density-luminance characteristics of a light-emitting element 1.
Figure 22:
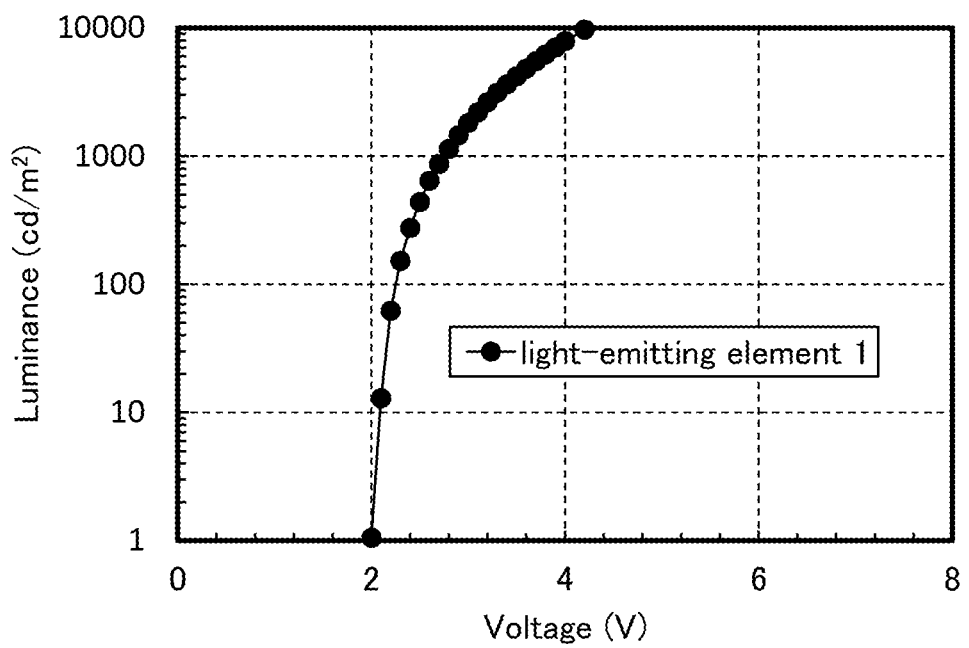
FIG. 22 shows the voltage-luminance characteristics of the light-emitting element 1.
Figure 23:
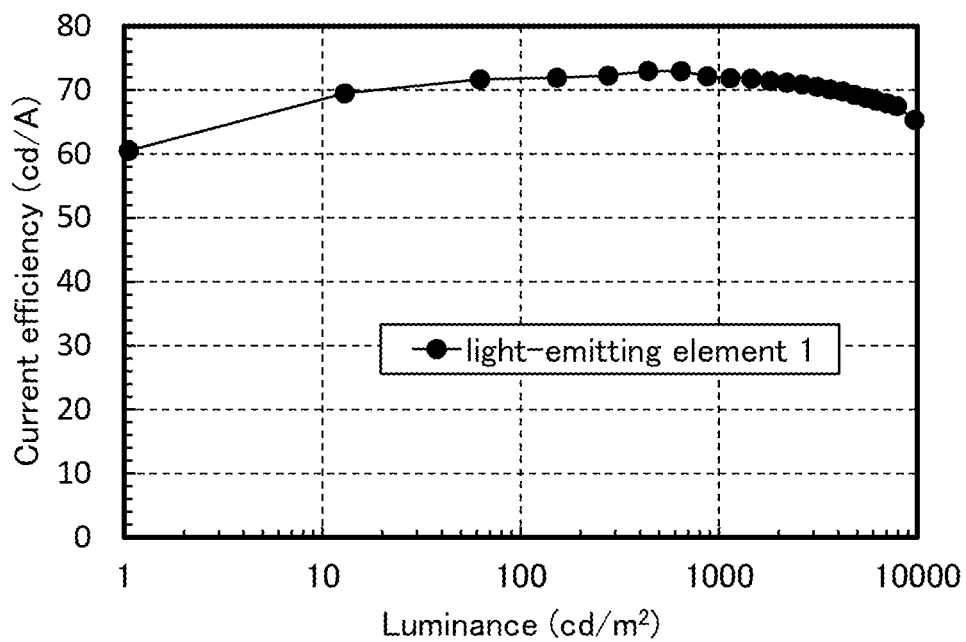
FIG. 23 shows the luminance-current efficiency characteristics of the light-emitting element 1.
Figure 24:
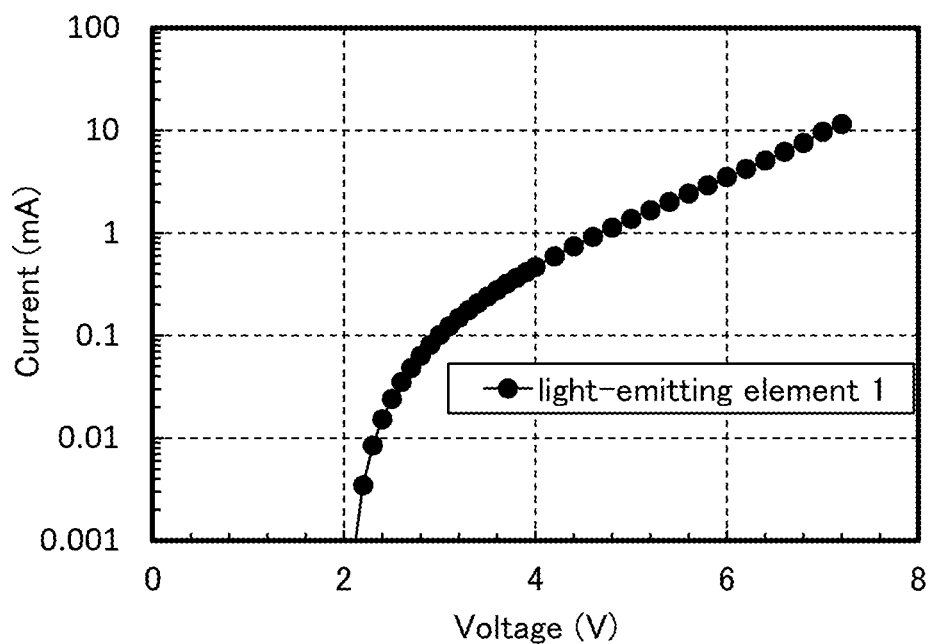
FIG. 24 shows the voltage-current characteristics of the light-emitting element 1.

In this example, an element structure and a fabrication method of a light-emitting element in which a light-emitting layer contained the organic compound 2mDBtPBfqn of one embodiment of the present invention (Structural Formula (100)) will be described. Note that FIG. 20 illustrates the element structure of the light-emitting element described in this example, and Table 3 shows specific structures. Chemical formulae of materials used in this example are shown below.

[Chemical Formulae 34]

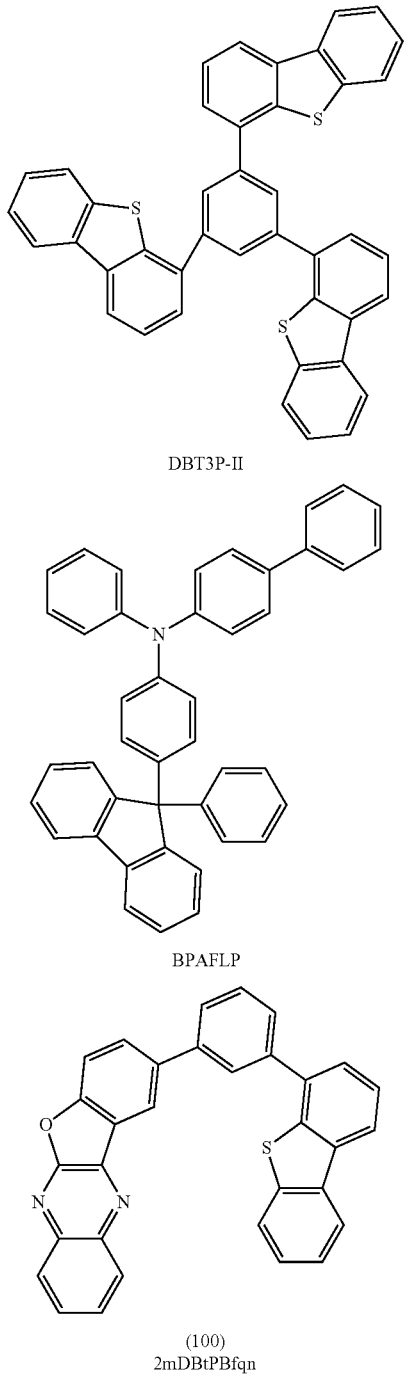

DBT3P-II

BPAFLP (100)
2mDBtPBfqn

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 1 | ITO (110 nm) | DBT3P-II:MoOx (4:2, 20 nm) | BPAFLP (20 nm) | * | 2mDBtPBfqn (20 nm) | Bphen (10 nm) | LiF (1 nm) | Al (200 nm) |

* 2mDBtPBfqn:PCBBiF:[Ir(dppm)$_2$(acac)] (0.7:0.3:0.05 (20 nm)\0.8:0.2:0.05 (20 nm))

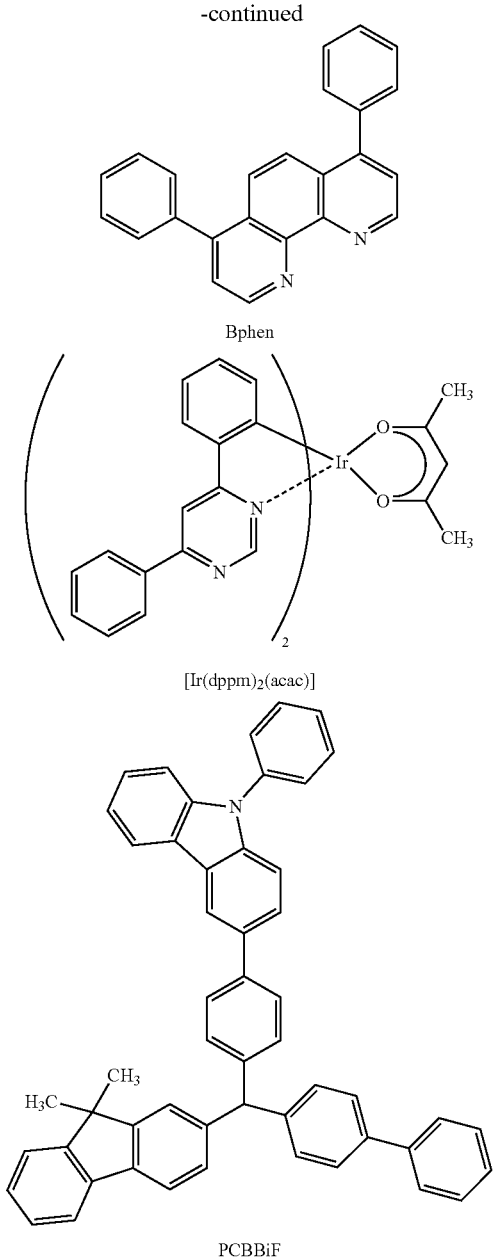

<<Fabrication of Light-Emitting Element 1>>

In the light-emitting element described in this example, as illustrated in FIG. 20, a first electrode 901 was formed over a substrate 900, an EL layer 902 was formed over the first electrode 901, and a second electrode 903 was formed over the EL layer 902.

First, the first electrode 901 was formed over the substrate 900. The electrode area was set to 4 mm² (2 mm×2 mm). A glass substrate was used as the substrate 900. An indium tin oxide (ITO) containing silicon oxide was deposited over the substrate 900 by a sputtering method, whereby the first electrode 901 functioning as an anode was formed. Note that the thickness was set to 110 nm.

Next, as pretreatment for forming a light-emitting element 1 over the substrate 900, UV ozone treatment was performed for 370 seconds after washing of a surface of the substrate with water and after baking at 200° C. for 1 hour. After that, the substrate was transferred into a vacuum evaporation apparatus where the pressure had been reduced to approximately 1×10⁻⁴ Pa, and was subjected to vacuum baking at 170° C. for 30 minutes in a heating chamber of the vacuum evaporation apparatus. Then, the substrate 900 was cooled down for approximately 30 minutes.

Then, a hole-injection layer 911, a hole-transport layer 912, a light-emitting layer 913, an electron-transport layer 914, and an electron-injection layer 915 were sequentially formed over the first electrode 901 by a vacuum evaporation method to form the EL layer 902.

After the pressure in the vacuum evaporation apparatus was reduced to 1×10⁻⁴ Pa, the hole-injection layer 911 was formed over the first electrode 901 by co-evaporation to have a mass ratio of 1,3,5-tri(dibenzothiophen-4-yl)benzene (abbreviation: DBT3P-II) to molybdenum oxide of 4:2. The thickness was 20 nm. Note that co-evaporation is an evaporation method in which a plurality of different substances are concurrently vaporized from different evaporation sources.

Then, the hole-transport layer 912 was formed over the hole-injection layer 911. To form the hole-transport layer 912, 4-phenyl-4'-(9-phenylfluoren-9-yl)triphenylamine (abbreviation: BPAFLP) was deposited to a thickness of 20 nm.

Next, the light-emitting layer 913 was formed over the hole-transport layer 912 in the following manner: the organic compound 2mDBtPBfqn of one embodiment of the present invention as a host material, N-(1,1'-biphenyl-4-yl)-9,9-dimethyl-N-[4-(9-phenyl-9H-carbazol-3-yl)phenyl]-9H-fluoren-2-amine (abbreviation: PCBBiF) as an assist material, and (acetylacetonato)bis(4,6-diphenylpyrimidinato)iridium(III)(abbreviation: [Ir(dppm)₂(acac)]) as a guest material were deposited by co-evaporation to have a mass ratio of 2mDBtPBfqn to PCBBiF and [Ir(dppm)₂(acac)] of 0.7:0.3:0.05 and a thickness of 20 nm and then were deposited by co-evaporation to have a mass ratio of 2mDBtPBfqn to PCBBiF and [Ir(dppm)₂(acac)] of 0.8:0.2:0.05 and a thickness of 20 nm. Accordingly, the light-emitting layer 913 had a stacked-layer structure with a thickness of 40 nm.

Next, the electron-transport layer 914 was formed over the light-emitting layer 913. The electron-transport layer 914 was formed in the following manner: 2mDBtPBfqn and bathophenanthroline (abbreviation: Bphen) were sequentially deposited by evaporation to thicknesses of 20 nm and 10 nm, respectively.

Then, the electron-injection layer 915 was formed over the electron-transport layer 914. The electron-injection layer 915 was formed to a thickness of 1 nm by evaporation of lithium fluoride (LiF).

After that, the second electrode 903 was formed over the electron-injection layer 915. To form the second electrode 903 serving as a cathode, aluminum was deposited by evaporation to a thickness of 200 nm. In all the evaporation steps in the fabrication method, evaporation was performed by a resistance-heating method.

The light-emitting element fabricated in this example was sealed between the substrate 900 and a substrate 905. The sealing between the substrate 900 and the substrate 905 was performed in such a manner that the substrate 905 was fixed to the substrate 900 with a sealing material in a glove box containing a nitrogen atmosphere, a sealant was applied so as to surround the light-emitting element formed over the substrate 900, and then irradiation with 365-nm ultraviolet light at 6 J/cm² was performed and heat treatment was performed at 80° C. for 1 hour.

<<Operation Characteristics of Light-Emitting Element 1>>

Operation characteristics of the light-emitting element 1 were measured. Note that the measurement was carried out at room temperature (in an atmosphere where a temperature was maintained at 25° C.). FIG. 21 to FIG. 24 show the results.

Table 2 shows initial values of main characteristics of the light-emitting element 1 at around 1000 cd/m².

TABLE 2

|  | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
| --- | --- | --- | --- | --- | --- | --- | --- | --- |
| Light-emitting element 1 | 2.7 | 0.048 | 1.2 | (0.56, 0.44) | 870 | 72 | 84 | 26 |

The above results show that the light-emitting element 1 fabricated in this example has high current efficiency and high external quantum efficiency.

Figure 25:
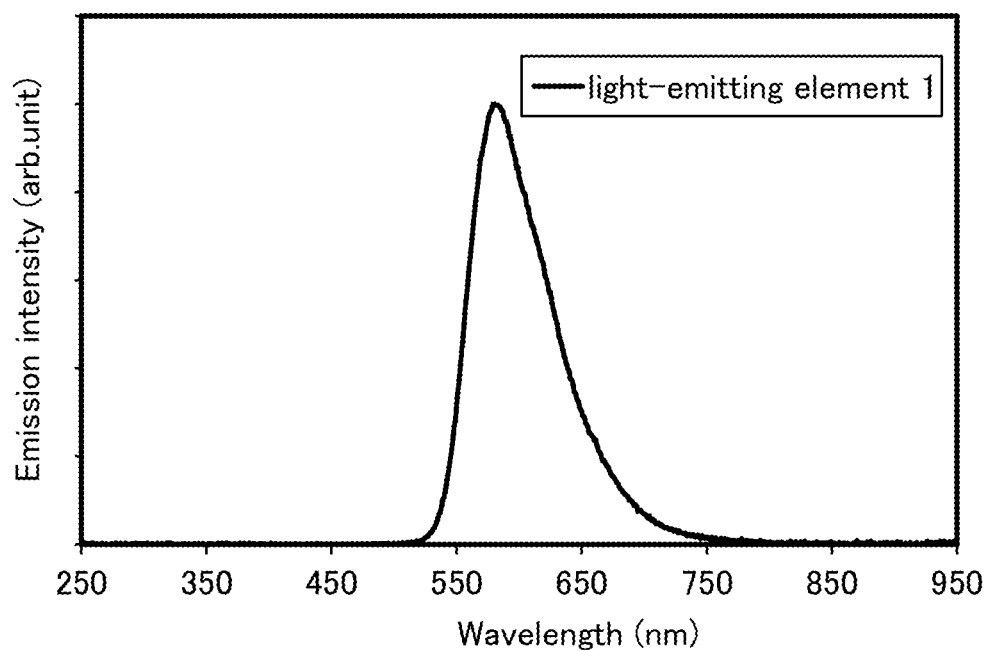
FIG. 25 shows the emission spectrum of the light-emitting element 1.
Figure 26:
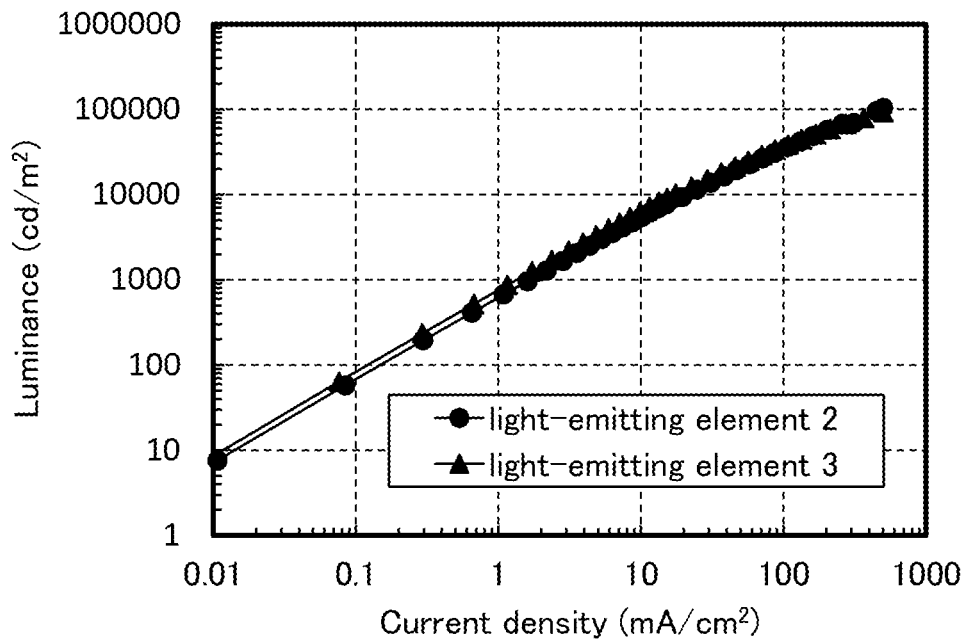
FIG. 26 shows the current density-luminance characteristics of a light-emitting element 2 and a light-emitting element 3.
Figure 27:
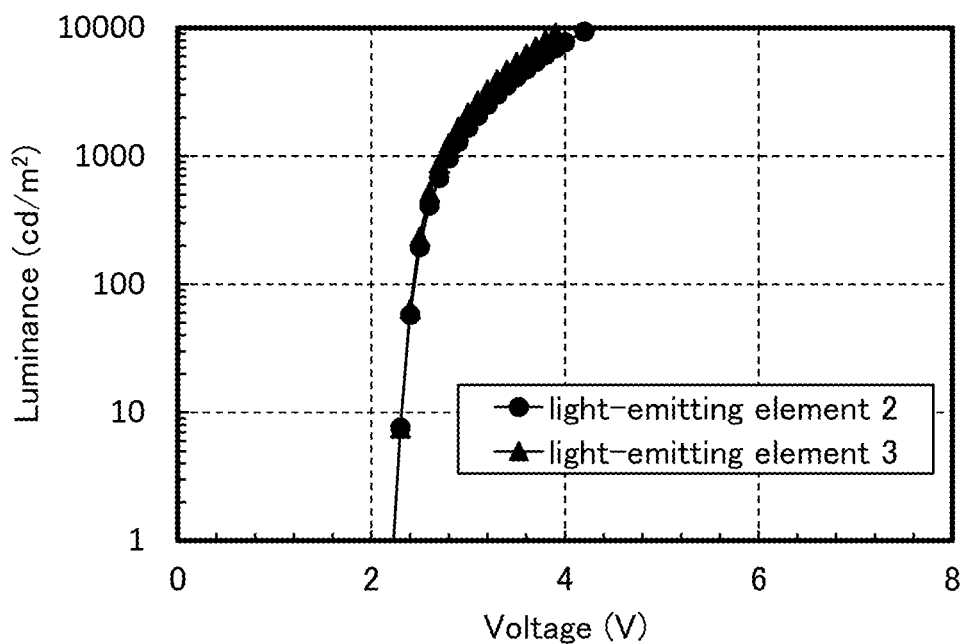
FIG. 27 shows the voltage-luminance characteristics of the light-emitting element 2 and the light-emitting element 3.
Figure 28:
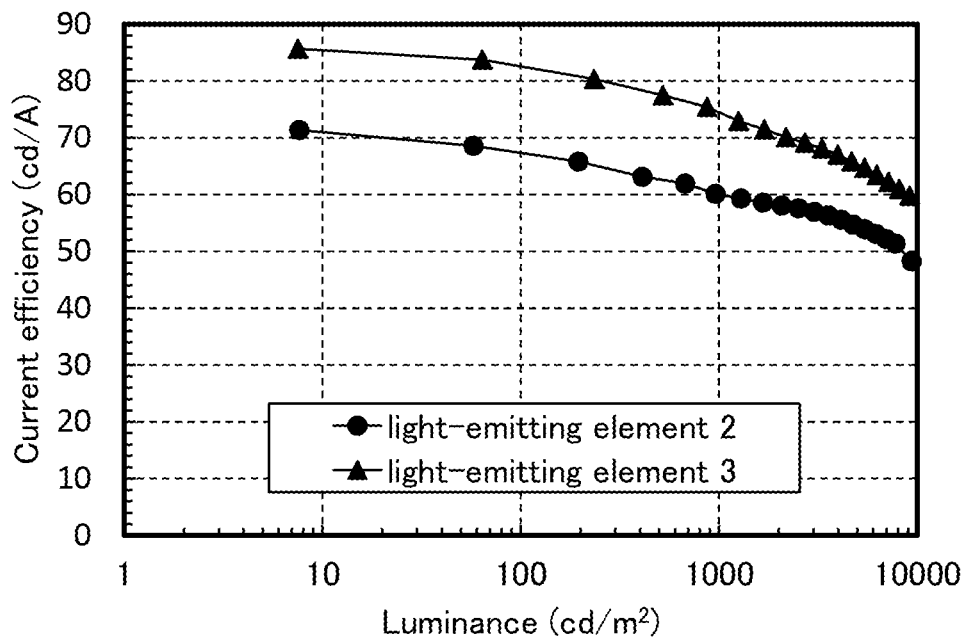
FIG. 28 shows the luminance-current efficiency characteristics of the light-emitting element 2 and the light-emitting element 3.
Figure 29:
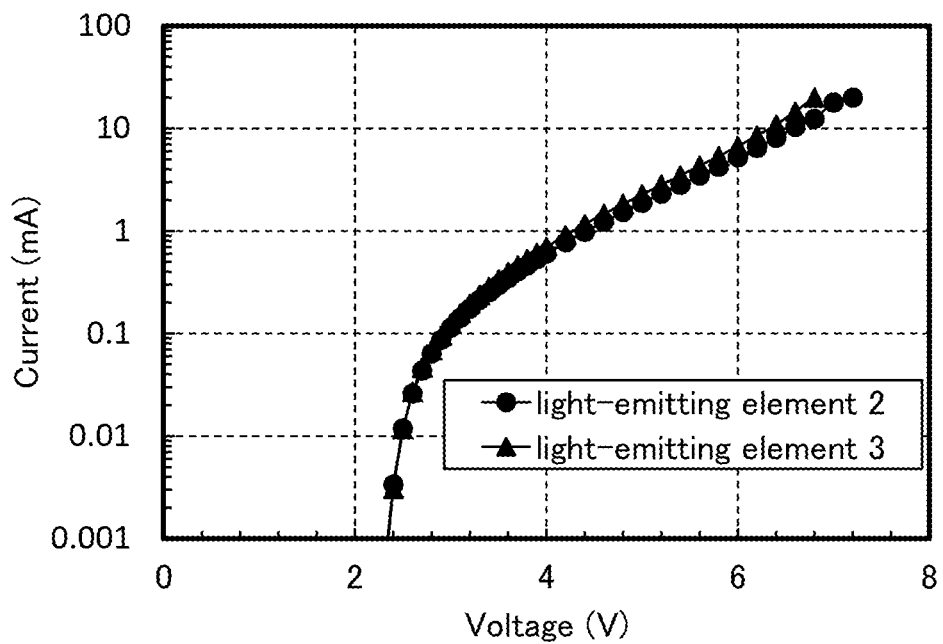
FIG. 29 shows the voltage-current characteristics of the light-emitting element 2 and the light-emitting element 3.

FIG. 25 shows an emission spectrum of the light-emitting element 1 to which current was applied at a current density of 2.5 mA/cm². As shown in FIG. 25, the emission spectrum of the light-emitting element 1 has a peak at around 580 nm, which indicates that the emission spectrum derives from light emission of the organometallic complex [Ir(dppm)$_2$(acac)] contained in the light-emitting layer 913.

Figure 32:
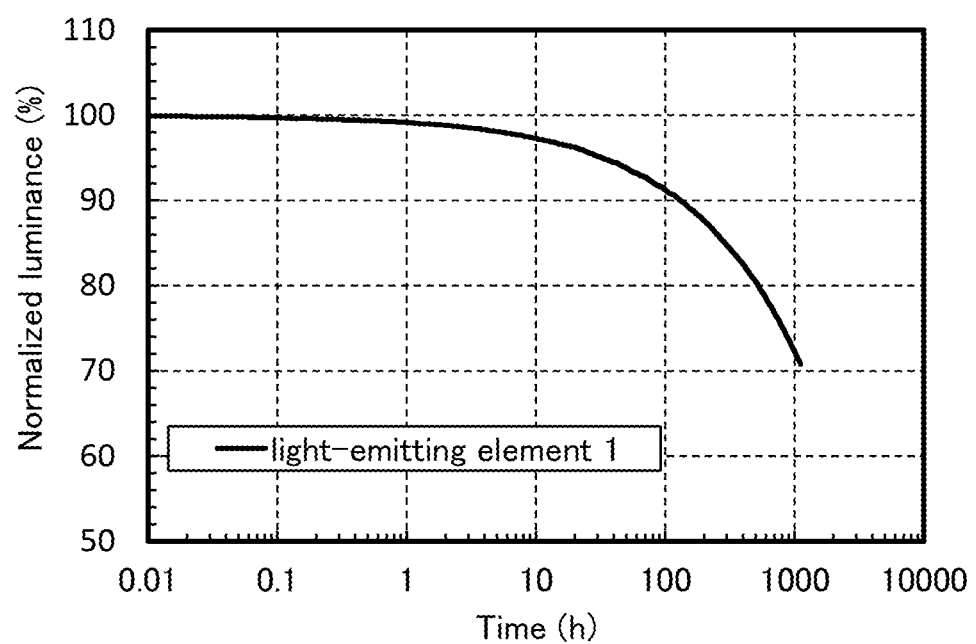
FIG. 32 shows the reliability of the light-emitting element 1.

Next, a reliability test was performed on the light-emitting element 1. FIG. 32 shows results of the reliability test. In FIG. 32, the vertical axis represents normalized luminance (%) with an initial luminance of 100%, and the horizontal axis represents driving time (h) of the elements. Note that in the reliability test, the light-emitting element 1 was driven under the conditions where the initial luminance was set to 5000 cd/m² and the current density was constant.

In the light-emitting element 1, the light-emitting layer and the electron-transport layer contained the organic compound 2mDBtPBfqn of one embodiment of the present invention. Note that 2mDBtPBfqn has a benzofuroquinoxaline skeleton and thus has a high electron-transport property. Furthermore, 2mDBtPBfqn has a stable molecular structure because dibenzothiophene, which is a condensed heteroaromatic ring, is bonded thereto via a phenyl group; thus, favorable reliability can be obtained.

Example 3

In this example, element structures and fabrication methods of light-emitting elements in each of which a light-emitting layer contained the organic compound 2mDBtPBfqn of one embodiment of the present invention (Structural Formula (100)) will be described. Note that the stacked-layer structures of the light-emitting elements described in this example were similar to that described in Example 2; thus, FIG. 20 can be referred to for the stacked-layer structures. Table 3 shows the specific structures of a light-emitting element 2 and a light-emitting element 3 described in this example. Chemical formulae of materials used in this example are shown below.

[Chemical Formulae 35]

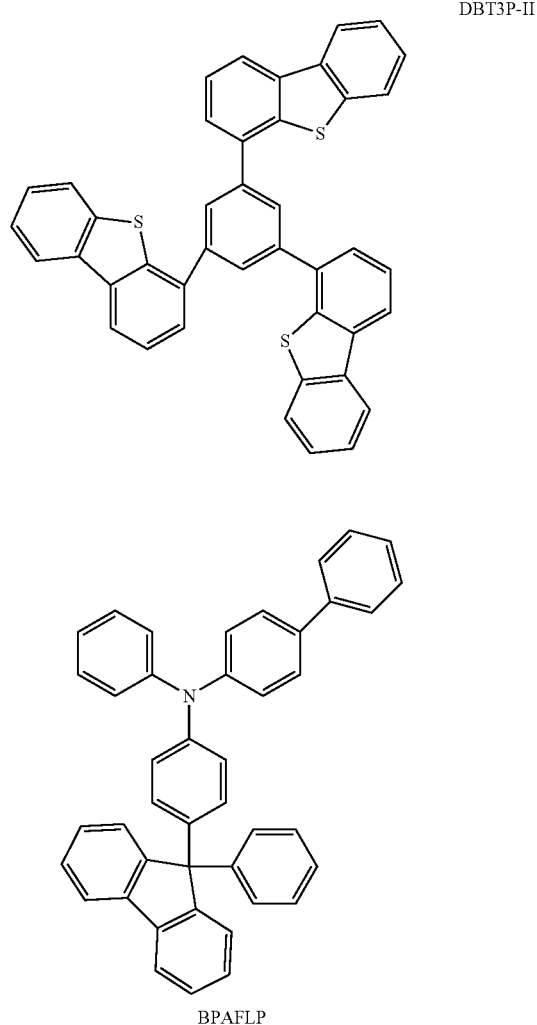

TABLE 3

|  | First electrode | Hole-injection layer | Hole-transport layer | Light-emitting layer | Electron-transport layer | | Electron-injection layer | Second electrode |
| --- | --- | --- | --- | --- | --- | --- | --- | --- |
| Light-emitting element 2 | ITO (110 nm) | DBT3P-II:MoOx (4:2, 20 nm) | BPAFLP (20 nm) | * | 2mDBtPBfqn (15 nm) | Bphen (10 nm) | LiF (1 nm) | Al (200 nm) |
| Light-emitting element 3 | ITO (110 nm) | DBT3P-II:MoOx (4:2, 20 nm) | BPAFLP (20 nm) | ** | 2mDBtPBfqn (15 nm) | Bphen (10 nm) | LiF (1 nm) | Al (200 nm) |

* 2mDBtPBfqn:[Ir(dppm)$_2$(acac)] (1:0.05, 30 nm)
** 2mDBtPBfqn:[Ir(tBuppm)$_2$(acac)] (1:0.05, 30 nm)

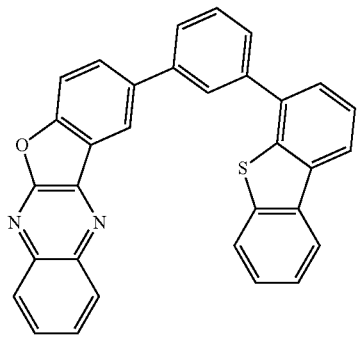

2mDBtPBfqn

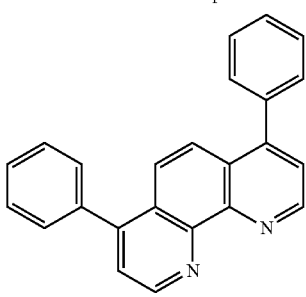

Bphen

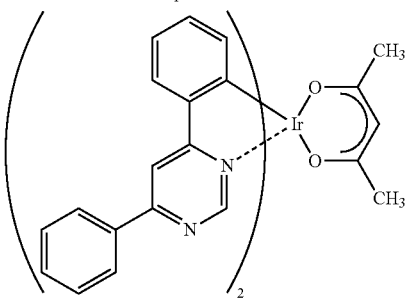

[Ir(dppm)₂(acac)]

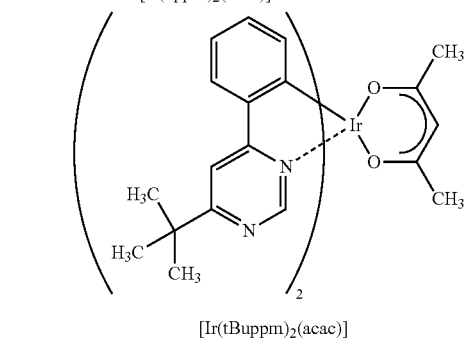

[Ir(tBuppm)₂(acac)]

<<Fabrication of Light-Emitting Elements 2 and 3>>

In each of the light-emitting elements described in this example, as illustrated in FIG. 20, the first electrode 901 was formed over the substrate 900, the EL layer 902 was formed over the first electrode 901, and the second electrode 903 was formed over the EL layer 902.

First, the first electrode 901 was formed over the substrate 900. The electrode area was set to 4 mm² (2 mm×2 mm). A glass substrate was used as the substrate 900. An indium tin oxide (ITO) containing silicon oxide was deposited over the substrate 900 by a sputtering method, whereby the first electrode 901 functioning as an anode was formed. Note that the thickness was set to 110 nm.

Next, as pretreatment for forming a light-emitting element 2 over the substrate 900, UV ozone treatment was performed for 370 seconds after washing of a surface of the substrate with water and after baking at 200° C. for 1 hour. After that, the substrate was transferred into a vacuum evaporation apparatus where the pressure had been reduced to approximately $1\times10^{-4}$ Pa, and was subjected to vacuum baking at 170° C. for 30 minutes in a heating chamber of the vacuum evaporation apparatus. Then, the substrate 900 was cooled down for approximately 30 minutes.

Then, the hole-injection layer 911, the hole-transport layer 912, the light-emitting layer 913, the electron-transport layer 914, and the electron-injection layer 915 were sequentially formed over the first electrode 901 by a vacuum evaporation method to form the EL layer 902.

After the pressure in the vacuum evaporation apparatus was reduced to $1\times10^{-4}$ Pa, the hole-injection layer 911 was formed over the first electrode 901 by co-evaporation to have a mass ratio of 1,3,5-tri(dibenzothiophen-4-yl)benzene (abbreviation: DBT3P-II) to molybdenum oxide of 4:2. The thickness was 20 nm. Note that co-evaporation is an evaporation method in which a plurality of different substances are concurrently vaporized from different evaporation sources.

Then, the hole-transport layer 912 was formed over the hole-injection layer 911. To form the hole-transport layer 912, 4-phenyl-4'-(9-phenylfluoren-9-yl)triphenylamine (abbreviation: BPAFLP) was deposited to a thickness of 20 nm.

Next, the light-emitting layer 913 was formed over the hole-transport layer 912 as follows. In the case of the light-emitting element 2, the organic compound 2mDBtPBfqn of one embodiment of the present invention and [Ir(dppm)₂(acac)] were deposited as a host material and a guest material, respectively, by co-evaporation to have a mass ratio of 2mDBtPBfqn to [Ir(dppm)₂(acac)] of 1:0.05 and a thickness of 30 nm. In the case of the light-emitting element 3, the organic compound 2mDBtPBfqn of one embodiment of the present invention and (acetylacetonato)bis(6-tert-butyl-4-phenylpyrimidinato)iridium(III) (abbreviation: [Ir(tBuppm)₂(acac)]) were deposited as a host material and a guest material, respectively, by co-evaporation to have a mass ratio of 2mDBtPBfqn to [Ir(tBuppm)₂(acac)] of 1:0.05 and a thickness of 30 nm.

Next, the electron-transport layer 914 was formed over the light-emitting layer 913. The electron-transport layer 914 was formed in the following manner: 2mDBtPBfqn and bathophenanthroline (abbreviation: Bphen) were sequentially deposited by evaporation to thicknesses of 20 nm and 10 nm, respectively.

Then, the electron-injection layer 915 was formed over the electron-transport layer 914. The electron-injection layer 915 was formed to a thickness of 1 nm by evaporation of lithium fluoride (LiF).

After that, the second electrode 903 was formed over the electron-injection layer 915. To form the second electrode 903 serving as a cathode, aluminum was deposited by evaporation to a thickness of 200 nm. In all the evaporation steps in the fabrication method, evaporation was performed by a resistance-heating method.

Each of the light-emitting elements 2 and 3 fabricated in this example was sealed between the substrate 900 and the substrate 905. The sealing between the substrate 900 and the substrate 905 was performed in such a manner that the substrate 905 was fixed to the substrate 900 with a sealing material in a glove box containing a nitrogen atmosphere, a sealant was applied so as to surround the light-emitting element formed over the substrate 900, and then irradiation with 365-nm ultraviolet light at 6 J/cm² was performed and heat treatment was performed at 80° C. for 1 hour.

<<Operation Characteristics of Light-Emitting Elements 2 and 3>>

Operation characteristics of the light-emitting elements 2 and 3 were measured. Note that the measurement was carried out at room temperature (in an atmosphere where a temperature was maintained at 25° C.). FIG. 26 to FIG. 29 show the results.

Table 4 shows initial values of main characteristics of the light-emitting elements 2 and 3 at around 1000 cd/m².

TABLE 4

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 2 | 2.8 | 0.064 | 1.6 | (0.54, 0.45) | 960 | 60 | 67 | 21 |
| Light-emitting element 3 | 2.7 | 0.046 | 1.2 | (0.41, 0.58) | 870 | 75 | 88 | 19 |

The above results show that the light-emitting elements fabricated in this example have high current efficiency and high external quantum efficiency.

Figure 30:
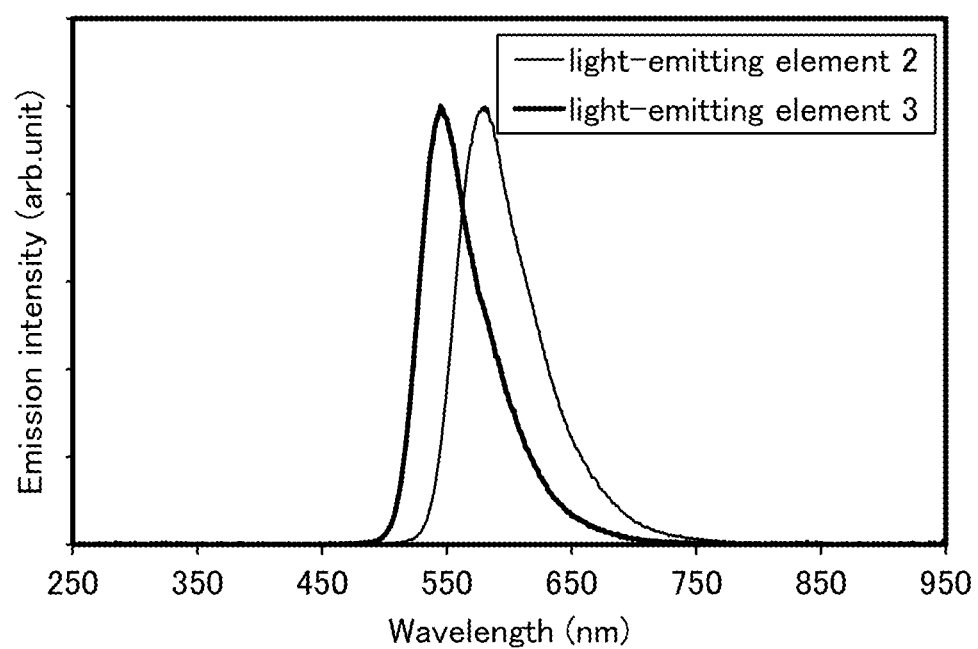
FIG. 30 shows the emission spectra of the light-emitting element 2 and the light-emitting element 3.

FIG. 30 shows emission spectra when current at a current density of 2.5 mA/cm² was applied to the light-emitting elements. As shown in FIG. 30, the emission spectrum of the light-emitting element 2 has a peak at around 580 nm that is probably derived from light emission of the organometallic complex [Ir(dppm)$_2$(acac)] contained in the light-emitting layer 913. Furthermore, the emission spectrum of the light-emitting element 3 has a peak at around 545 nm that is probably derived from light emission of the organometallic complex [Ir(tBuppm)$_2$(acac)] contained in the light-emitting layer 913. In this example, 2mDBtPBfqn contained in the light-emitting layers and the electron-transport layers has a benzofuroquinoxaline skeleton and thus has a high electron-transport property.

Example 4

Synthesis Example 2

In this example, a method for synthesizing 2,8-bis[3-(dibenzothiophen-4-yl)phenyl]benzofuro[2,3-b]quinoxaline (abbreviation: 2,8mDBtP2Bfqn) represented by Structural Formula (262) in Embodiment 1, which is the organic compound of one embodiment of the present invention, will be described. The structure of 2,8mDBtP2Bfqn is shown below.

[Chemical Formula 36]

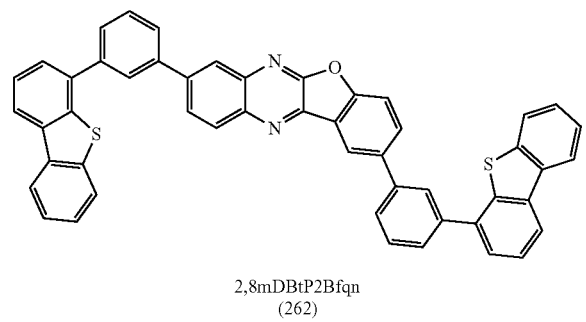

2,8mDBtP2Bfqn
(262)

Step 1: Synthesis of 7-chloro-3-(5-chloro-2-methoxyphenyl)quinoxalin-2-amine

Into a three-neck flask equipped with a reflux pipe were put 0.50 g of 3,7-dichloroquinoxalin-2-amine, 0.47 g of a 5-chloro-2-methoxyphenylboronic acid, 0.75 g of cesium carbonate, 9 mL of 1,4-dioxane, and 4.5 mL of water, and the air in the flask was replaced with nitrogen. The mixture in the flask was degassed by being stirred under reduced pressure, 0.27 g of tetrakis(triphenylphosphine)palladium(0) was added thereto, and the resulting mixture was stirred at 80° C. for 12 hours to be reacted.

After a predetermined time elapsed, 50 mL of water was added to the obtained suspension, and then suction filtration was performed. The obtained solid was washed with dichloromethane, so that a target quinoxaline derivative (yellowish white powder) was obtained in a yield of 64%. A synthesis scheme (b-1) of Step 1 is shown below.

[Chemical Formula 37]

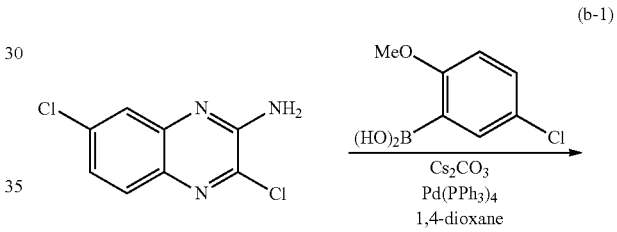

Step 2: Synthesis of 2,8-dichlorobenzofuro[2,3-b]quinoxaline

Next, into a three-neck flask were put 0.48 g of 7-chloro-3-(5-chloro-2-methoxyphenyl)quinoxalin-2-amine obtained in Step 1, 16 mL of dehydrated tetrahydrofuran, and 32 mL of a glacial acetic acid, and the air in the flask was replaced with nitrogen. After the flask was cooled down to −10° C., 0.53 mL of tert-butyl nitrite was dripped, and the resulting mixture was stirred at −10° C. for 1 hour and at 0° C. for 17 hours. After a predetermined time elapsed, 100 mL of water was added to the obtained suspension and then suction filtration was performed. The obtained solid was purified by silica gel column chromatography using toluene as a developing solvent, so that a target quinoxaline derivative (white powder) was obtained in a yield of 42%. A synthesis scheme (b-2) of Step 2 is shown below.

[Chemical Formula 38]

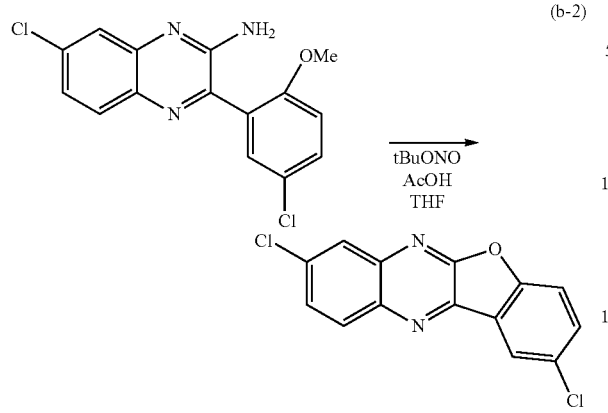

Step 3: Synthesis of 2,8-bis[3-(dibenzothiophen-4-yl)phenyl]benzofuro[2,3-b]quinoxaline (Abbreviation: 2,8mDBtP2Bfqn)

Then, into a three-neck flask were put 0.81 g of 2,8-dichlorobenzofuro[2,3-b]quinoxaline obtained in Step 2, 1.88 g of a 3-(4-dibenzothiophene)phenylboronic acid, 3.59 g of tripotassium phosphate, 23 mL of diglyme, and 1.6 mL of tert-butanol, and the air in the flask was replaced with nitrogen. The mixture in the flask was degassed by being stirred under reduced pressure, 0.013 g of palladium(II) acetate and 0.043 g of di(1-adamantyl)-n-butylphosphine (abbreviation: CataCXiumA) were added thereto, and the resulting mixture was stirred at 140° C. for 7 hours to be reacted.

After a predetermined time elapsed, the obtained suspension was subjected to suction filtration and was washed with water and ethanol. The obtained solid was purified by silica gel column chromatography using toluene as a developing solvent, and then recrystallization from a mixed solvent of toluene and hexane was performed; thus, target yellowish white powder was obtained in a yield of 52%. By a train sublimation method, 0.95 g of the obtained yellowish white powder solid was purified. In the purification by sublimation, the solid was heated at 370° C. under a pressure of 2.6 Pa with a flow rate of an argon gas of 5 mL/min. After the purification by sublimation, a target pale yellow solid was obtained in a yield of 86%. A synthesis scheme (b-3) of Step 3 is shown below.

[Chemical Formula 39]

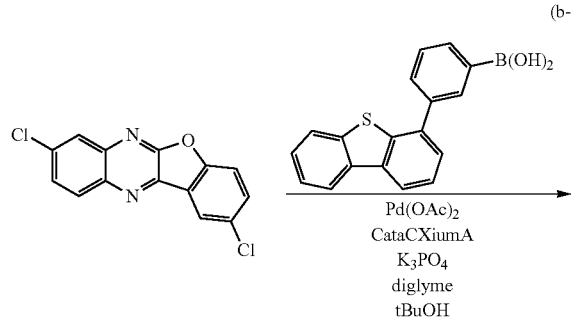

2,8mDBtP2Bfqn
(262)

Figure 33:
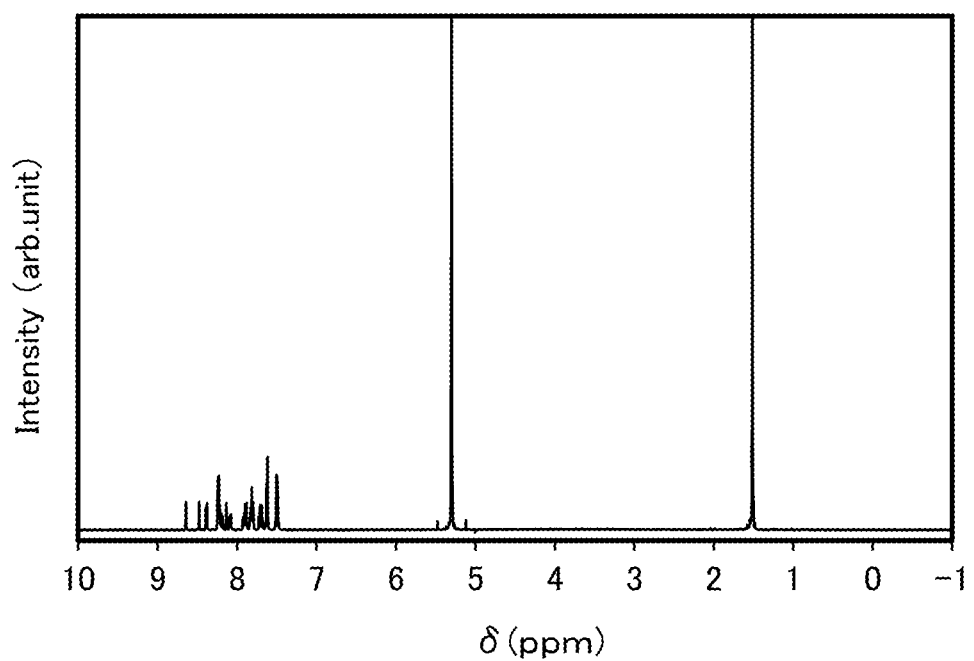
FIG. 33 is the $^1$H-NMR chart of an organic compound represented by Structural Formula (262).

Analysis results by nuclear magnetic resonance (H-NMR) spectroscopy of the pale yellow solid obtained in Step 3 are shown below. FIG. 33 shows the $^1$H-NMR chart. The results revealed that 2,8mDBtP2Bfqn, the organic compound of one embodiment of the present invention represented by Structural Formula (262), was obtained in this example.

$^1$H-NMR (CD$_2$Cl$_2$, 500 MHz): δ=7.54-7.50 (m, 4H), 7.64-7.66 (m, 4H), 7.69-7.75 (m, 2H), 7.81-7.86 (m, 4H), 7.90-7.95 (m, 3H), 8.11 (dd, 1H), 8.15 (s, 1H), 8.21 (dd, 1H), 8.24-8.27 (m, 5H), 8.40 (d, 1H), 8.50 (d, 1H), 8.66 (d, 1H).

Figure 34:
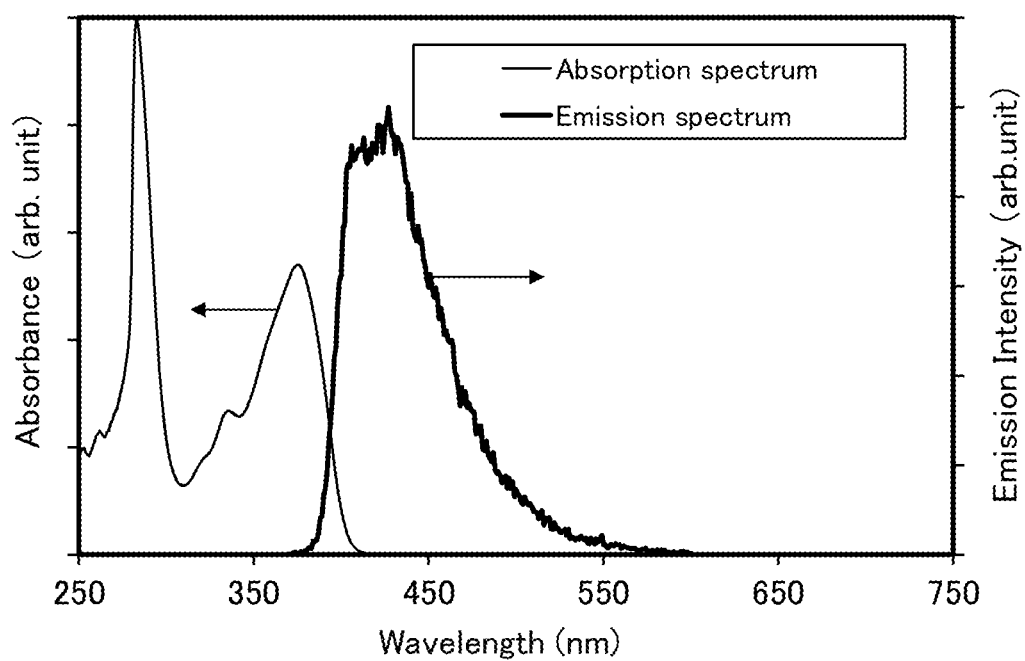
FIG. 34 shows the ultraviolet-visible absorption spectrum and the emission spectrum of the organic compound represented by Structural Formula (262) in a solution.

Then, the ultraviolet-visible absorption spectrum (hereinafter, simply referred to as "absorption spectrum") and emission spectrum of 2,8mDBtP2Bfqn in a toluene solution were measured. The absorption spectrum was measured with an ultraviolet-visible light spectrophotometer (V550 type, produced by JASCO Corporation). The emission spectrum was measured with a fluorescence spectrophotometer (FS920, produced by Hamamatsu Photonics K.K.). FIG. 34 shows the measurement results of the absorption and emission spectra of 2,8mDBtP2Bfqn in the toluene solution. The horizontal axis represents the wavelength and the vertical axes represent the absorbance and emission intensity.

FIG. 34 shows that 2,8mDBtP2Bfqn in the toluene solution has absorption peaks at around 283 nm, 336 nm, and 375 nm, and an emission wavelength peak at around 427 nm.

Figure 35:
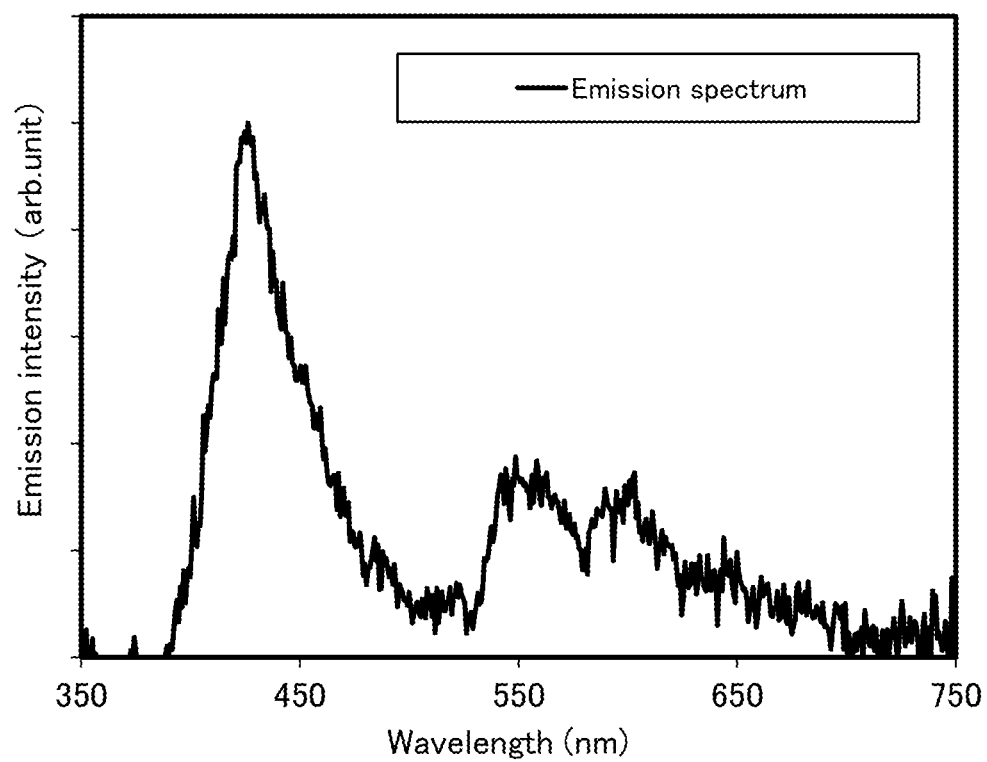
FIG. 35 shows the emission spectrum of the organic compound represented by Structural Formula (262).

Next, the emission spectrum of 2,8mDBtP2Bfqn in the toluene solution was measured at low temperatures. The emission spectrum was measured at 77 K in such a manner that an absolute PL quantum yield measurement system (C11347-01, produced by Hamamatsu Photonics K.K.) was used and a deoxidized toluene solution was sealed in a quartz cell under a nitrogen atmosphere in a glove box (LABstar M13 (1250/780), produced by Bright Co., Ltd.). FIG. 35 shows the measurement result of the emission spectrum. The horizontal axis represents the wavelength and the vertical axis represents the emission intensity.

The results in FIG. 35 show that 2,8mDBtP2Bfqn in the toluene solution has an emission wavelength peak at around 426 nm. The peak is also observed in the emission spectrum shown in FIG. 34, which is obtained at room temperature, and thus is probably derived from a fluorescence emission spectrum. In addition, emission wavelength peaks can be observed at around 550 nm and around 600 nm. These peaks are not observed in the emission spectrum shown in FIG. 34, which is obtained at room temperature, but in the emission spectrum obtained in this measurement performed at a temperature of liquid nitrogen (77 K) at which thermal deactivation can be inhibited and in a deoxygenated solvent not affected by oxygen. Thus, the peaks are probably derived from a phosphorescence emission spectrum. This means that 2,8mDBtP2Bfqn is a phosphorescent host material that is suitably used with a guest material that emits light with energy at a wavelength longer than that of yellowish green light.

Next, a specific example of the LUMO level of 2,8mDBtP2Bfqn is described. The LUMO level was estimated from the values of an oxidation potential, a reduction potential, and potential energy (approximately −4.94 eV with respect to the vacuum level) of a reference electrode (Ag/Ag$^+$), which were obtained by cyclic voltammetry (CV) measurement in a dimethylformamide solvent. Specifically, the LUMO level was "−4.94 [eV]−(the value of the oxidation potential or reduction potential)." The measurement value of the LUMO level calculated using the above formula was −3.31 eV. This indicates that 2,8mDBtP2Bfqn accepts electrons easily and has high electron stability.

Differential scanning calorimetry was also performed on 2,8mDBtP2Bfqn. For the calorimetry, a differential scanning calorimeter (Pyris 1, produced by PerkinElmer Japan Co., Ltd.) was used. One cycle in the calorimetry was as follows: the temperature was increased from −10° C. to 400° C. at a rate of 30° C./min, kept at 400° C. for 1 minute, and decreased from 400° C. to −10° C. at a rate of 30° C./min. In the calorimetry, three cycles were performed. From the result at the rising temperature in the second cycle, it was found that the glass transition temperature ($T_g$) was 151° C. This indicates that 2,8mDBtP2Bfqn has high heat resistance.

Example 5

Synthesis Example 3

In this example, a method for synthesizing 2,9-bis[3-(dibenzothiophen-4-yl)phenyl]benzofuro[2,3-b]quinoxaline (abbreviation: 2,9mDBtP2Bfqn) represented by Structural Formula (200) in Embodiment 1, which is the organic compound of one embodiment of the present invention, will be described. The structure of 2,9mDBtP2Bfqn is shown below.

[Chemical Formula 40]

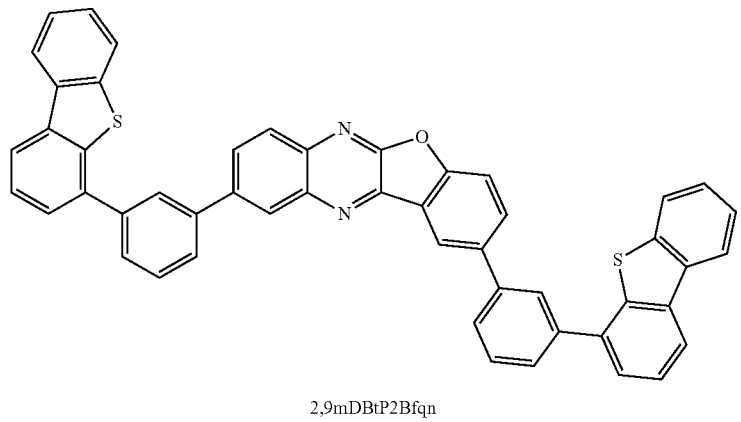

2,9mDBtP2Bfqn (200)

Step 1: Synthesis of 2,6-dichloro-3-(5-chloro-2-methoxyphenyl)quinoxaline

Into a three-neck flask equipped with a reflux pipe were put 2.03 g of 2,3,6-trichloroquinoxaline, 1.84 g of a 5-chloro-2-methoxyphenylboronic acid, 2.80 g of cesium carbonate, 34 mL of 1,4-dioxane, and 17 mL of water, and the air in the flask was replaced with nitrogen. The mixture in the flask was degassed by being stirred under reduced pressure, 0.99 g of tetrakis(triphenylphosphine)palladium(0) was added thereto, and the resulting mixture was stirred at 80° C. for 6 hours to be reacted.

After a predetermined time elapsed, 100 mL of water was added to the obtained suspension, and then suction filtration was performed. The obtained solid was purified by silica gel column chromatography using a developing solvent in which the ratio of hexane to ethyl acetate was 10:1, so that 0.46 g of a target quinoxaline derivative (yellowish white powder) was obtained in a yield of 16%. A synthesis scheme (c-1) of Step 1 is shown below.

[Chemical Formula 41]

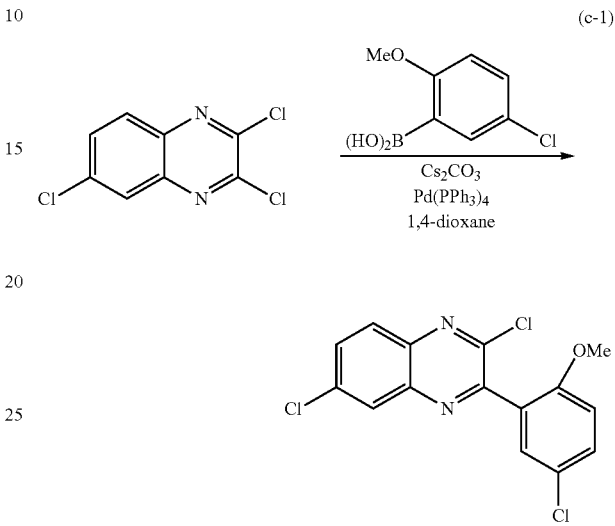

(c-1)

Step 2: Synthesis of 2,6-dichloro-3-(5-chloro-2-hydroxyphenyl)quinoxaline

Next, into a three-neck flask were put 0.46 g of 2,6-dichloro-3-(5-chloro-2-methoxyphenyl)quinoxaline obtained in Step 1 and 10 mL of dehydrated dichloromethane, and the air in the flask was replaced with nitrogen. After the flask was cooled down to −10° C., 2.8 mL of boron tribromide (a 1M dichloromethane solution) was dripped, and the resulting mixture was stirred at room temperature for 16 hours. After a predetermined time elapsed, the obtained suspension was added to 10 mL of water. Then, 15 mL of a saturated aqueous solution of sodium hydrogen carbonate was added to the mixture, and extraction with dichloromethane was performed. The obtained residue was purified by flash column chromatography using a developing solvent in which the ratio of dichloromethane to hexane was 2:1, so that 0.30 g of a target quinoxaline derivative (yellow powder) was obtained in a yield of 68%. A synthesis scheme (c-2) of Step 2 is shown below.

[Chemical Formula 42]

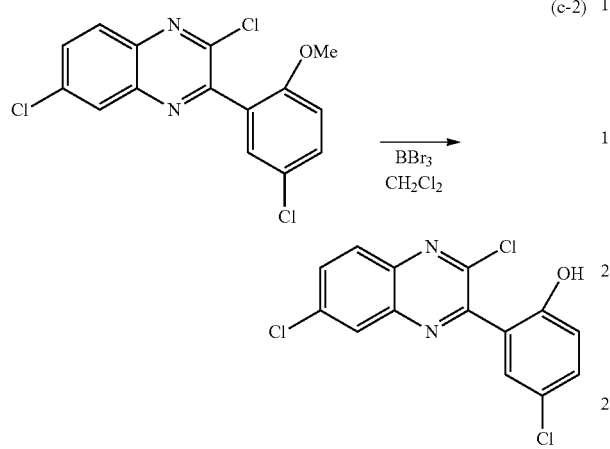

(c-2)

Step 3: Synthesis of 2,9-dichlorobenzofuro[2,3-b]quinoxaline

Then, into a three-neck flask were put 0.30 g of 2,6-dichloro-3-(5-chloro-2-hydroxyphenyl)quinoxaline obtained in Step 2 and 5 mL of dehydrated N-methyl-2-pyrrolidone (NMP), and the air in the flask was replaced with nitrogen. To the mixture was added 0.26 g of potassium carbonate, and stirring was performed at 160° C. for 7 hours. After a predetermined time elapsed, extraction with toluene was performed. The obtained residue was purified by silica gel column chromatography using a developing solvent in which the ratio of hexane to ethyl acetate was 10:1, so that 30 mg of a target quinoxaline derivative (yellowish white powder) was obtained in a yield of 11%. A synthesis scheme (c-3) of Step 3 is shown below.

[Chemical Formula 43]

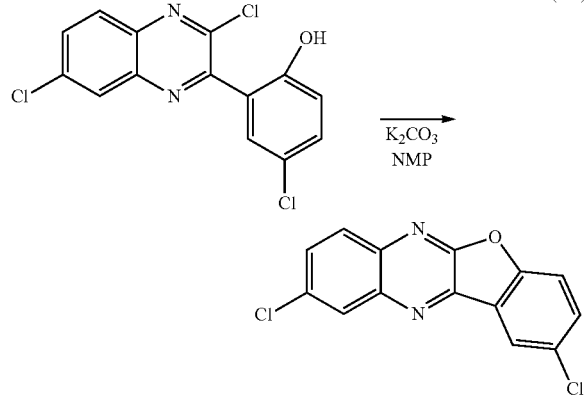

(c-3)

Step 4: Synthesis of 2,9-bis[3-(dibenzothiophen-4-yl)phenyl]benzofuro[2,3-b]quinoxaline (Abbreviation: 2,9mDBtP2Bfqn)

Then, into a three-neck flask were put 27 mg of 2,9-dichlorobenzofuro[2,3-b]quinoxaline obtained in Step 3, 0.15 g of a 3-(4-dibenzothiophene)phenylboronic acid, 0.30 g of tripotassium phosphate, 2 mL of diglyme, and 53 mg of tert-butanol, and the air in the flask was replaced with nitrogen. The mixture in the flask was degassed by being stirred under reduced pressure, 0.86 mg of palladium(II) acetate and 2.8 mg of di(1-adamantyl)-n-butylphosphine (abbreviation: CataCXiumA) were added thereto, and the resulting mixture was stirred at 140° C. for 17 hours to be reacted.

After a predetermined time elapsed, the obtained suspension was subjected to suction filtration and was washed with water and ethanol. The obtained residue was purified by silica gel column chromatography using toluene as a developing solvent, and then recrystallization from toluene was performed; thus, 17 mg of target yellowish white powder was obtained in a yield of 25%. A synthesis scheme (c-4) of Step 4 is shown below.

[Chemical Formula 44]

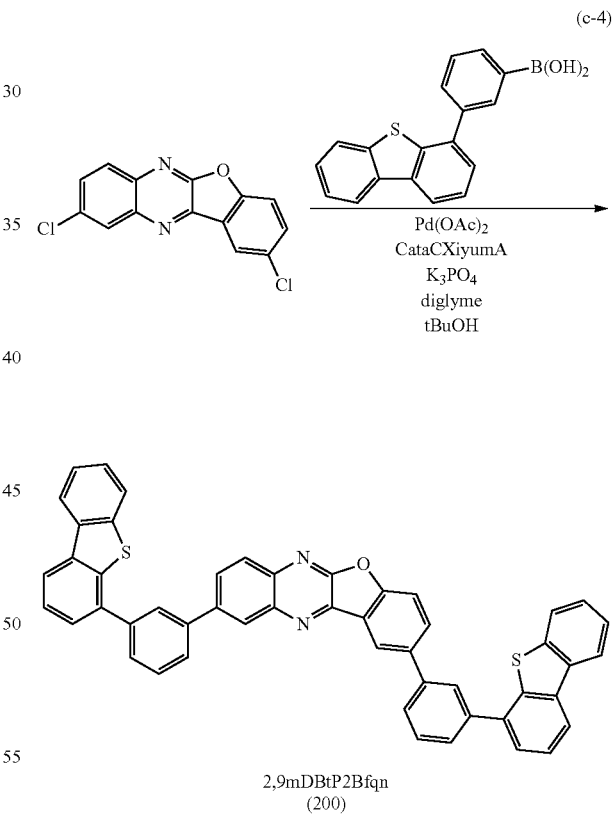

(c-4)

Figure 36:
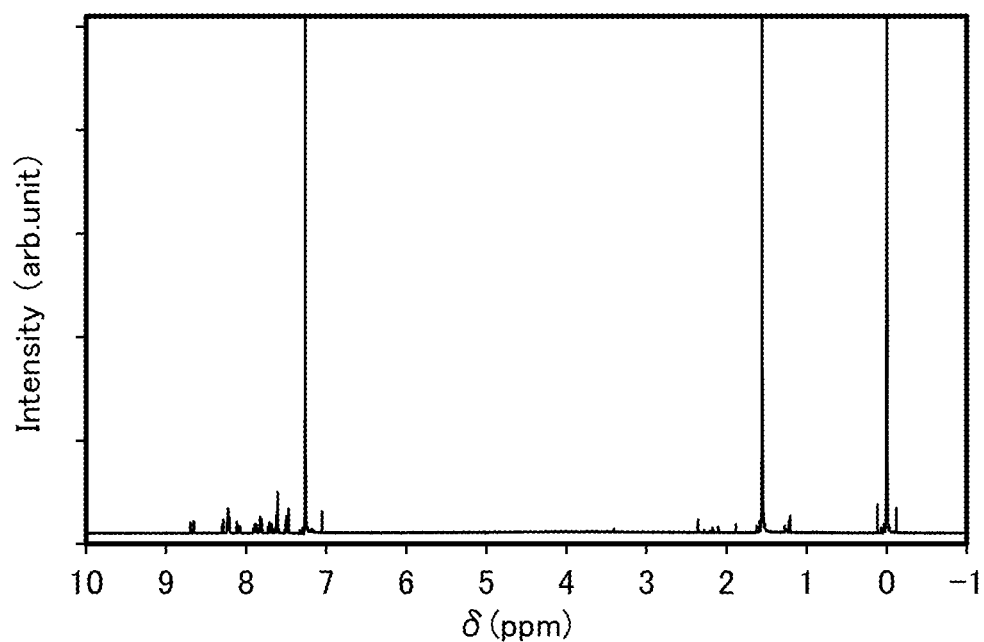
FIG. 36 is the $^1$H-NMR chart of an organic compound represented by Structural Formula (200).

Analysis results by nuclear magnetic resonance ($^1$H-NMR) spectroscopy of the yellowish white powder obtained in Step 4 are shown below. FIG. 36 shows the 1H-NMR chart. The results revealed that 2,9mDBtP2Bfqn, the organic compound of one embodiment of the present invention represented by Structural Formula (200), was obtained in this example.

$^1$H-NMR (CD$_2$Cl$_2$, 500 MHz): δ=7.48-7.52 (m, 4H), 7.59-7.64 (m, 4H), 7.67-7.73 (m, 2H), 7.81-7.84 (m, 4H), 7.87-7.91 (m, 3H), 8.08 (dd, 1H), 8.12 (s, 1H), 8.21-8.24 (dd, 6H), 8.29 (d, 1H), 8.65 (d, 1H), 8.69 (d, 1H).

Figure 44:
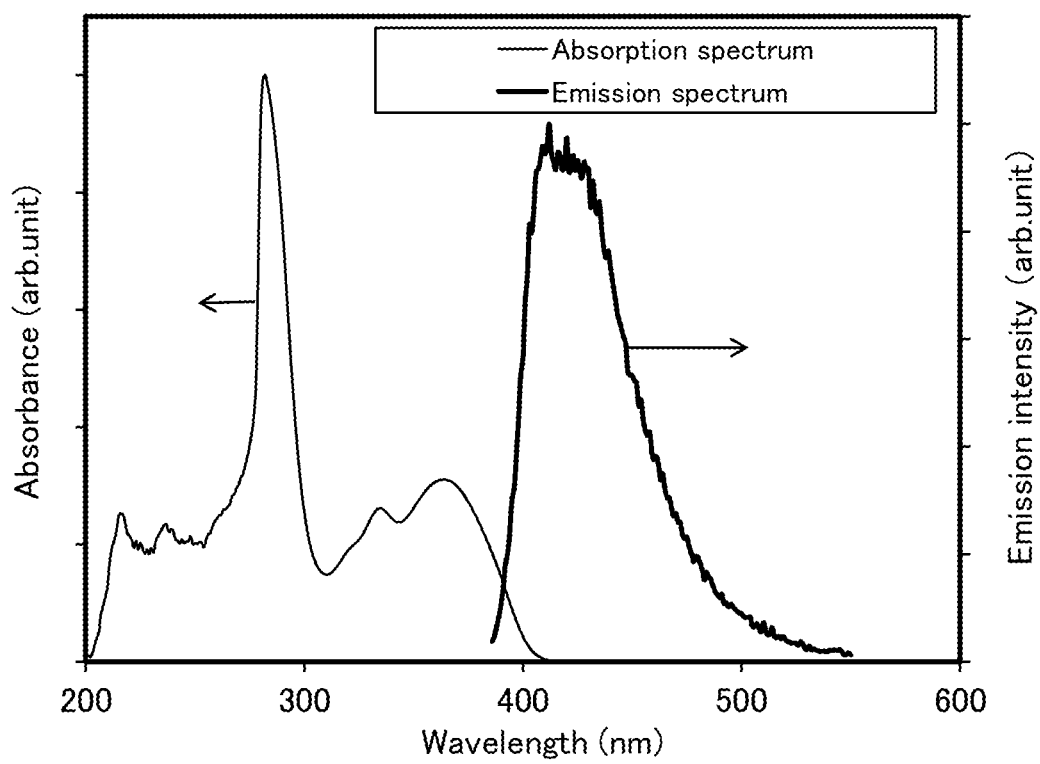
FIG. 44 shows the ultraviolet-visible absorption spectrum and the emission spectrum of the organic compound represented by Structural Formula (200) in a solution.

Then, the ultraviolet-visible absorption spectrum (hereinafter, simply referred to as "absorption spectrum") and emission spectrum of 2,9mDBtP2Bfqn in a toluene solution were measured. The absorption spectrum was measured with an ultraviolet-visible light spectrophotometer (V550 type, produced by JASCO Corporation). The emission spectrum was measured with a fluorescence spectrophotometer (FS920, produced by Hamamatsu Photonics K.K.). FIG. 44 shows the measurement results of the absorption and emission spectra of 2,9mDBtP2Bfqn in the toluene solution. The horizontal axis represents the wavelength and the vertical axes represent the absorbance and emission intensity.

FIG. 44 shows that 2,9mDBtP2Bfqn in the toluene solution has absorption peaks at around 282 nm, 335 nm, and 364 nm, and an emission wavelength peak at around 412 nm.

Figure 37:
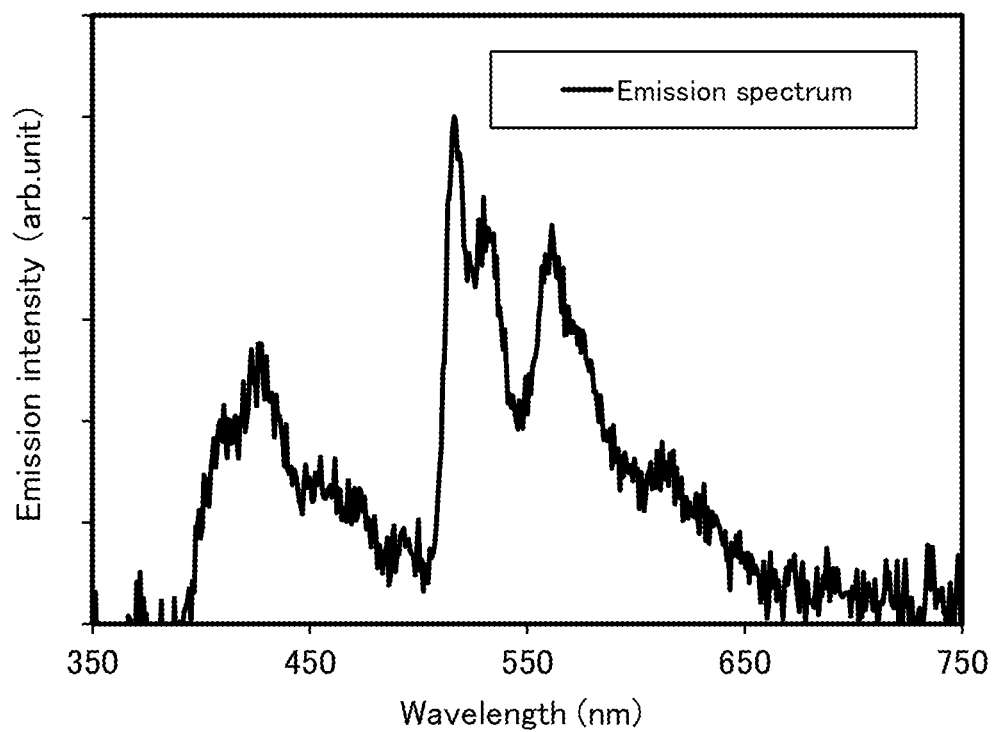
FIG. 37 shows the emission spectrum of the organic compound represented by Structural Formula (200).
Figure 38:
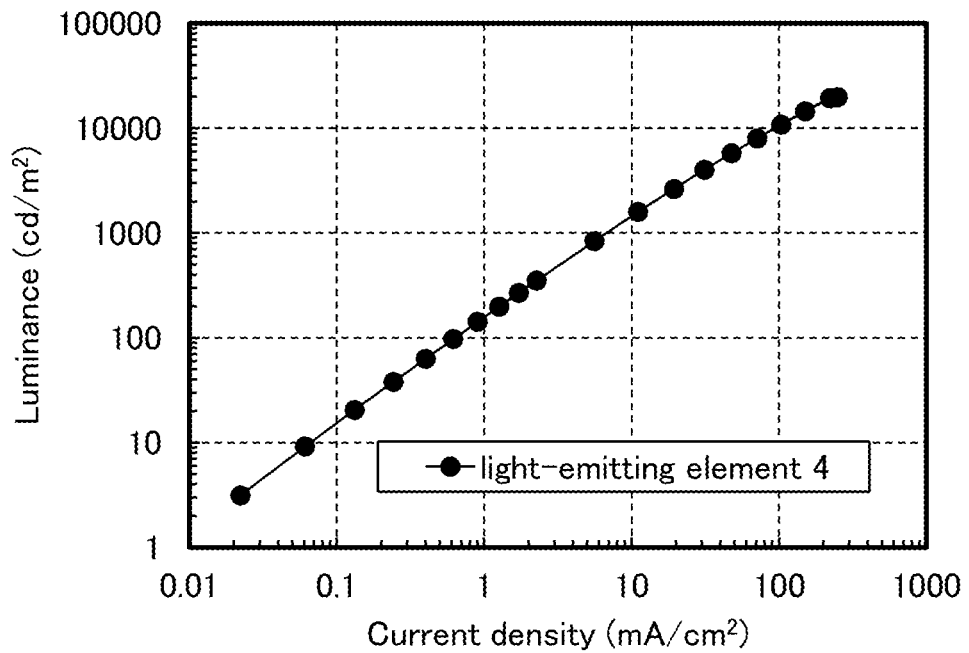
FIG. 38 shows the current density-luminance characteristics of a light-emitting element 4.
Figure 39:
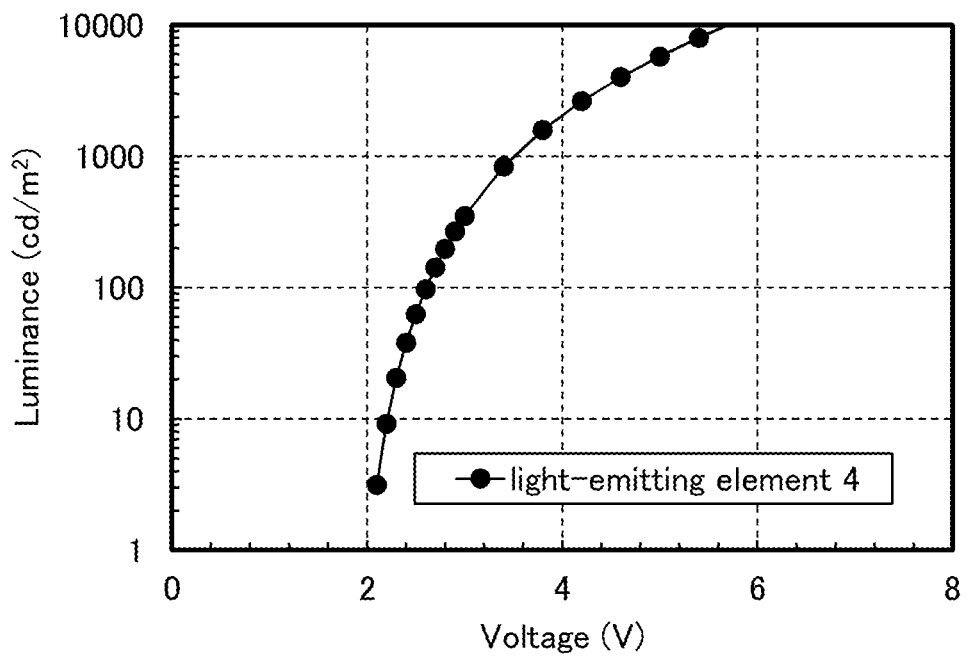
FIG. 39 shows the voltage-luminance characteristics of the light-emitting element 4.
Figure 40:
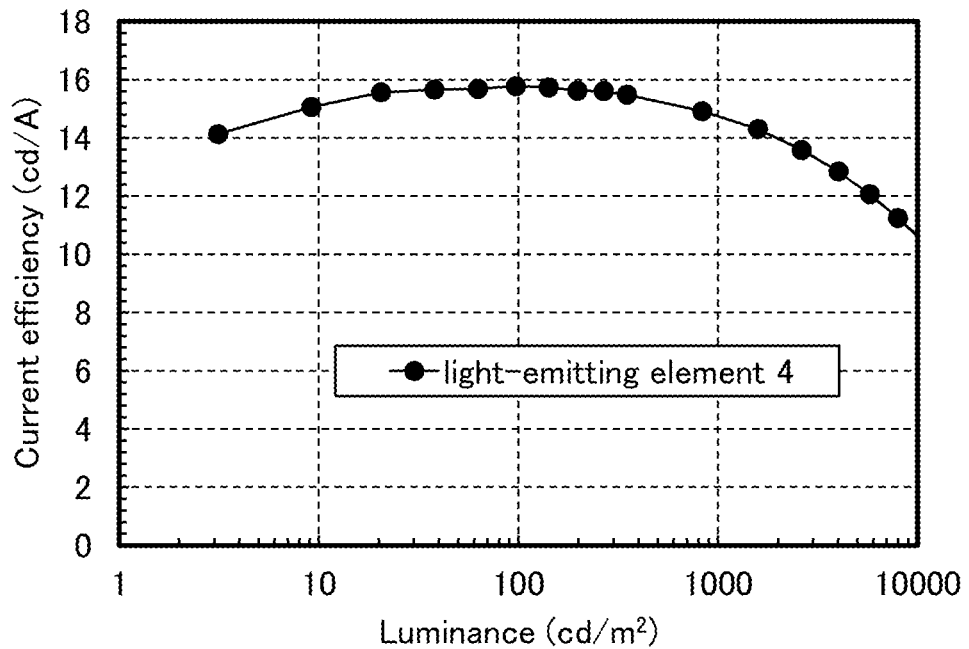
FIG. 40 shows the luminance-current efficiency characteristics of the light-emitting element 4.
Figure 41:
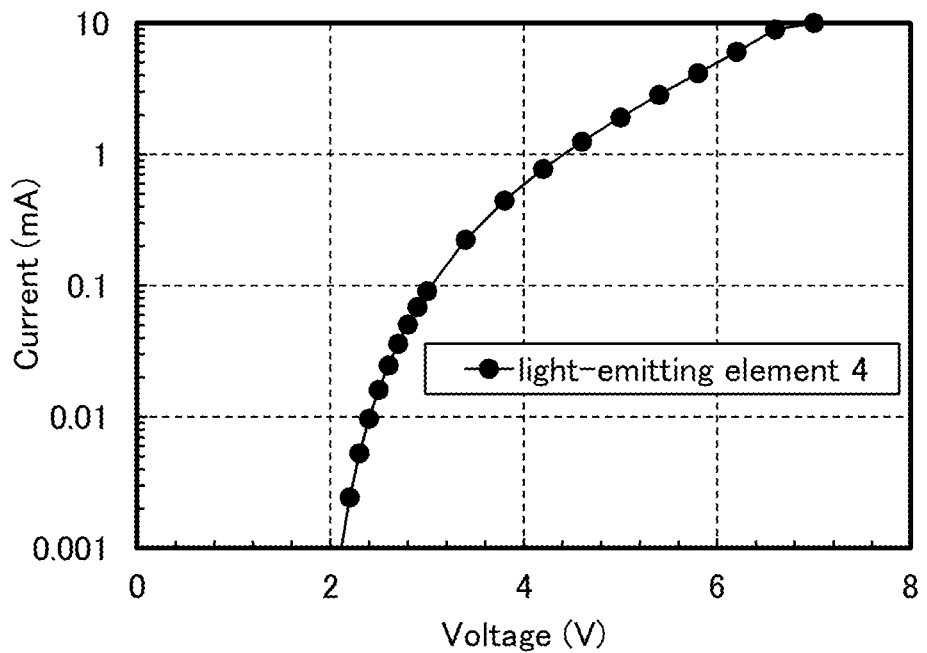
FIG. 41 shows the voltage-current characteristics of the light-emitting element 4.

Next, the emission spectrum of 2,9mDBtP2Bfqn in the toluene solution was measured at low temperatures. The emission spectrum was measured at 77 K in such a manner that an absolute PL quantum yield measurement system (C11347-01, produced by Hamamatsu Photonics K.K.) was used and a deoxidized toluene solution was sealed in a quartz cell under a nitrogen atmosphere in a glove box (LABstar M13 (1250/780), produced by Bright Co., Ltd.). FIG. 37 shows the measurement result of the emission spectrum. The horizontal axis represents the wavelength and the vertical axis represents the emission intensity.

The results in FIG. 37 show that 2,9mDBtP2Bfqn in the toluene solution has an emission wavelength peak at around 426 nm. Thus, the peak is probably derived from a fluorescence emission spectrum. In addition, emission wavelength peaks can be observed at 516 nm, around 530 nm, and around 560 nm. Thus, the peaks are probably derived from a phosphorescence emission spectrum. The attribution of the fluorescence and phosphorescence emission spectra is made on the assumption that light emission at room temperature is fluorescent light emission, as in the results of 2,8mDBtP2Bfqn in Synthesis example 2. This means that 2,9mDBtP2Bfqn is a phosphorescent host material that is suitably used with a guest material that emits light with energy at a wavelength longer than that of green light.

Example 6

In this example, an element structure of a light-emitting element in which a light-emitting layer contained the organic compound 2,8mDBtP2Bfqn of one embodiment of the present invention (Structural Formula (262)) will be described. Note that the stacked-layer structure of the light-emitting element described in this example was similar to that described in Example 2 except for some materials; thus, FIG. 20 can be referred to for the stacked-layer structure, and the description of the fabrication method is not described. Table 5 shows the specific structure of a light-emitting element 4 described in this example. Chemical formulae of materials used in this example are shown below.

[Chemical Formulae 45]

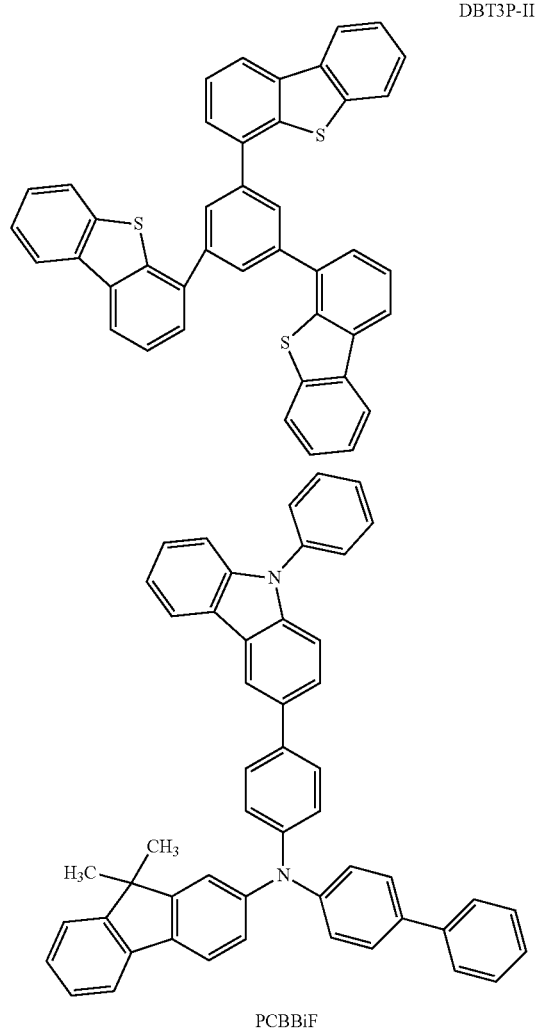

(262)

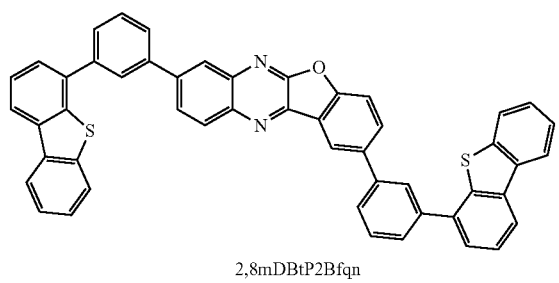

TABLE 5

|  | First electrode | Hole-injection layer | Hole-transport layer | Light-emitting layer | Electron-transport layer | Electron-injection layer | Second electrode |
|---|---|---|---|---|---|---|---|
| Light-emitting element 4 | ITO (70 nm) | DBT3P-II:MoOx (2:1, 75 nm) | BPAFLP (20 nm) | * | 2,8mDBtPBfqn (30 nm) | NBphen (15 nm) | LiF (1 nm) | Al (200 nm) |

* 2,8mDBtPBfqn:PCBBiF:[Ir(dmdppr-P)$_2$(dibm)] (0.5:0.5:0.1 (20 nm)\0.8:0.2:0.1 (20 nm))

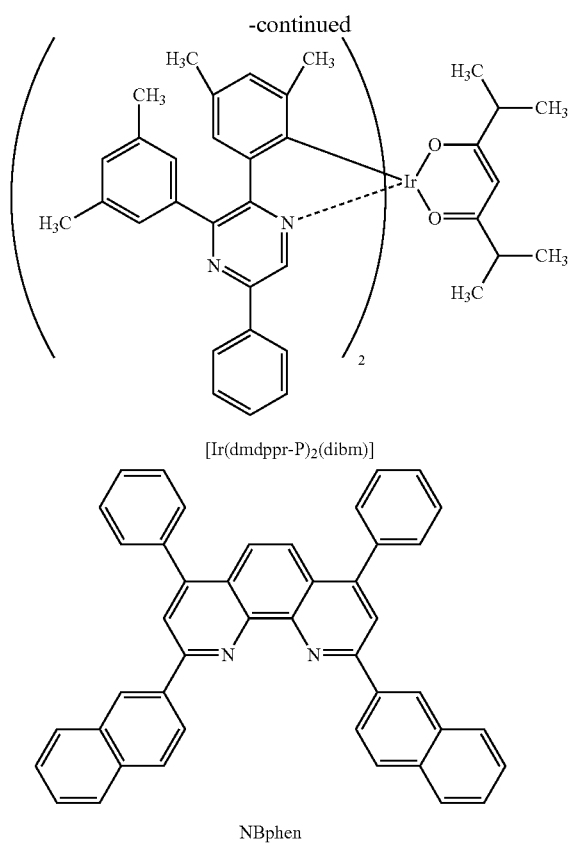

[Ir(dmdppr-P)₂(dibm)]

NBphen

<<Operation Characteristics of Light-Emitting Element 4>>

Operation characteristics of the light-emitting element 4 were measured. Note that the measurement was carried out at room temperature (in an atmosphere where a temperature was maintained at 25° C.). FIG. 38 to FIG. 41 show the results.

Table 6 shows initial values of main characteristics of the light-emitting element 4 at around 1000 cd/m².

TABLE 6

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 4 | 3.4 | 0.22 | 5.6 | (0.71, 0.29) | 840 | 15 | 14 | 27 |

The above results show that the light-emitting element fabricated in this example has high current efficiency and high external quantum efficiency.

Figure 42:
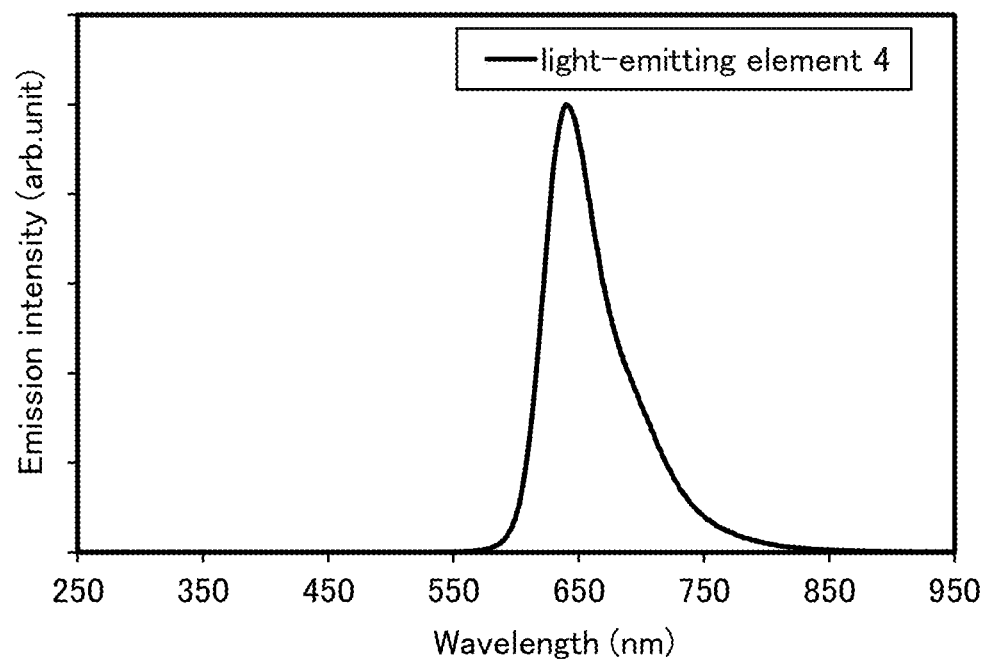
FIG. 42 shows the emission spectrum of the light-emitting element 4.

FIG. 42 shows an emission spectrum when current at a current density of 2.5 mA/cm² was applied to the light-emitting element. As shown in FIG. 42, the emission spectrum of the light-emitting element 4 has a peak at around 640 nm that is probably derived from light emission of the organometallic complex [Ir(dmdppr-P)₂(dibm)] contained in the light-emitting layer 913.

Figure 43:
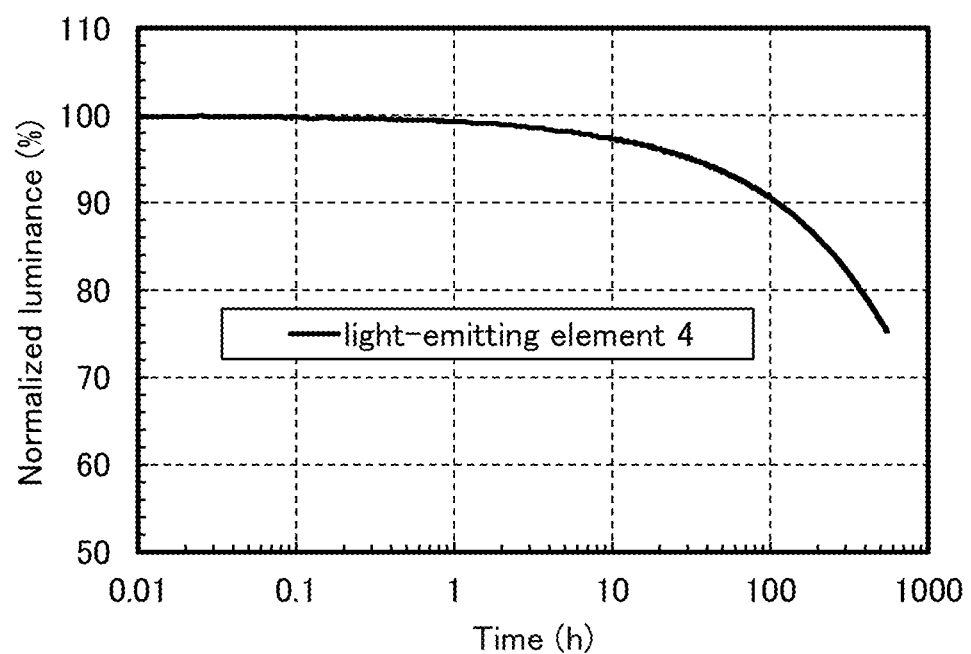
FIG. 43 shows the reliability of the light-emitting element 4.

Next, a reliability test of the light-emitting element 4 was conducted. FIG. 43 shows the results of the reliability test. In FIG. 43, the vertical axis represents normalized luminance (%) with an initial luminance of 100%, and the horizontal axis represents driving time (h) of the element. Note that the reliability test was conducted while the light-emitting element was driven at a current density of 50 mA/cm².

The results indicate that the light-emitting element 4 has high reliability in addition to high external quantum efficiency.

In the light-emitting layer of this example, 2,8mDBtP2Bfqn and PCBBiF form an exciplex, and light emission due to energy transfer from the exciplex to the light-emitting substance [Ir(dmdppr-P)₂(dibm)] (ExTET) can be obtained. Note that 2,8mDBtP2Bfqn, which is one embodiment of the present invention, has a benzofuroquinoxaline skeleton and a deep LUMO level and thus is suitable for forming an exciplex. Since light emission due to ExTET can be obtained in the light-emitting element described in this example, driving voltage can be reduced.

Furthermore, 2,8mDBtP2Bfqn is suitably used not only for the light-emitting layer but also for the electron-transport layer in this example because 2,8mDBtP2Bfqn has a benzofuroquinoxaline skeleton and thus has a high electron-transport property.

REFERENCE NUMERALS

101: first electrode, 102: second electrode, 103: EL layer, 103a: EL layer, 103b: EL layer, 104: charge generation layer, 111: hole-injection layer, 111a: hole-injection layer, 111b: hole-injection layer, 112: hole-transport layer, 112a: hole-transport layer, 112b: hole-transport layer, 113: light-emitting layer, 113a: light-emitting layer, 113b: light-emitting layer, 114: electron-transport layer, 114a: electron-transport layer, 114b: electron-transport layer, 115: electron-injection layer, 115a: electron-injection layer, 115b: electron-injection layer, 301: first substrate, 302: transistor (FET), 303: light-emitting element, 303R: light-emitting element, 303G: light-emitting element, 303B: light-emitting element, 303W: light-emitting element, 304: EL layer, 305: second substrate, 306R: color filter, 306G: color filter, 306B: color filter, 307: first electrode, 308: second electrode, 309: black layer (black matrix), 401: first substrate, 402: pixel portion, 403: driver circuit portion, 404a: driver circuit portion, 404b: driver circuit portion, 405: sealant, 406: second substrate, 407: lead wiring, 408: FPC (flexible print circuit), 409: FET, 410: FET, 411: FET (switching FET), 412: FET (current control FET), 413: first electrode, 414: insulator, 415: EL layer, 416: second electrode, 417: light-emitting element, 418: space, 900: substrate, 901: first electrode, 902: EL layer, 903: second electrode, 911: hole-injection layer, 912: hole-transport layer, 913: light-emitting layer, 914: electron-transport layer, 915: electron-injection layer, 2000: touch panel, 2000': touch panel, 2501: display panel, 2502R: pixel, 2502t: transistor, 2503c: capacitor, 2503g: scan line driver circuit, 2503t: transistor, 2509: FPC, 2510: substrate, 2511: wiring, 2519: terminal, 2521: insulating layer, 2528: insulator, 2550R: light-emitting element, 2560: sealing layer, 2567BM: light-blocking layer, 2567p: anti-reflection layer, 2567R: coloring layer, 2570: substrate, 2590: substrate, 2591: electrode, 2592: electrode, 2593: insulating layer, 2594: wiring, 2595: touch sensor, 2597: adhesive layer, 2598: wiring, 2599: terminal, 2601: pulse voltage output circuit, 2602: current sensing circuit, 2603: capacitor, 2611: transistor, 2612: transistor, 2613: transistor, 2621: electrode, 2622: electrode, 3000: display device, 3001: circuit (G), 3002: circuit (S), 3003: display portion, 3004: pixel, 3005:

conductive film, 3007: opening, 3010: liquid crystal element, 3011: light-emitting element, 3015: transistor, 3016: transistor, 3017: transistor, 3018: terminal portion, 3019: terminal portion, 3021: substrate, 3022: substrate, 3023: light-emitting element, 3024: liquid crystal element, 3025: insulating layer, 3028: coloring layer, 3029: adhesive layer, 3030: conductive layer, 3031: EL layer, 3032: conductive layer, 3033: opening, 3034: coloring layer, 3035: light-blocking layer, 3036: structure, 3037: conductive layer, 3038: liquid crystal, 3039: conductive layer, 3040: alignment film, 3041: alignment film, 3042: adhesive layer, 3043: conductive layer, 3044: FPC, 3045: connection layer, 3046: insulating layer, 3047: connection portion, 3048: connector, 4000: lighting device, 4001: substrate, 4002: light-emitting element, 4003: substrate, 4004: electrode, 4005: EL layer, 4006: electrode, 4007: electrode, 4008: electrode, 4009: auxiliary wiring, 4010: insulating layer, 4011: sealing substrate, 4012: sealant, 4013: desiccant, 4015: diffusion plate, 4100: lighting device, 4200: lighting device, 4201: substrate, 4202: light-emitting element, 4204: electrode, 4205: EL layer, 4206: electrode, 4207: electrode, 4208: electrode, 4209: auxiliary wiring, 4210: insulating layer, 4211: sealing substrate, 4212: sealant, 4213: barrier film, 4214: planarization film, 4215: diffusion plate, 4300: lighting device, 5101: light, 5102: wheel cover, 5103: door, 5104: display portion, 5105: steering wheel, 5106: gear lever, 5107: seat, 5108: inner rearview mirror, 7100: television device, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7302: housing, 7304: display portion, 7305: icon, 7306: icon, 7311: operation button, 7312: operation button, 7313: connection terminal, 7321: band, 7322: clasp, 7400: mobile phone, 7401: housing, 7402: display portion, 7403: operation button, 7404: external connection portion, 7405: speaker, 7406: microphone, 7407: camera, 7500(1): housing, 7500(2): housing, 7501(1): first screen, 7501(2): first screen, 7502(1): second screen, 7502(2): second screen, 8001: ceiling light, 8002: foot light, 8003: sheet-like lighting, 8004: lighting device, 9310: portable information terminal, 9311: display portion, 9312: display region, 9313: hinge, and 9315: housing.

This application is based on Japanese Patent Application Serial No. 2016-159794 filed with Japan Patent Office on Aug. 17, 2016 and Japanese Patent Application Serial No. 2017-102066 filed with Japan Patent Office on May 23, 2017, the entire contents of which are hereby incorporated by reference.

The invention claimed is:

1. An organic compound represented by General formula (a1):

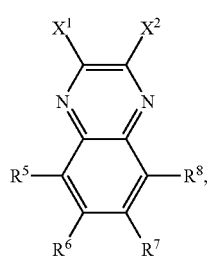

(a1)

wherein $X^1$ represents any one of a halogeno group, a triflate group, and an amino group,
wherein $X^2$ represents a triflate group,
wherein each of $R^5$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms, and
wherein, in the case where none of $R^5$ to $R^8$ is a halogeno group, at least one of $R^5$ to $R^8$ comprises a substituted or unsubstituted condensed aromatic ring having 10 to 24 carbon atoms or a substituted or unsubstituted condensed heteroaromatic ring having 10 to 24 carbon atoms.

2. The organic compound according to claim 1, wherein the $X^1$ represents a halogeno group.

3. The organic compound according to claim 2, wherein the $X^1$ represents a fluorine or chlorine.

4. The organic compound according to claim 1, wherein the $X^1$ represents an amino group.

5. The organic compound according to claim 1, wherein the $X^1$ represents a triflate group.

6. The organic compound according to claim 1, wherein at least one of $R^5$ to $R^8$ comprises any of substituted or unsubstituted naphthalene, fluorene, phenanthrene, triphenylene, dibenzothiophene, dibenzofuran, and carbazole rings.

7. The organic compound according to claim 1,
wherein at least one of $R^5$ to $R^8$ comprises any of a substituted or unsubstituted arylene group having 6 to 24 carbon atoms or a substituted or unsubstituted heteroarylene group having 3 to 24 carbon atoms.

8. The organic compound according to claim 1,
wherein at least one of $R^5$ to $R^8$ represents any of General Formulae (A-1) to (A-4):

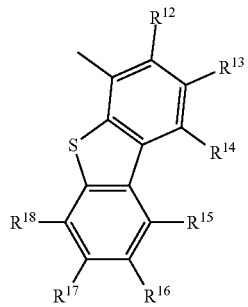

(A-1)

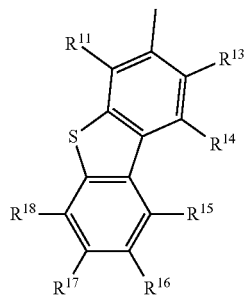

(A-2)

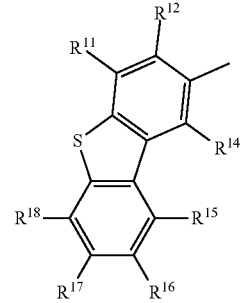

(A-3)

-continued

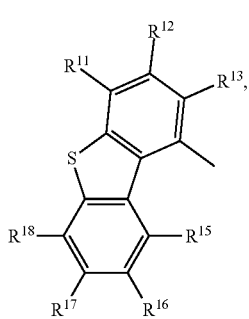
(A-4)

wherein each of R¹ to R¹⁸ independently represents any of hydrogen, an alkyl group having 1 to 6 carbon atoms, and a substituted or unsubstituted phenyl group.

9. An organic compound represented by General formula (a1):

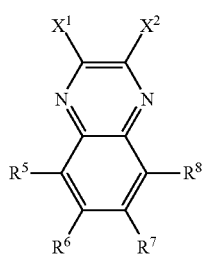
(a1)

wherein X¹ represents a halogeno group,
wherein X¹ represents a primary amino group,
wherein each of R⁵ to R⁸ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms,
wherein, in the case where none of R⁵ to R⁸ is a halogeno group, at least one of R⁵ to R⁸ comprises a substituted or unsubstituted condensed aromatic ring having 10 to 24 carbon atoms or a substituted or unsubstituted condensed heteroaromatic ring having 10 to 24 carbon atoms, and
wherein at least one of R⁵ to R⁸ comprises any of substituted or unsubstituted naphthalene, fluorene, phenanthrene, triphenylene, dibenzothiophene, dibenzofuran, and carbazole rings.

10. An organic compound represented by General formula (a1):

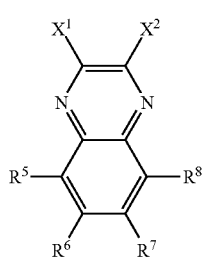
(a1)

wherein X¹ represents a halogeno group,
wherein X¹ represents a primary amino group,
wherein each of R⁵ to R⁸ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms,
wherein, in the case where none of R⁵ to R⁸ is a halogeno group, at least one of R⁵ to R⁸ comprises a substituted or unsubstituted condensed aromatic ring having 10 to 24 carbon atoms or a substituted or unsubstituted condensed heteroaromatic ring having 10 to 24 carbon atoms, and
wherein at least one of R⁵ to R⁸ comprises any of a substituted or unsubstituted arylene group having 6 to 24 carbon atoms or a substituted or unsubstituted heteroarylene group having 3 to 24 carbon atoms.

11. An organic compound represented by General formula (a1):

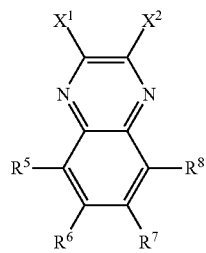
(a1)

wherein X¹ represents a halogeno group,
wherein X¹ represents a primary amino group,
wherein each of R⁵ to R⁸ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms,
wherein, in the case where none of R⁵ to R⁸ is a halogeno group, at least one of R⁵ to R⁸ comprises a substituted or unsubstituted condensed aromatic ring having 10 to 24 carbon atoms or a substituted or unsubstituted condensed heteroaromatic ring having 10 to 24 carbon atoms, and
wherein at least one of R⁵ to R⁸ represents any of General Formulae (A-1) to (A-4):

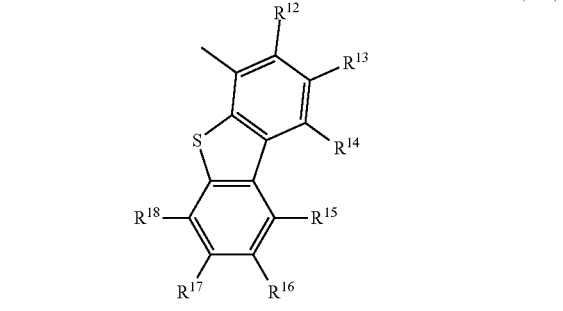
(A-1)

135
-continued

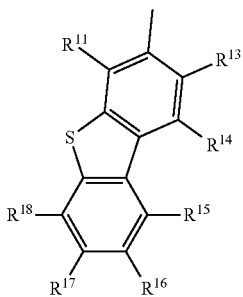
(A-2)

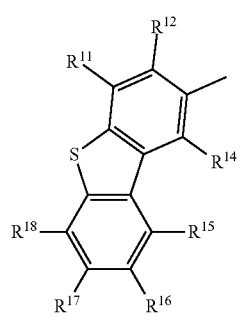
(A-3)

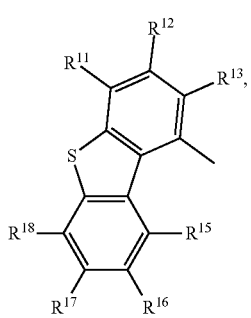
(A-4)

wherein each of $R^{11}$ to $R^{18}$ independently represents any of hydrogen, an alkyl group having 1 to 6 carbon atoms, and a substituted or unsubstituted phenyl group.

12. An organic compound represented by General formula (a3):

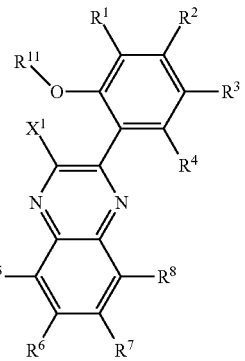
(a3)

wherein Q represents oxygen or sulfur, wherein $X^1$ represents any one of a halogeno group, a triflate group, and an amino group, wherein each of $R^1$ to $R^8$ independently represents any of hydrogen, a halogeno group, a substituted or unsubstituted alkyl group having 1 to 6 carbon atoms, a substituted or unsubstituted aryl group having 6 to 12 carbon atoms, and a substituted or unsubstituted heteroaryl group having 3 to 12 carbon atoms, wherein, in the case where none of $R^1$ to $R^8$ is a halogeno group, at least one of $R^5$ to $R^8$ comprises a substituted or unsubstituted condensed aromatic ring having 10 to 24 carbon atoms or a substituted or unsubstituted condensed heteroaromatic ring having 10 to 24 carbon atoms, and wherein $R^{11}$ represents an alkyl group having 1 to 6 carbon atoms.

13. The organic compound according to claim 12, wherein at least one of $R^5$ to $R^8$ comprises any of substituted or unsubstituted naphthalene, fluorene, phenanthrene, triphenylene, dibenzothiophene, dibenzofuran, and carbazole rings.

14. The organic compound according to claim 12, wherein at least one of $R^5$ to $R^8$ comprises substituted or unsubstituted naphthalene, fluorene, phenanthrene, triphenylene, dibenzothiophene, dibenzofuran, and carbazole rings via a substituted or unsubstituted arylene group having 6 to 24 carbon atoms or a substituted or unsubstituted heteroarylene group having 3 to 24 carbon atoms.

* * * * *